US009145528B2

(12) United States Patent
Goodall et al.

(10) Patent No.: US 9,145,528 B2
(45) Date of Patent: Sep. 29, 2015

(54) METHODS OF PREPARING OIL COMPOSITIONS FOR FUEL REFINING

(75) Inventors: Brian L. Goodall, Spring, TX (US); Alex M. Aravanis, San Diego, CA (US); Craig A. Behnke, San Diego, CA (US); Richard J. Cranford, San Diego, CA (US); Daniel J. Sajkowski, Frankfurt, IL (US)

(73) Assignee: SAPPHIRE ENERGY, INC., San Diego, CA (US)

( * ) Notice: Subject to any disclaimer, the term of this patent is extended or adjusted under 35 U.S.C. 154(b) by 233 days.

(21) Appl. No.: 13/265,508

(22) PCT Filed: Apr. 21, 2010

(86) PCT No.: PCT/US2010/031952
§ 371 (c)(1),
(2), (4) Date: Dec. 16, 2011

(87) PCT Pub. No.: WO2010/124030
PCT Pub. Date: Oct. 28, 2010

(65) Prior Publication Data
US 2012/0116138 A1     May 10, 2012

Related U.S. Application Data

(60) Provisional application No. 61/171,386, filed on Apr. 21, 2009.

(51) Int. Cl.
*C10L 1/04* (2006.01)
*C10G 45/08* (2006.01)
(Continued)

(52) U.S. Cl.
CPC ... *C10L 1/04* (2013.01); *C10G 3/46* (2013.01); *C10G 3/47* (2013.01); *C10G 3/49* (2013.01);
(Continued)

(58) Field of Classification Search
CPC ............... C10L 1/04; C10L 1/06; C10L 1/08; C11C 3/14; C11C 3/12; C11B 3/02; C10G 3/49; C10G 3/50; C10G 3/46; C10G 3/47; C10G 65/043; C10G 65/12; C10G 65/046; C10G 67/04; C10G 45/08; C10G 69/08; C10G 69/04; C10G 69/06; C10G 2300/44; C10G 2300/4018; C10G 2300/30; C10G 2300/1014; C10G 2300/205; C10G 2300/202; C10G 2400/08; C10G 2400/04; C10G 2400/10; C10G 2400/02; C12P 7/6463
USPC ............... 585/357, 469, 603, 733, 240
See application file for complete search history.

(56) References Cited

U.S. PATENT DOCUMENTS 3,778,365 A    12/1973  Hammer et al.
4,022,682 A     5/1977  Bludis et al.
(Continued)

FOREIGN PATENT DOCUMENTS

DE          2743618 A1    3/1979
WO    WO 2007/012643 A1  2/2007
(Continued)

OTHER PUBLICATIONS

Ramkumar K. Mandalam and Bernhard O. Palsson, Elemental Balancing of Biomass and Medium Composition Enchances Growth Capacity in High Density Chlorella vulgaris Cultures, John Wiley & Sons, Inc., 1998, p. 605-611.*
(Continued)

*Primary Examiner* — In Suk Bullock
*Assistant Examiner* — Philip Louie
(74) *Attorney, Agent, or Firm* — Sapphire Energy, Inc.

(57) ABSTRACT

Disclosed herein are methods and systems for upgrading (for example, removing heteroatoms, metals, or metalloids) an oil composition derived or extracted from a biomass. The upgraded oil composition can be used to make a desired product, for example, a fuel product.

12 Claims, 11 Drawing Sheets

(51) Int. Cl.

| | | |
|---|---|---|
| C10G 65/04 | (2006.01) | |
| C10G 65/12 | (2006.01) | |
| C10G 67/04 | (2006.01) | |
| C10G 69/04 | (2006.01) | |
| C10G 69/06 | (2006.01) | |
| C10G 69/08 | (2006.01) | |
| C10L 1/06 | (2006.01) | |
| C10L 1/08 | (2006.01) | |
| C10G 3/00 | (2006.01) | |
| C12P 7/64 | (2006.01) | |
| C11B 3/02 | (2006.01) | |
| C11C 3/12 | (2006.01) | |
| C11C 3/14 | (2006.01) | |

(52) U.S. Cl.
CPC *C10G 3/50* (2013.01); *C10G 45/08* (2013.01); *C10G 65/043* (2013.01); *C10G 65/046* (2013.01); *C10G 65/12* (2013.01); *C10G 67/04* (2013.01); *C10G 69/04* (2013.01); *C10G 69/06* (2013.01); *C10G 69/08* (2013.01); *C10L 1/06* (2013.01); *C10L 1/08* (2013.01); *C11B 3/02* (2013.01); *C11C 3/12* (2013.01); *C11C 3/14* (2013.01); *C12P 7/6463* (2013.01); *C10G 2300/1014* (2013.01); *C10G 2300/202* (2013.01); *C10G 2300/205* (2013.01); *C10G 2300/30* (2013.01); *C10G 2300/4018* (2013.01); *C10G 2300/44* (2013.01); *C10G 2400/02* (2013.01); *C10G 2400/04* (2013.01); *C10G 2400/08* (2013.01); *C10G 2400/10* (2013.01)

(56) References Cited

U.S. PATENT DOCUMENTS

| | | | |
|---|---|---|---|
| 4,605,489 | A | 8/1986 | Madgavkar |
| 4,645,589 | A | 2/1987 | Krambecl et al. |
| 4,992,605 | A | 2/1991 | Craig et al. |
| 5,002,919 | A | 3/1991 | Yamazaki et al. |
| 5,011,805 | A | 4/1991 | Dessau |
| 5,186,722 | A | 2/1993 | Cantrell et al. |
| 5,939,229 | A | 8/1999 | Robbins |
| 5,989,412 | A | 11/1999 | Okagami et al. |
| 6,166,230 | A | 12/2000 | Bijl et al. |
| 6,399,803 | B1 | 6/2002 | Corley et al. |
| 7,111,975 | B2 | 9/2006 | Fenton et al. |
| 7,425,412 | B2 | 9/2008 | Lo et al. |
| 7,491,858 | B2 | 2/2009 | Murzin et al. |
| 7,638,040 | B2 | 12/2009 | Van Wees et al. |
| 7,816,570 | B2 | 10/2010 | Roberts, IV et al. |
| 7,846,323 | B2 | 12/2010 | Abhari et al. |
| 8,193,399 | B2 * | 6/2012 | Gosling ............ 585/14 |
| 8,206,575 | B2 * | 6/2012 | Maesen et al. ........ 208/121 |
| 2007/0010682 | A1 | 1/2007 | Myllyoja et al. |
| 2008/0124318 | A1 * | 5/2008 | Lisson ........ 424/130.1 |
| 2008/0160593 | A1 | 7/2008 | Oyler |
| 2008/0173570 | A1 | 7/2008 | Marchand et al. |
| 2008/0305445 | A1 | 12/2008 | Roberts et al. |
| 2008/0308457 | A1 | 12/2008 | Dindi et al. |
| 2009/0029427 | A1 | 1/2009 | Miller |
| 2009/0069610 | A1 | 3/2009 | Roberts, IV et al. |
| 2009/0077864 | A1 | 3/2009 | Marker et al. |
| 2009/0077867 | A1 | 3/2009 | Marker et al. |
| 2009/0126260 | A1 | 5/2009 | Aravanis et al. |
| 2009/0259082 | A1 | 10/2009 | Deluga et al. |
| 2009/0266743 | A1 | 10/2009 | Yao et al. |
| 2009/0298159 | A1 | 12/2009 | Wu et al. |
| 2009/0314688 | A1 * | 12/2009 | Gordon et al. ............ 208/223 |
| 2010/0050502 | A1 | 3/2010 | Wu et al. |
| 2010/0170144 | A1 * | 7/2010 | Day et al. .............. 44/388 |
| 2010/0176026 | A1 * | 7/2010 | Cole et al. ........... 208/49 |
| 2010/0239712 | A1 | 9/2010 | Brooks et al. |
| 2010/0297749 | A1 | 11/2010 | Aravanis et al. |
| 2011/0092725 | A1 | 4/2011 | Jones |
| 2011/0105813 | A1 | 5/2011 | Roberts, IV et al. |

FOREIGN PATENT DOCUMENTS

| | | |
|---|---|---|
| WO | WO 2007/027955 A2 | 3/2007 |
| WO | WO 2007/064014 A2 | 6/2007 |
| WO | WO 2007/068796 A2 | 6/2007 |
| WO | WO 2007/687896 A2 | 6/2007 |
| WO | WO 2008/103204 A2 | 8/2008 |
| WO | WO 2009/000838 A2 | 12/2008 |
| WO | WO 2009/015055 A2 | 1/2009 |
| WO | WO 2009/039347 A1 | 3/2009 |
| WO | WO 2010/002886 A1 | 1/2010 |
| WO | WO 2011/025616 A2 | 3/2011 |

OTHER PUBLICATIONS

Teresa M. Mata, Antonio A. Martins, and Nidia S. Caetano, Microalgae for biodiesel production and other applications: A review, Renewable and Sustainable Energy Reviews, 2009, p. 217-232.*

Amos Richmond, Handbook of Microalgal Culture, Biotechnology and Applied Phycology, Blackwell Science, 2004.*

Oilgae, Chlorophyll, Production, Uses—Oilgae—Oil from Algae, http://www.oilgae.com/non_fuel_products/chlorophyll.html, pp. 1-4, accessed Jun. 10, 2014.*

Brown et al., "Hydrothermal liquefaction and gasification of Nannochloropsis sp." Energy and Fuels, 2010, vol. 24, pp. 3639-3646.

Fu et al., "Catalytic hydrothermal deoxygenation of palmitic acid." Energy Environ. Sci., 2010, vol. 3, pp. 311-317.

Peterson et al., "Thermochemcial biofuel production in hydrothermal media: A review of sub- and supercritical water technologies." Energy & Environmental Science, 2008, vol. 1, pp. 32-65.

Shuping et al., "Production and characterization of bio-oil from hydrothermal liquefaction of microalgae Dunaliella tertiolecta cake." Energy, 2010, vol. 35, pp. 5406-5411.

Valdez et al., "Characterization of product fractions for hydrothermal liquefaction of Nannochloropsis sp and the influence of solvents." Energy & Fuels, 2011, vol. 25, pp. 3235-3243.

Associated Press, NBC News. Algae used in biofuel U.S. jet test flight. www.nbcnews.com/id/28547191/ns/us_news-environment/t/algae-used-biofuel-us-jet-test-flight/#.U05pg1 Jan. 2009.

NREL. Jet Fuel From Microalgal Lipids. National Renewable Energy Laboratory Conference Paper. NREL, Colorado, US, Jul. 1, 2006, pp. 1-2, XP008105365.

Oilgae. Algae aviation fuel. Oilgae Discussions on energy from algae.Jan. 10, 2009. www.oilgae.com/forum/viewtopic.php?f=40 &=162.

St. John. Continental picks Sapphire Energy for Bio Jet Fuel. Dec. 8, 2008. ww.greentechmedia.com/articles/read/continental-picks-sapphire-energy-for-bio-jet-fuel-5334.

UOP. Honeywell's UOP green fuel technology powered biofuel demonstration flights for Japan Airlines, Air New Zealand and Continental Airlines. Feb. 5, 2009. http://www51.honeywell.com/honeywell/news-events/case-studies-n3n4/green_jet_fuel.html?c=36.

EP Search Report Application Serial No. 10767732.0 dated May 21, 2014.

* cited by examiner

|  | Crude Oil | Algae Oil |
|---|---|---|
| C | 84-87% | 77-78% |
| H | 11-14% | 11-12% |
| S | <0.1-8% | <<0.1% |
| N | <0.1-1.5% | ~0.5-4% |
| O | <0.1% | 10-12% |
| P | <<0.1% | 0.3-1% |
| Olefins | <1% | ? |
| Metals | <0.1-0.15% | ~0.05% |

Figure 1

METHODS OF PREPARING OIL COMPOSITIONS FOR FUEL REFINING

CROSS REFERENCE TO RELATED APPLICATION

This application claims the benefit of U.S. Provisional Application No. 61/171,386, filed Apr. 21, 2009, the entire contents of which are incorporated by reference for all purposes.

INCORPORATION BY REFERENCE

All publications, patents, patent applications, public databases, public database entries, and other references cited in this application are herein incorporated by reference in their entirety as if each individual publication, patent, patent application, public database, public database entry, or other reference was specifically and individually indicated to be incorporated by reference.

BACKGROUND

Carbon-based fossil fuels, such as coal, petroleum and natural gas, are finite and non-renewable resources. At the current consumption rate, supplies of fossil fuels will be exhausted in the near future. In addition, burning fossil fuels has resulted in a rise in the concentration of carbon dioxide in the atmosphere, which is believed to have caused global climate change.

Biofuels are viable alternatives to fossil fuels for several reasons. Biofuels are typically renewable energy sources produced from biomass, a material derived from recently living organisms. Because transportation-related gasoline consumption represents the majority of all liquid fossil fuel use, supplementing or replacing liquid fossil fuel (e.g. gasoline) with liquid biofuels can reduce our reliance on fossil fuels, and lower the amount of carbon dioxide released into the atmosphere.

The energy benefit of using biofuels such as ethanol (obtained from, for example, sugar cane, potato, manioc, and maize) has been questioned. Ethanol has a lower energy content than gasoline, therefore, more ethanol is required to provide the same energy output as gasoline. More significantly, the production of both ethanol and lipids (e.g. obtained from biodiesel) is currently driven by the use of fossil fuel. For example, the energy required for producing ethanol includes running farm machinery and irrigation, transporting and grinding the crop, producing pesticides and fertilizer, and fermenting and distilling ethanol. There have been concerns that the energy input for ethanol production may exceed the energy output from the combustion of ethanol. In addition, widespread production and use of ethanol and biodiesel will require constructing new distribution pipelines, because neither is suitable for transportation using existing fuel-distribution infrastructure. Moreover, any large-scale development of crop-based fuels such as ethanol and traditional biodiesel will compete for the same resources as food production (e.g. farm land and water), and ultimately be limited by the amount of arable land.

Currently, much work has been focused on refining algal oil using techniques used in the refining of vegetable oils. To date, however, none of these methods have worked for refining algal oil. Thus, a need exists for methods to refine algal oils.

Vegetable oils such as soy, canola, and camelina are essentially pure triglycerides of C16-18 free fatty acids which are extracted or expelled from the seeds of the plants where they are stored for energy. The resulting oil compositions can then be refined, bleached, and deodorized (RBD) to afford the final product oils as pure, crystal-clear materials that can be used in the food industry, soap industry, or biodiesel industry. These triglycerides are also the feedstock of choice for hydrotreating routes to jet fuel (UOP) and green diesel (UOP and Neste). However, due to the food versus oil debate, and the rising cost of vegetable oils the economic and social viability of these biofuels is questionable. A source of triglycerides is needed that does not compete with land used for commercial agriculture.

As mentioned above, vegetable oils such as soy, are purified by the RBD process in which trace levels (e.g. 1% or less) of phospholipids and free fatty acids are removed. Even lower levels of components such as sterol glucosides and chlorophyll are also removed. The small amounts of removed components can be treated as waste.

In theory, it is possible to purify algal oil using the RBD process described above. However, one fundamental difference between algal oil and traditional vegetable oils described above is that algal oil is harvested from the whole algal biomass and not selectively from a triglyceride storage system such as a seed. Algae oil is typically not essentially pure triglycerides, but rather a combination of triglycerides and significant levels (e.g. 1% to more than 40%) of a variety of other oil or lipid components, for example, chlorophylls and/or chlorophyllides, isoprenoids (including carotenoids), and phospholipids. For example, saline algae such as *Duneliella viridis* can deliver oils containing 30-40% of phospholipids. In addition, all photosynthetic algae deliver oils containing significant levels (for example, from about 0.6% to about 62% w/w) of chlorophyll or derivatives of chlorophyll.

The problem is that food-oil processing methods (such as RED) can deliver triglycerides ideally suited for converting to fuels, but a large fraction of the crude oil extracted (comprising, for example, phospholipids, chlorophyll, and free fatty acids) from algae (e.g. 10%-50%) is lost as waste making the overall economic and environmental aspects of using algae impractical. Thus, there is a need for a refining ("upgrading") technology that removes, for example, undesirable heteroatoms (e.g. P, N and metals) from an oil composition without loosing potential sources of hydrocarbon fuels as waste.

Furthermore, at commercial scale, it is economically desirable to transport the refined ("upgraded") algae oil by existing pipelines used by the petroleum industry. Additional sources of transport include, for example, truck, rail, and ship. Even if the heteroatoms (for example, P, N and metals) are removed from the oil composition the resulting "Green Crude"—like vegetable oils—will be excluded from transport via pipelines because of its high oxygen content, oxidative instability, and corrosivity, among other reasons.

Therefore, there is a need to remove essentially or almost essentially all heteroatoms (for example, O, P, N, and S) along with metals, and metalloids, if present, from an oil composition to deliver a refined oil composition comprising a hydrocarbon fraction that is essentially or almost essentially devoid of these components and that can be transported via existing pipelines, and/or further refined in existing refinery infrastructures.

In order to use the existing petroleum infrastructure, for example, refineries and pipelines, biofuel, such as an oil composition obtained from a biomass needs to be "upgraded". Upgrading includes, for example, the removal of heteroatoms (S, N, O, P), removal of metals or metalloids, saturation of double bonds and/or aromatics by addition of hydrogen, isomerization of the carbon backbone to introduce branches to the backbone, and/or reforming to make aromatic compounds.

Provided herein are methods and systems useful for the upgrading of an oil composition.

SUMMARY

1. A method for upgrading an oil composition obtained from a biomass, comprising, removal of a heteroatom, a metal, or a metalloid from the oil composition, wherein the biomass is obtained from a photosynthetic bacterium, a yeast, an alga, or a vascular plant. 2. The method of claim 1, wherein the removal step further comprises any one or more of: i) saturation of a double bond and/or an aromatic present in the oil composition by addition of hydrogen; ii) isomerization of a carbon backbone present in the oil composition in order to introduce branches to the carbon backbone; or iii) reformation of a compound present in the oil composition to make an aromatic compound. 3. The method of claim 1 or claim 2, wherein the heteroatom is Phosphorus (P), Nitrogen (N), Oxygen (O), or Sulfur (S). 4. The method of any one of claims 1 to 3, wherein the metal or metalloid is Boron (B), Calcium (Ca), Chromium Cr), Copper (Cu), Iron (Fe), Lead (Pb), Lithium (Li), Magnesium (Mg), Manganese (Mn), Nickel (Ni), Phosphorus (P), Potassium (K), Silicon (Si), Sodium (Na), Strontium (Sr), or Zinc (Zn). 5. The method of any one of claims 1 to 4, wherein the oil composition comprises at least one of: i) a phosphorus concentration of 0% to 5% w/w; ii) a nitrogen concentration of 0% to 10% w/w; iii) a sulfur concentration of 0% to 5% w/w; or iv) an oxygen concentration of 0% to 20% w/w. 6. The method of claim 1, wherein the oil composition comprises, greater than about 0.05% to about 5.0% w/w nitrogen, greater than about 6% to about 16% w/w oxygen, or greater than about 0.03% to about 1.0% w/w sulfur. 7. The method of claim 1, wherein the oil composition comprises, greater than about 0.01% to about 10.0% w/w nitrogen, greater than about 3% to about 18% w/w oxygen, or greater than about 0.01% to about 3.0% w/w sulfur. 8. The method of claim 1, wherein the oil composition comprises, greater than about 0.05% w/w nitrogen, greater than about 6% w/w oxygen, or greater than about 0.0005% w/w phosphorus. 9. The method of any one of claims 1 to 8, wherein the removal of the heteroatom, metal, or metalloid is by at least one catalyst. 10. The method of claim 9, wherein the catalyst is placed in at least one reactor. 11. The method of claim 10, wherein the catalyst is placed in two or more reactors. 12. The method of claim 10, wherein at least two different catalysts are placed in the reactor. 13. The method of claim 10, wherein the reactor is a fixed bed reactor or a fluidized bed reactor. 14. The method of claim 10, wherein the reactor is a single-stage reactor or a multistage reactor. 15. The method of claim 9, wherein the catalyst comprises metals such as Ni/Mo, Co/Mo, W/Mo, or Ni/W. 16. The method of claim 9, wherein the catalyst is a catalytic cracking catalysts (FCC) on a silica-alumina support. 17. The method of claim 9, wherein the catalyst comprises a noble metal. 18. The method of claim 9, wherein the catalyst is a naphtha reforming catalyst. 19. The method of claim 9, wherein the catalyst comprises zeolite. 20. The method of claim 9, wherein the catalyst comprises Ni/Mo supported on alumina. 21. The method of claim 9, wherein the catalyst comprises Co/Mo supported on alumina. 22. The method of claim 9, wherein the catalyst comprises Pt supported on alumina. 23. The method of claim 9, wherein the catalyst comprises Ni/W supported on alumina. 24. The method of claim 9, wherein the catalyst is combined with a support. 25. The method of claim 24, wherein the support comprises alumina, silica, silica-alumina, zirconia, or a noble metal. 26. The method of claim 9, wherein the catalyst comprises a metal of Group VIA, Group VIb, or Group VIII of Periodic Table of Elements. 27. The method of claim 9, wherein the catalyst comprises a metal of Group VIb or Group VIII of Periodic Table of Elements supported on a porous refractory oxide carrier. 28. The method of claim 27, wherein the porous refractory oxide carrier comprises alumina, silica, magnesia, silica-alumina, silica-magnesia, zirconia, titania, or silica-titania. 29. The method of claim 9, wherein the catalyst is a "supported" Pd, Pt, Ru, Rh, Ni, NiMo or CoMo catalyst, wherein the support is activated carbon, alumina, zirconia, or silica. 30. The method of any one of claims 1 to 29, wherein the removal of the heteroatom, metal, or metalloid is by at least one of a hydrodemetallization (HDM), a hydrodenitrogenation (HDN), a hydrodesulfitrization (HDS), or a hydrodeoxygenation (HDO) reaction. 31. The method of any one of claims 1 to 30, wherein removal of the metal or metalloid occurs prior to removal of the heteroatom, 32. The method of any one of claims 1 to 31, wherein chlorophyll or chlorophyllide is also removed from the oil composition by a chlorophyllase, a RCC reductase, a dechelatase, or a pheophorbide a oxygenase. 33. The method of any one of claims 1 to 32, wherein the removal is carried out at a temperature of from about 315 to about 480 C (from about 600 to about 900 F); a total pressure and/or hydrogen partial pressure of from about 100 to about 3000 psi; a hydrogen to oil ratio of from about 100 to about 2000 scf/Bbl; and a space velocity from about 1.5 to about 8. 34. The method of any one of claims 1 to 33, wherein the upgraded oil composition is further refined by catalytic reforming. 35. The method of claim 34, wherein the catalytic reforming is dehydrogenation of naphthenes to convert the naphthenes into aromatics, isomerization of normal paraffins to isoparaffins, dehydrogenation and aromatization of paraffins to aromatics, or hydrocracking of paraffins into smaller molecules. 36. The method of any one of claims 1 to 33, wherein the upgraded oil composition is further refined by distillation, fractionation, extraction, solvent extraction, hydrotreatment, isomerization, dimerization, alkylation, or cracking. 37. The method of claim 36, wherein the cracking is thermal cracking, fluid catalytic cracking, thermoform catalytic cracking, catalytic cracking, steam cracking, or hydrocracking. 38. The method of any one of claims 1 to 36, wherein the upgraded oil composition is used to make gasoline, diesel fuel, jet fuel, fuel additives, petrochemicals, plastics, resins, fibers, elastomers, lubricants, or gels. 39. The method of any one of claims 1 to 38, wherein the upgraded oil composition is used in a petroleum refinery. 40. The method of any one of claims 1 to 38, wherein the upgraded oil composition is used in a distillate blendstock. 41. The method of any one of claims 1 to 38, wherein the upgraded oil composition is in fluidic communication with an oil pipeline. 42. The method of any one of claims 1 to 38, wherein the upgraded oil composition is in fluidic communication with a distilling device. 43. The method of claim 42, wherein the distilling device is configured to remove hydrocarbons that are C4 hydrocarbons or smaller from the oil composition. 44. The method of any one of claims 1 to 43, wherein the oil composition is obtained from the biomass by solvent extraction. 45. The method of any one of claims 1 to 43, wherein the biomass is a wet, a dry, or a semi-dry biomass, 46. The method of any one of claims 1 to 45, wherein the biomass comprises hydrocarbons of chain length C10 and greater. 47. The method of any one of claims 1 to 46, wherein the photosynthetic bacterium is a member of genera *Synechocystis*, genera *Synechococcus*, or genera *Athrospira*. 48. The method of any one of claims 1 to 46, wherein the photosynthetic bacterium is a cyanobacterium. 49. The method of any one of claims 1 to 46, wherein the alga is a microalga. 50. The method of any one of claims 1 to 46, wherein the alga is *C. reinhardtii, D. satina, H. pluvatis, S. dimorphus, D. viridis, D. tertiolecta; N. oculata*, or *N. salina*. 51. The method of any one of claims 1 to 46, wherein the alga is a cyanophyta, prochlorophyta, a rhodophyta, a chlorophyta, a heterokornophyta, a tribophyta, a glaucophyta, a chtorarachniophyta, a euglenophyta, a eugtenoid, a haptophyta, a chrysophyta, a cryptophyta, a cryptomonad, dinophyta, a dinotlagellata, a pyrmnesiophyta, a bacillariophyta, a xanthophyta, a eustigmatophyta, a raphidophyta, a phaeophyta, or a phytoplankton, 52. The method of any one of claims 1 to 46, wherein the photosynthetic bacterium, yeast, alga, or vascular plant has been transformed with a nucleic acid sequence encoding a protein involved in the isoprenoid pathway. 53. The method of claim 52, wherein the protein is a terpene synthase, 54. The method of claim 53, wherein the terpene synthase is a fusicoccadiene synthase, a kaurene synthase, a casbene synthase, a taxadiene synthase, an abietadiene synthase, a homolog of any one of the above, or a chimera or fusion comprising any one of the above. 55. An upgraded oil composition made by the method of any one of claims 1 to 54. 56. A method for upgrading an oil composition comprising: catalytically removing nitrogen from the oil composition to create an upgraded oil composition, wherein the oil composition comprises greater than about 0.5% w/w nitrogen, greater than about 8% w/w oxygen or greater than about 0.1% phosphorus. 57. The method of claim 56, wherein the oil composition comprises greater than about 2.5, greater than about 3, greater than about 3.5, greater than about 4, greater than about 4.5, or greater than about 5% w/w nitrogen. 58. The method of claim 56, wherein the oil composition comprises greater than about 9 or greater than about 10% w/w oxygen. 59. The method of claim 56, wherein the oil composition comprises greater than about 0.1, greater than about 0.2, greater than about 0.5, greater than about 1, or greater than about 2% w/w phosphorous.

60. A method for preparing an upgraded oil composition comprising: catalytically removing i) a metal or metalloid, ii) nitrogen, or iii) oxygen from an oil composition to create the upgraded oil composition. 61. The method of claim 60, further comprising delivering the upgraded oil composition to an oil pipeline. 62. The method of claim 60, wherein the metal or metalloid is removed before nitrogen or oxygen.

63. A method for preparing an upgraded oil composition comprising: removing chlorophyll or chlorophyllide from an oil composition; and catalytically removing metals or metalloids and oxygen from the oil composition to create the upgraded oil composition. 64. The method of claim 63, wherein the oil composition is obtained from an algal biomass. 65. The method of claim 63, wherein the removing step is carried out at a temperature of greater than about 250, greater than about 300, greater than about 350, greater than about 400, greater than about 450, or greater than about 500° C. 66. The method of claim 63, wherein the removing step is carried out at a pressure of hydrogen of greater than about 500, greater than about 750, or greater than about 1000 psi. 67. The method of any one of claims 63 to 66, further comprising refining the upgraded oil composition. 68. The method of claim 67, wherein the refining comprises catalytic cracking. 69. The method of any one of claims 63 to 66, further comprising combusting the upgraded oil composition. 70. The method of any one of claims 63 to 66, further comprising distilling the upgraded oil composition to remove hydrocarbons that are $C_4$ hydrocarbons or smaller. 71. The method of claim 70, wherein the hydrocarbons that are removed by the distilling are used to heat the method.

72. A system for preparing a hydrocarbon composition for refining, comprising: a metal-removing reactor comprising a metal-removing catalyst configured to remove metal or metalloid atoms from an oil composition; and a nonmetal-removing reactor comprising a nonmetal-removing catalyst configured to remove at least one of nitrogen or oxygen or sulfur from the oil composition, wherein the nonmetal-removing reactor is in fluidic communication with the metal-removing reactor. 73. The system of claim 72, further comprising a second metal-removing reactor, wherein the second metal-removing reactor is interchangeable with the metal-removing reactor. 74. The system of claim 73, further comprising: a third metal-removing reactor interchangeable with the second metal-removing reactor or the metal-removing reactor, wherein when the metal-removing reactor is in operation, the second metal-removing reactor is on stand-by and comprises an unused metal-removing catalyst, and the third metal-removing reactor is being emptied and/or refilled with a second unused metal-removing catalyst. 75. The system of any one of claims 72 to 74, wherein the metal-removing catalyst comprises: a support of alumina, aluminosilicate, or aluminosilic; and Co/Mo, Ni/Mo, or W/Mo. 76. The system of any one of claims 72 to 75, further comprising a second nonmetal-removing reactor configured to remove at least one of nitrogen or oxygen or sulfur from the oil composition, wherein the second nonmetal-removing reactor is in fluidic communication with the nonmetal-removing reactor. 77. The system of claim 76, wherein the nonmetal-removing catalyst comprises: a support of alumina, aluminosilicate, or aluminositic; and Co/Mo, Ni/Mo, or W/Mo. 78. The system of any one of claims 72 to 77, wherein the oil composition is obtained from an algal biomass. 79. The system of any one of claims 72 to 77, wherein the system is in fluidic communication with an oil pipeline. 80. The system of any one of claims 72 to 79, further comprising a distilling device in fluidic communication with the system configured to remove hydrocarbons that are $C_4$ hydrocarbons or smaller from the hydrocarbon composition.

81. An upgraded oil composition obtained from a biomass, made by the process of: i) removing a heteroatom, a metal, or a metalloid from an oil composition, wherein the biomass is obtained from a photosynthetic bacterium, a yeast, an alga, or a vascular plant.

82. An upgraded oil composition obtained from a biomass, made by the process of i) removing a heteroatom, a metal, or a metalloid from an oil composition, wherein the biomass is obtained from a photosynthetic bacterium, a yeast, an alga, or a vascular plant; ii) saturation of a double bond and/or an aromatic present in the oil composition by addition of hydrogen; iii) isomerization of a carbon backbone present in the oil composition in order to introduce branches to the carbon backbone; or iii) reformation of a compound present in the oil composition to make an aromatic compound.

83. An upgraded oil composition obtained from an algal biomass, made by the process of: i) removing a heteroatom, a metal, or a metalloid from an oil composition to obtain the upgraded oil composition, wherein the upgraded oil composition is used to make a product with a freezing point of −60° C. to −70° C.

84. An upgraded oil composition obtained from an algal biomass, made by the process of i) removing a heteroatom, a metal, or a metalloid from an oil composition to obtain the upgraded oil composition, wherein the upgraded oil composition is used to make a product with a freezing point of −50° C. to −75° C.

85. An upgraded oil composition obtained from an algal biomass, made by the process of i) removing a heteroatom, a metal, or a metalloid from an oil composition to obtain the upgraded oil composition, wherein the upgraded oil composition is used to make a product with a freezing point of −67° C.

86. A method for upgrading an oil composition obtained from a biomass, comprising: i) removal of a heteroatom, a metal, or a metalloid from the oil composition; ii) saturation of a double bond and/or an aromatic present in the oil composition by addition of hydrogen; iii) isomerization of a carbon backbone present in the oil composition in order to introduce branches to the carbon backbone; or iv) reformation of a compound present in the oil composition to make an aromatic compound, wherein the biomass is obtained from a non-vascular photosynthetic organism. 87. The method of claim 86, wherein the non-vascular photosynthetic organism is an alga. 88. The method of claim 87, wherein the alga is *C. reinhardtii, D. salina, H. pluvalis, S. dimorphus, D. viridis, D. tertiolecta, N. ocutata,* or *N. salina.* 89. The method of claim 87, wherein the alga is a cyanophyta, a prochlorophyta, a rhodophyta, a chlorophyta, a heterokontophyta, a tribophyta, a glaucophyta, chlorarachniophyte, a euglenophyta, a euglenoid, haptophyta, a chrysophyta, a cryptophyta, a cryptomonad, dinophyta, a dinoflagellata, a pyrmnesiophyta, a bacillariophyta, a xanthophyta, a eustigmatophyta, a raphidophyta, a phaeophyta; or a phytoplankton.

90. A method for upgrading an oil composition obtained from an algal biomass, comprising: i) removing a heteroatom, a metal, or a metalloid from the oil composition to obtain the upgraded oil composition, wherein the upgraded oil composition is used to make a product with a freezing point of −60'C to −70° C.

91. A method for upgrading an oil composition obtained from an algal biomass, comprising: i) removing a heteroatom, a metal, or a metalloid from the oil composition to obtain the upgraded oil composition, wherein the upgraded oil composition is used to make a product with a freezing point of −50° C. to −75° C.

92. A method for upgrading an oil composition obtained from an algal biomass, comprising: i) removing a heteroatom, a metal, or a metalloid from the oil composition to obtain the upgraded oil composition, wherein the upgraded oil composition is used to make a product with a freezing point of −67"C.

93. An upgraded oil composition made by the method of any one of claims 56 to 71 and 86 to 92.

In an embodiment, a method is disclosed herein for preparing a fuel that comprises catalytically removing heteroatoms from an oil composition from biomass to create a refined oil composition.

In an embodiment, a method for preparing a fuel from an oil composition comprises catalytically removing nitrogen from an oil composition to create a refined oil composition, wherein said oil composition comprises greater than about 0.5% w/w nitrogen, greater than about 8% w/w oxygen or greater than about 0.1% w/w phosphorus. In some embodiments, the oil composition comprises greater than about 2.5, greater than about 3, greater than about 3.5, greater than about 4, greater than about 4.5, or greater than about 5% w/w nitrogen. In some embodiments, the oil composition comprises greater than about 9 or greater than about 10% w/w oxygen. In some embodiments, the oil composition comprises greater than about 0.1, greater than about 0.2, greater than about 0.5; greater than about 1, or greater than about 2% w/w phosphorous.

In an embodiment, a method is disclosed for preparing a fuel from an oil composition comprising catalytically removing (i) metals or metalloids, (ii) nitrogen, and (iii) oxygen from an oil composition to create a refined composition.

In some embodiments, a method herein comprises combusting a refined composition. A method can comprise delivering said refined composition to an oil pipeline. In some embodiments, the metal or metalloid is removed prior to removing nitrogen or oxygen.

In an embodiment, a method for preparing a fuel from an oil composition comprises: removing chlorophyll or chlorophyllide from an oil composition; and catalytically removing (i) metals or metalloids and (ii) oxygen from an oil composition to create a refined composition.

The oil composition can be an algae extract.

As disclosed herein, a removing step can be carried out at a temperature of greater than about 250, greater than about 300, greater than about 350, greater than about 400, greater than about 450, or greater than about 500° C.

In some embodiments, a removing step can be carried out at a pressure of hydrogen of greater than about 500, greater than about 750, or greater than about 1000 psi.

In some embodiments, a method as described herein can further comprise refining the refined composition, for example, catalytically cracking the composition.

In some embodiments, methods can further comprise distilling the refined composition to remove hydrocarbons that are C4 hydrocarbons or smaller. The hydrocarbons removed by the distilling can be used to heat the method.

In an embodiment, a system is disclosed for preparing a hydrocarbon composition for refining that comprises: a metal-removing reactor comprising a metal-removing catalyst configured to remove metal or metalloid atoms from an oil composition; and a nonmetal-removing reactor comprising a nonmetal-removing catalyst configured to remove at least one of nitrogen or oxygen from the oil composition, wherein the nonmetal-removing reactor is in fluidic communication with the metal-removing reactor.

A system can comprise a first metal-removing reactor in parallel with a second metal-removing reactor, wherein the first metal-removing reactor is interchangeable with the second metal-removing reactor, in some embodiments, a system further comprises: a third metal-removing reactor in parallel and interchangeable with the second metal-removing reactor and the first metal-removing reactor, wherein when one of the metal-removing reactors is in operation, another metal-removing reactor is on stand-by and comprises unused metal-removing catalyst, and the final metal-removing reactor is being emptied and/or refilled with unused metal-removing catalyst.

A metal-removing catalyst can, for example, comprise a support of alumina, aluminosilicate, aluminosilic; and Co/Mo, Ni/Mo, or W/Mo.

In some embodiments, a system comprises a first nonmetal-removing reactor configured to remove at least one of nitrogen or oxygen from an oil composition, wherein the first nonmetal-removing reactor is in fluidic communication with a second nonmetal-removing reactor.

A nonmetal-removing catalyst can, for example, comprise a support of alumina, aluminosilicate, aluminosilic; and Co/Mo, Ni/Mo, or W/Mo.

In some embodiments, a system herein is in fluidic communication with an oil pipeline.

In some embodiments, a system herein can further comprise a distilling device in fluidic communication with at least one reactor configured to remove hydrocarbons that are C4 hydrocarbons or smaller from a hydrocarbon composition obtained from the system.

BRIEF DESCRIPTION OF THE DRAWINGS

These and other features, embodiments, and advantages of the present disclosure will become better understood with regard to the following description, appended claims and accompanying figures where:

FIG. 1 shows a comparison of certain components of an exemplary crude oil and an exemplary algal oil.

DETAILED DESCRIPTION

Figure 2:
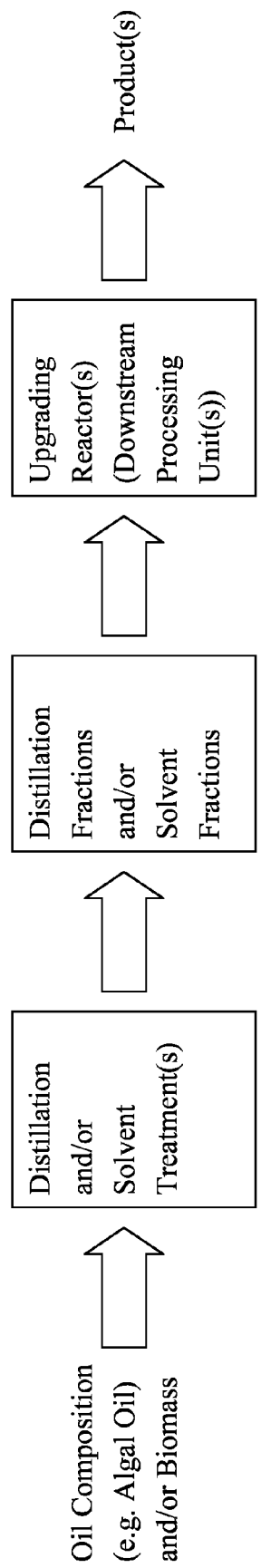
FIG. 2 shows an overview of the processes that can be involved in the production of a product obtained from a biomass and/or oil composition.

The following detailed description is provided to aid those skilled in the art in practicing the present disclosure. Even so, this detailed description should not be construed to unduly limit the present disclosure as modifications and variations in the embodiments discussed herein can be made by those of ordinary skill in the art without departing from the spirit or scope of the present disclosure.

As used in this specification and the appended claims, the singular forms "a", "an" and "the" include plural reference unless the context clearly dictates otherwise.

Endogenous

An endogenous nucleic acid, nucleotide, polypeptide, or protein as described herein is defined in relationship to the host organism. An endogenous nucleic acid, nucleotide, polypeptide, or protein is one that naturally occurs in the host organism.

Exogenous

An exogenous nucleic acid, nucleotide, polypeptide, or protein as described herein is defined in relationship to the host organism. An exogenous nucleic acid, nucleotide, polypeptide, or protein is one that does not naturally occur in the host organism or is a different location in the host organism.

Disclosed herein are methods and systems for "upgrading" an oil composition obtained from a biomass, so that the "upgraded" oil composition can be used in the existing petroleum infrastructure, such as in refineries and pipelines. For example, the upgraded oil composition can be refined using methods that are similar or identical to the processes of refining petroleum to create gasoline.

The biomass can be obtained from an organism, for example, an algae.

Biomass

An oil composition, derived from a biomass, can comprise one or more organic compounds obtained from a biological organism that was recently alive, for example, alive within the last 50 years. Unlike fossil fuel-based crude oil, which originated from plant life up to 600 millions years ago, oil compositions derived from a biomass can be derived from living or recently living organisms. The oil composition can comprise predominantly carbon and hydrogen, and may also comprise heteroatoms such as oxygen, nitrogen, phosphorus, and sulfur. The oil composition can comprise hydrocarbons extracted from genetically modified biological organisms, such as algae and bacteria.

The oil composition can be "upgraded" and/or further refined, and then used in compositions that are suitable as fuels (for example, gasoline, diesel fuel or jet fuel), fuel additives, petrochemicals, and can also be further processed into plastics, resins, fibers, elastomers, lubricants, or gels. Oil compositions can be chosen that are compatible with an existing infrastructure, for example, a petroleum refining process. In addition, light or rearranged hydrocarbons that are obtained from the biomass can be further processed or distributed using the existing infrastructure for refining petroleum.

In some embodiments, a biomass can comprise hydrocarbons in the form of terpenes, isoprenoids, lipids, alkyl esters, alkaloids, and/or phenyl propanoids. A terpene can refer to any terpenoid or isoprenoid that includes as well as pure hydrocarbons. In some embodiments, the terpenes occur naturally in the biomass, for example, carotenoids in an algal biomass. In other embodiments, terpenes can occur in a biomass that has been genetically modified to generate terpenes.

Biomass that comprises hydrocarbons, as those described herein, can be used as feedstocks in refineries. Like a conventional feedstock, an oil composition derived from biomass can be cracked or altered. In some embodiments, an oil composition derived from biomass is broken down into light hydrocarbons (hydrocarbons having fewer carbons than the oil composition).

Many types of hydrocarbons can occur naturally in a biomass. For example, hydrocarbons include lipids and nitrogen-containing hydrocarbons. Lipids can include, for example, fatty acids, fatty acid derivatives, and sterols. A fatty acid can comprise a long hydrocarbon chain terminated with a carboxylic acid (thereby comprising oxygen heteroatoms). The hydrocarbon chain can be either saturated or unsaturated and can range in length from about 12 to about 24 carbons (for example, C12-C24). A fatty acid derivative includes esters of a fatty acid. For example, glycerides (for example, vegetable oil) are lipids possessing a glycerol (propan-1,2,3-triol) core structure with one or more fatty acid groups. Additional fatty acid derivatives include alkyl esters, which are transesterification products of vegetable oils. Methanol can be used to produce methyl esters of fatty acids. Alkaloids and phenyl propanoids are nitrogen-containing hydrocarbons that can be obtained from a biomass, for example, an algal biomass.

Biomass containing hydrocarbons can be derived from renewable biological sources, which include naturally occurring organisms and genetically modified organisms. Hydrocarbons are present in many naturally occurring organisms (eukaryotic or prokaryotic), which include, for example, plant matter, fungi, algae, and bacteria. The biomass hydrocarbons described herein can be obtained from both living organisms and recently living organisms. The oil composition can be extracted from a whole or partial biomass. Sources of biomass include naturally occurring organisms as well as genetically modified organisms. In certain embodiments, such organisms are algae or bacteria.

Algae represent a source for biomass that are suitable for biological hydrocarbon production because algae rely on photosynthesis for energy production and can accumulate a high content of isoprenoids (for example, marine algae *Dunaliella salina*). Unlike crops, algae cultivation does not take up arable land and does not require an irrigation system. Moreover, algae are diverse microorganisms that can be genetically manipulated to increase the biosynthetic production of isoprenoids. The oil composition can be extracted from a whole or partial biomass. Sources of biomass include naturally occurring algae as well as genetically modified algae.

Obtaining an oil composition from a biomass can comprise solvent extraction of the oil composition from the biomass. Other methods of obtaining oil from a biomass are known to one of skill in the art. Examples of such methods are pyrolysis of the biomass or solvent free expeller extraction (cold-pressing).

In some embodiments, the product (e.g. fuel product) is collected by harvesting the organism. The product may then be extracted from the organism. In some instances, the product may be produced without killing the organisms. Producing and/or expressing the product may not render the organism unviable. In other instances, the product may be secreted into a growing environment.

The product-containing biomass can be harvested from its growth environment (e.g. lake, pond, photobioreactor, or partially closed bioreactor system, for example) using any suitable method. Non-limiting examples of harvesting techniques are centrifugation or flocculation. Once harvested, the product-containing biomass can be subjected to a drying process. Alternately, an extraction step may be performed on wet biomass. The product-containing biomass can be dried using any suitable method. Non-limiting examples of drying methods include sunlight, rotary dryers, flash dryers, vacuum dryers, ovens, freeze dryers, hot air dryers, microwave dryers and superheated steam dryers. After the drying process the product-containing biomass can be referred to as a dry or semi-dry biomass.

Terpenes (for example, diterpenes) can be produced from algae grown in harvesting ponds. Depending on the type of algae, the ponds may contain fresh or brine water. The algae are harvested and dried using techniques known to one of skill in the art. Terpenes can then be extracted from the dried algae using an organic solvent. A low boiling-point solvent can be used. The solvent can be recycled (for example, via distillation and condensation) when the terpene extract is concentrated. Exemplary solvents include, but are not limited to, hexane, carbon disulfide, carbon tetrachloride, chloroform, methylene chloride, petroleum ether, diethyl ether, acetone, water, glycerol, alcohol, heptane, methylpentane, toluene, methylisobutylketone, and mixtures thereof. The algal biomass can also be harvested and the terpenes extracted from a wet biomass.

An oil composition can be obtained several ways. For example, an organism may be harvested and dried and then the oil extracted from the lysed or destroyed cells. Alternatively, the cells can be chemically lysed, or mechanical force can be used to destroy the cell wall. Oil can be extracted from the organism, for example, an algae, using an organic solvent such as hexane. In addition, the oil can be extracted from the organism by a supersonic shockwave resulting in cell rupture (for example, as described in U.S. Pat. No. 7,111,975). Other methods of extracting oil from an organism can also be used with the methods and systems described herein, and such methods are known to one skilled in the art.

The biomass composition can be a wet, a dry, or a semi-dry biomass composition. In order to extract the oil from the biomass, the biomass can be heated to 25° C. to 95° C., 30° C. to 60° C., 37° C. 95° C. 60° C. to 250° C., or 80° C. to 200° C. Alternatively, in order to extract the oil from the biomass, the biomass can be cooled to less than 0 to −0.40° C. or −5° C. to −20° C.

In some embodiments, the pH of the media in which the host organism is grown, from which the biomass is obtained, can be controlled. The pH may be controlled using the addition of various acids. The acids used to control pH may include, for example, $CO_2$, nitric acid, phosphoric acid, or other acids. The pH of the media may be controlled to remain within the range of about pH 7.5 to about 8, about 8 to about 8.5, about 8.5 to about 9, about 9 to about 9.5, about 9.5 to about 10, about 10 to about 10.5, about 10.5 to about 11, or about 11 to about 11.5.

In one embodiment, an oil composition derived from a biomass, for example, an algal biomass, comprises hydrocarbons and terpenes of chain length C10 and greater that naturally occur in the algae. Different species of organisms may generate oil with different hydrocarbon mixtures. In some embodiments, an oil composition derived from algae is a mixture of oils from more than one species of algae. In some embodiments, an oil composition derived from algae comprises an increased amount of terpenes. In some embodiments, the oil from algae comprises terpenes not naturally produced by the algae.

In some embodiments, methods and systems discussed herein also comprise mixing the oil composition with a fuel component prior to being "upgraded". For example, a blend of algal oil and crude petroleum can be provided in a process as described herein and contacted with a catalytic composition. In another example, a blend of algal oil and a refined fuel such as gasoline can be contacted with a catalytic component. In another example, algal oil that has been prepared by a method or system herein can be blended with a fuel component before conventional refining. Examples of fuel components are fossil fuel, petroleum, gasoline, diesel, jet fuel, and any combination thereof.

In another embodiment, crude oil from an organism, for example, an algae, can be refined before being "upgraded". For example, the crude algal oil can be subjected to a RBD (refining bleaching deodorizing) process. In another example, the crude algal oil can be fractionated into desired components by distillation. The crude algal oil can be fractionated into hydrocarbon components of desired sizes, compositions, or shapes.

An oil composition obtained from a biomass can be refined in a similar manner to how crude petroleum oil is refined. For example, the refining process can include cracking (for example, catalytic cracking, thermal cracking, steam cracking and hydrocracking) as well as isomerization, alteration or chemical conversion.

In one embodiment, an organism, for example, an algae, is genetically modified prior to extraction of the oil. For example, an exogenous nucleic acid encoding an enzyme can be introduced into the chloroplast or nucleus of the algae, and expression of the enzyme results in the increased production of for example, a terpene or fatty acid. The terpene can be endogenous to the algae or exogenous to the algae. In one embodiment, the algae are genetically modified to upregulate the production of a terpene that naturally occurs in the algae.

In this example, the oil obtained from the algae comprises a greater concentration of terpenes than an unmodified algae. This oil is then capable of being cracked under catalytic cracking conditions, as described herein. In another embodiment, the algae are genetically modified to upregulate the production of a terpene or fatty acid that does not naturally occur in the algae. For example, a gene encoding a modified enzyme that generates a terpene through the isoprenoid biosynthetic pathway can be inserted into the chloroplast or nucleus of the algae. In addition, the organism can be genetically modified to produce a hydrocarbon that is useful in the production of a fuel product. For example, the algae can be genetically modified to produce an increased amount of a sesquiterpene, as compared to an unmodified algae. Genetic modification of an organism to generate a fatty acid, can include the introduction of a gene encoding an acetyl-CoA enzyme into the organism.

Methods

Methods for upgrading an oil composition to create a refined or "upgraded" oil composition are provided herein.

Methods and systems are provided herein to remove at least one, two or more, or essentially all heteroatoms (for example, oxygen, nitrogen, phosphorous, sulfur, and metal) from an oil composition derived from a biomass. In some embodiments, the resulting refined or "upgraded" oil composition can be converted to fuel in an existing refinery infrastructure (for example, for processing fuels derived from fossil fuels). In some embodiments, the upgraded oil composition obtained from the methods or systems described herein meet American Society for Testing and Materials (ASTM) fuel standards, for example, environmentally standards.

Other methods known to one of skill in the art can be used prior to, during (e.g. simultaneously), or after the upgrading of an oil composition, for example, the removal of heteroatoms and/or metals and/or metalloids from an oil composition.

Upgrading includes, for example, the removal of heteroatoms (e.g. S, N, O, and P), removal of metals or metalloids, saturation of double bonds and/or aromatics by addition of hydrogen, isomerization of the carbon backbone to introduce branches to the backbone, and/or reforming to make aromatic compounds.

Upgrading can also comprise, for example, cracking (e.g. thermal cracking, catalytic cracking, dehydrogenation, dehydrocyclization, and heavy ends), hydrogenation (e.g. hydrocracking and hydrotreating), isomerization, alkylation, and polymerization (for example, as described Speight, J. G. (1991). Refining Chemistry. In H. Heinemann (Ed.). The Chemistry and Technology of Petroleum (pp. 473-497. New York: Marcel Dekker Press).

The following metals and metalloids are exemplary elements that can be removed from an oil composition using any of the methods and/or systems described herein: Boron (B); Calcium (Ca); Chromium Cr); Copper (Cu); Iron (Fe); Lead (Pb); Lithium (Li); Magnesium (Mg); Manganese (Mn); Nickel (Ni); Phosphorus (P); Potassium (K); Silicon (Si); Sodium (Na); Strontium (Sr); and Zinc (Zn).

Catalysts employing metals such as Ni/Mo, Co/Mo, and Ni/W on alumina, silica-alumina and silica supports can be promoted by additives such as phosphorus. Such catalysts are routinely used in the refining industry for hydrotreating and hydrocracking. They are available from catalyst suppliers such as Axens (France), UOP (USA). Albamarie (USA), and Criterion (Netherlands).

Other conventional catalysts can be used to further upgrade oils (e.g. algal oils) that are the products of HDM/HDS/HDN and/or HDO. These catalysts include catalytic cracking catalysts (FCC) such as Y-type zeolites in a silica-alumina matrix, isomerization and hydroisomerization catalysts consisting of supported noble metals (e.g. Pt and Pd) and naphtha reforming catalysts such as Pt supported on alumina. Base oil lube stock catalysts comprising various zeolites, and supports such as alumina. Noble metals can also be used in the catalysts. These catalysts are also available from many of the suppliers noted above and also companies such as Davison (USA) and Engelhard (USA).

Exemplary conditions for HDM, HDS, HDN and/or HDO are provided in the table below.

| | |
|---|---|
| Temperature | from about 315 to about 480 C. (from about 600 to about 900 F.) |
| Total pressure and/or hydrogen partial pressure | from about 100 to about 3000 psi |
| Hydrogen to oil ratio | from about 100 to about 2000 scf/Bbl (scf = standard cubic feet, Bbl = 42 gal) |
| Space velocity | from, about 1.5 to about 8 (space velocity is the ratio of the reactor charge rate in volumes per hour to the reactor volume) |

In another embodiment, a method for "upgrading" or refining an oil composition comprises catalytically removing, for example, nitrogen from an oil composition to create a refined oil composition, wherein the starting oil composition comprises greater than about 2.5% w/w nitrogen, greater than about 8% w/w oxygen or greater than about 0.1% w/w phosphorus. In some embodiments, a starting oil composition comprises greater than about 0.5% w/w nitrogen or chlorophyll/chlorophyllide and greater than about 5% w/w oxygen. In some embodiments, oxygen content in an oil composition can be partially accounted for by a large amount of triglycerides or fatty acids. An oil composition, extracted or derived from a biomass, may also have a significant amount of phosphorous (for example, from phospholipids) and other metals or metalloids. For example, an oil composition may comprise greater than about 0.1% w/w phosphorous and greater than about 0.5% nitrogen. In some embodiments, the oil composition comprises greater than 0.5, greater than 1, greater than 1.5, greater than 2, greater than 2.5, greater than 3, greater than 3.5, greater than 4, greater than 4.5, or greater than 5% w/w nitrogen. In some embodiments, the oil composition comprises greater than greater than 5, greater than 6, greater than 7, greater than 8, greater than 9, greater than 10, greater than 11, or greater than 12% w/w oxygen. In some embodiments, the oil composition comprises greater than 0.1, greater than 0.2, greater than 0.5, 1, or greater than 2% phosphorous. As described herein, in some embodiments, the oil composition has a different composition than crude petroleum. In one embodiment, the oil composition has a different composition than sweet crude. In some embodiments, the oil composition derived from biomass has a different composition than heavy and/or shale oil.

In one embodiment, the oil composition is derived from algae. FIG. 1 compares the content of an exemplary algal oil and an exemplary crude oil from fossil fuels. An oil composition derived from algae can comprise significant levels (for example, 1% to greater than 40%) of a variety of other oil or lipid components including, but not limited to, chlorophylls and/or chlorophyllides, isoprenoids and carotenoids, and phospholipids. For example, as demonstrated in FIG. 1, the algae oil has a nitrogen content of greater than about 0.5% up to 4% w/w. In addition, the algae oil has a higher content of oxygen as compared to crude oil (for example, 10-12% as compared to less than 0.1% w/w). Also, the algae oil has a higher phosphorous content as compared to crude oil (FIG.

1). These exemplary heteroatoms can be removed by the methods and systems described herein.

Presented below are exemplary ranges of various components of an algal oil composition obtained from 34 starting oil compositions.

| | Algae Oil - Starting Oil Composition |
|---|---|
| Carbon | 70.74-78.5% w/w |
| Hydrogen | 8.53-12.1% w/w |
| Nitrogen | 0.0528-4.8% w/w (0.676-61.44% w/w) |
| Oxygen | 6.81-15.64% w/w |
| Sulfur | 344-9000 ppm (0.0344-0.9% w/w) |
| Phosphorus | 6-8300 ppm (0.0006%-0.83% w/w) |

In another embodiment, a method for "upgrading" or refining an oil composition comprises catalytically removing heteroatoms from an oil composition to create a relined oil composition, wherein the starting oil composition comprises greater than about 0.05% w/w nitrogen, greater than about 6% w/w oxygen or greater than about 0.03% w/w sulfur.

In other embodiments, the starting oil composition comprises greater than about 0.05% to about 5.0% w/w nitrogen, greater than about 6% to about 16% w/w oxygen or greater than about 0.03% to about 1.0% w/w sulfur.

In other embodiments, the starting oil composition comprises greater than about 0.01% to about 10.0% w/w nitrogen, greater than about 3% to about 18% w/w oxygen or greater than about 0.01% to about 3.0% w/w sulfur.

In another embodiment, a method for "upgrading" or refining an oil composition comprises catalytically removing heteroatoms from an oil composition to create a refined oil composition, wherein the starting oil composition comprises greater than about 0.05% w/w nitrogen, greater than about 6% w/w oxygen or greater than about 0.0005% w/w phosphorus.

In other embodiments, the starting oil composition comprises at least one of the following four ranges: a phosphorus concentration of 0% to 5% w/w; a nitrogen concentration of 0% to 10% w/w; a sulfur concentration of 0% to 5% w/w; or an oxygen concentration of 0% to 20% w/w.

In some embodiments, an oil composition is derived from a biomass and contains a larger amount of heteroatoms than a fossil fuel oil composition. For example, often an oil composition extracted from a biomass contains biological molecules that contain heteroatoms such as chlorophyll, fatty acids, or phospholipids that are not found in a fossil fuel composition. Also, oil compositions derived from fossil fuels or biomass can comprise other metals or metalloid compounds. In another embodiment, the oil composition comprises a higher percentage of nitrogen (w/w) than shale oil.

In one embodiment, a method is disclosed for preparing a refined oil composition from an oil composition, comprising catalytically removing (i) metals or metalloids, (ii) nitrogen, and/or (iii) oxygen from an oil composition to create a refined composition. In one example, the catalytic removal of metals or metalloids comprises the absorption of the metals or metalloids onto the surface of a catalyst.

Metal Removal

In some embodiments, a method or system as described herein comprises two or three refining steps in series. One step can be hydrodemetallization (HDM), in which metals (for example, Mg and Na) and metalloids (for example, P) can be removed from an oil composition (obtained from a biomass) by absorption onto a catalyst. Because the metal or metalloid heteroatoms are absorbed onto a catalyst, often an HDM catalyst has a shorter lifetime than other reaction catalysts. In some embodiments, the lifespan and cost-effectiveness of a catalyst can be optimized by selecting a catalyst/support with a high surface area and pore volume, and by selecting an open pore structure to ensure maximum accessibility of the oil composition, along with the highest metal and metalloid storage capacity. Also, for example, a catalyst for hydrodemetallization can have high porosity and be able to sequester high levels of metals and metalloids. A catalyst can be recycled and reused in any of the methods and systems described herein.

The catalysts can comprise, for example, a support such as alumina (or aluminosilicates or sillies) and can also comprise two or more metal compounds such as Co/Mo, Ni/Mo, and/or W/Mo. In addition, the support may be a silica, silica-alumina, or alumina support. Other examples of catalysts include Ni/Mo on alumina promoted with phosphorus, Co/Mo on alumina, Ni/W on alumina. Exemplary manufactures of these products are Haldor Topsoe (Denmark). The supports (e.g. alumnia) can have different pore structures. The HDM catalyst can, for example, have larger macro and micro pores than an HDN or HDO catalyst.

The step(s) of removing a metal or metalloid can often require elevated temperatures (for example, about 300 to about 500° C.) and a high pressures of hydrogen (for example, greater than about 500 psi or greater than about 1000 psi). In some embodiments, a metal removing step can be carried out at a temperature of greater than 100, greater than 150, greater than 200, greater than 250, greater than 300, greater than 350, greater than 400, greater than 450, greater than 500, greater than 750, or greater than 1000° C. In some embodiments, a metal removing step can be carried out at a pressure of hydrogen of greater than 100, greater than 300, greater than 500, greater than ID greater than 1000, greater than 1500, or greater than 2000 psi.

In traditional petroleum refining processes, when heavy oil is hydrogenated, high levels of metals can inhibit catalytic activity when performing hydrodesulfurization (HDS). Furthermore, heavy metals such as nickel and vanadium in the heavy oil can deposit on the surfaces of the catalyst particles resulting in a decrease of catalyst activity. If this happens, the catalyst must be replaced with a fresh catalyst, HDS can remove not only sulfur, but some small amounts of metal heteroatoms (for example, as described in FIG. 4).

Other methods of removing metal from an oil composition may be used in combination with a method or system described herein. Other methods of removing metals include regeneration of the catalyst. For example, the Demet Process removes metals such as nickel and vanadium from a spent catalyst. The nickel and vanadium are converted to chlorides which are then washed out of the catalyst. Another exemplary method of removing metals is metal passivation, wherein materials can be used as additives which can be impregnated in a catalyst or added to the oil composition in the form of metal-organic compounds. Such materials can react with the metal contaminants and passivate the contaminants by forming less harmful compounds that remain on the catalyst. For example, antimony and bismuth are effective in passivating nickel, and tin is effective in passivating vanadium.

Nitrogen Removal

Hydrogenolysis is a chemical reaction whereby a carbon-carbon or carbon-heteroatom single bond is cleaved or undergoes lysis by hydrogen. The heteroatom may vary, but examples include oxygen, nitrogen, or sulfur. A related reaction is hydrogenation, where hydrogen is added to the molecule, without cleaving bonds. Usually hydrogenolysis is conducted catalytically using hydrogen gas. In petroleum refineries, catalytic hydrogenolysis of feedstocks is conducted on a large scale to remove sulfur from feedstocks, releasing gaseous hydrogen sulfide ($H_2S$). The hydrogen sulfide is subsequently recovered in an amine treater and finally converted to elemental sulfur. Hydrogenolysis can be accompanied by hydrogenation.

Product stability can also be affected by the presence of nitrogen-containing compounds in an oil composition. A hydrogenolysis reaction can be used to reduce the nitrogen content of a petroleum stream; in this case the reaction is called hydrodenitrogenation (HDN). Many HDS units for desulfurizing naphthas in petroleum refineries are actually simultaneously denitrogenating. HDN can be used as a method of removing nitrogen from an oil composition by creating ammonia or ammonium. In some embodiments, ammonia products can be recycled as nutrients for biomass growth.

HDN can often require elevated temperatures (for example, about 300 to about 500° C.) and high pressures of hydrogen (for example, greater than about 500 psi or even greater than about 1000 psi). In some embodiments, HDN can be carried out at a temperature of greater than 100, greater than 150, greater than 200, greater than 250, greater than 300, greater than 350, greater than 400, greater than 450, greater than 500, greater than 750, or greater than 1000° C. In some embodiments, HDN can be carried out at a pressure of hydrogen of greater than 100, greater than 300, greater than 500, greater than 750, greater than 1000, greater than 1500, or greater than 2000 psi.

The catalysts comprise, for example, a support such as alumina (or aluminosilicates or silics) and can also comprise two or more metal compounds such as Co/Mo, Ni/Mo, and/or W/Mo. In addition, the support may be a silica, silica-alumina, or alumina support. Other examples of catalysts include Ni/Mo alumina promoted with phosphorus, Co/Mo on alumina, Ni/W alumina. Exemplary manufactures of these products are Haldor Topsoe (Denmark). The supports (e.g. alumina) can have different pore structures. The HDM catalyst can, for example, have larger macro and micro pores than an HDN or HDO catalyst.

The presence of nitrogen in an oil composition can present many problems in that the nitrogen can interfere with the refining, the transportation, and/or the use of an oil composition. Exemplary deleterious effects brought about by the presence of nitrogen in an oil composition include, but are not limited to, a decreased catalyst life during hydrogenation, reforming, hydrocracking and catalytic cracking reactions, a decreased chemical stability of any resulting product, and a decreased color stability of any resulting product.

Another issue with the presence of nitrogen in an oil composition is that it is not desirable to transport nitrogen-containing oil through pipelines used for transporting petroleum products, because of the possible contamination of such petroleum products with residual nitrogen-containing oil in the pipeline. Generally, petroleum products transported in a pipeline do not contain a significant amount of nitrogen. Relatively high nitrogen content in an oil composition can pollute the pipelines making them undesirable and uneconomical for transporting such low nitrogen-containing petroleum products. In addition, high nitrogen content in an oil composition can cause clogging of pipelines due to self-polymerization brought about by the reactivity of the nitrogen-containing compounds. In addition, in some embodiments, due to the basicity of the nitrogen-containing compounds, some corrosion can occur, thus damaging a pipeline.

In some embodiments, enzymes (for example, chlorophyllase) can be added to an oil composition to break up nitrogen containing compounds or molecules. Other enzymes that can be used are, for example, a RCC reductase, a dechelatase, or a pheophorbide a oxygenase. Various chlorophyllases have been purified, cloned, and recombinantly expressed from photosynthetic organisms (for example, as described in U.S. Pat. No. 7,199,284) and any given one can be used in the systems or methods as disclosed herein. Exemplary biomass degrading enzymes are described in International Patent Application No. PCT/US2008/006879, filed May 30, 2008. Additional polypeptides and/or peptides, either recombinantly produced or produced and purified from natural sources, can have esterase activity similar to a chlorophyllase. These polypeptides and/or peptides can include catalytic antibodies, enzymes, and active sites of enzymes. Any chlorophyllase, chlase, or chlorophyll-chlorophyllido hydrolyase or polypeptide having a similar activity (e.g., chlorophyll-chlorophyllido hydrolyase 1 or chlase 1, or, chlorophyll-chlorophyllido hydrolyase 2 or chlase 2 (e.g., NCBI P59677-1 and P59678, respectively) can be used in a method or a system as disclosed herein. Any polypeptide (e.g., enzyme or catalytic antibody) that catalyses the hydrolysis of a chlorophyll or pheophytin ester bond to yield chlorophyllide and a phytol or pheophorbide and a phytol can be used in a method or a system as disclosed herein. Any isolated, recombinant, synthetic, or chimeric (e.g. a combination of synthetic and recombinant) polypeptide (e.g., enzyme or catalytic antibody) can be used, e.g., a chlorophyllase, chlase, or chlorophyll-chlorophyllido hydrolyase, or polypeptide having a similar activity can be used in a system or method as disclosed herein, (e.g., as described in Marchler-Bauer (2007) Nucleic Acids Res, 35:D237-40). Polypeptides and/or peptides having esterase (e.g., chlorophyllase) activity can be used in the systems or methods as disclosed herein.

Hydrodenitrogenation can be used to remove the nitrogen in the form of ammonia from an oil composition. Other methods of removing nitrogen from an oil composition have been developed and can be combined with any of the methods or systems described herein. Such developed methods are known to one of skill in the art.

In one embodiment, a method for preparing a fuel from an oil composition comprises: removing chlorophyll or chlorophyllide from an oil composition, and catalytically removing metals or metalloids and/or oxygen from the oil composition to create a refined composition. The biomass can be obtained from a green plant and therefore contains chlorophyll. Chlorophyll can be removed from an oil composition by using a solvent(s). Non-limiting examples of solvents and acids that can be used for nitrogen extraction include water, organic acids, or inorganic acids, such as, e.g., acetic acid, formic acid, citric acid, phosphoric acid, succinic acid, nitric acid, sulfuric acid, acetone, alcohols, glycerol, hexane, heptane, methylpentane, toluene, or methylisobutylketone, or any mixtures or salt solutions thereof. The methods and systems described herein can remove nitrogen and other heteroatoms associated with chlorophyll.

Oxygen Removal

Oxygen can also be removed by a method or system described herein. An exemplary method of removing oxygen is hydrodeoxygenation (HDO) which is the removal of oxygen by catalytic reaction with hydrogen. The resulting product can be a mixture of $H_2O$, CO, and/or $CO_2$. This reaction can be, for example, conducted with conventional fixed-bed bimetallic hydrotreating catalysts such as sulfided nickel-molybdenum (NiMo) or cobalt-molybdenum (CoMo) which are commonly used in refineries. In the HDO reaction, oxygen is removed as water, olefinic double bonds are hydrogenated, and sulfur and nitrogen compounds may be removed.

Exemplary catalysts can contain a metal of the Group VIII and/or VIA of the Periodic Table. The HDO catalyst can be a "supported" Pd, Pt, Ru, Rh, Ni, NiMo or CoMo catalyst, for example, the support being activated carbon, alumina and/or silica.

In some embodiments, any sulfur present can be removed through hydrodenitrogenation or hydrodeoxygenation as $H_2S$, and can then be collected in scrubbers.

HDO can often require elevated temperatures (for example, about 300 to about 500° C.) and high pressures of hydrogen (for example, greater than about 500 psi or even greater than about 1000 psi). In some embodiments, HDO can be carried out at a temperature of greater than 100, greater than 150, greater than 200, greater than 250, greater than 300, greater than 350, greater than 400, greater than 450, greater than 500, greater than 750, or greater than 1000 T. In some embodiments, HDO can be carried out at a pressure of hydrogen of greater than 100, greater than 300, greater than 500, greater than 750 greater than 1000, greater than 1500, or greater than 2000 psi.

Other methods of removing oxygen from an oil composition include methods for removing oxygen from chemical compositions. Exemplary methods of removing oxygen include, but are not limited to, Barton-McCombie deoxygenation and the Wolff-Kishner reduction.

Catalytic Reforming

The upgraded oil composition can, for example, be further treated by catalytic reforming. Catalytic reforming can be performed on an oil composition in combination with any one or more of the other methods disclosed herein. Catalytic reforming is a chemical process used to convert petroleum refinery naphthas, typically having low octane ratings, into high-octane liquid products called reformates which are components of high-octane gasoline (also known as petrol). Basically, the process re-arranges or re-structures the hydrocarbon molecules in the naphtha feedstocks as well as breaking some of the molecules into smaller molecules. The overall effect is that the product reformate contains hydrocarbons with more complex molecular shapes having higher octane values than the hydrocarbons in the naphtha feedstock. In so doing, the process separates hydrogen atoms from the hydrocarbon molecules and produces very significant amounts of byproduct hydrogen gas for use in a number of the other processes involved in a modern petroleum refinery. Other byproducts are small amounts of methane, ethane, propane and butanes.

Various catalyst reforming process have been developed all of which utilize a platinum and/or rhenium catalyst. For example, Rheniforming: Developed by Chevron Oil Company; Powerforming: Developed by Esso Oil Company, now known as ExxonMobil; Magnaforming: Developed by Englehard Catalyst Company and Atlantic Richfield Oil Company; Ultraforming: Developed by Standard Oil of Indiana, now a part of the British Petroleum Company; Houdriforming: Developed by the Houdry Process Corporation; CCR Platforming: A Platforming version, designed for continuous catalyst regeneration, developed by UOP; and Octanizing: A catalytic reforming version developed by Axens, a subsidiary of Institut francais du petrole (IFP), designed for continuous catalyst regeneration.

There are a good many chemical reactions that occur in the catalytic reforming process, all of which occur in the presence of a catalyst and a high partial pressure of hydrogen. Depending upon the type or version of catalytic reforming used as well as the desired reaction severity, the reaction conditions range from temperatures of about 495 to 525° C. and from pressures of about 5 to 45 atm (OSHA Technical Manual, Section IV, Chapter 2, *Petroleum Refining Processes*).

The commonly used catalytic reforming catalysts contain noble metals such as platinum and/or rhenium, which are very susceptible to poisoning by sulfur and nitrogen compounds. Therefore, the naphtha feedstock to a catalytic reformer is always pre-processed in a hydrodesulfurization unit which removes both the sulfur and the nitrogen compounds. The four major catalytic reforming reactions are described in, for example, Gary, J. H. and Handwerk, G. E. (1984) Petroleum Refining Technology and Economics (2nd Edition ed.) Marcel Dekker. Inc. ISBN 0-8247-7150-8.

The four major catalytic reforming reactions are:

1: The dehydrogenation of naphthenes to convert them into aromatics as exemplified in the conversion methylcyclohexane (a naphthene) to toluene (an aromatic), as shown below:

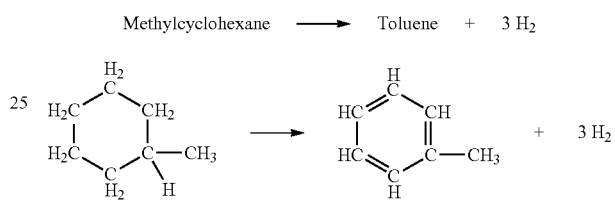

2: The isomerization of normal paraffins to isoparaffins as exemplified in the conversion of normal octane to 2,5-Dimethylhexane (an isoparaffin), as shown below:

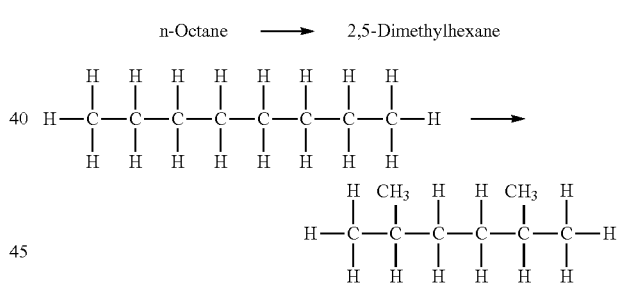

3: The dehydrogenation and aromatization of paraffins to aromatics (commonly called dehydrocyclization) as exemplified in the conversion of normal heptane to toluene, as shown below:

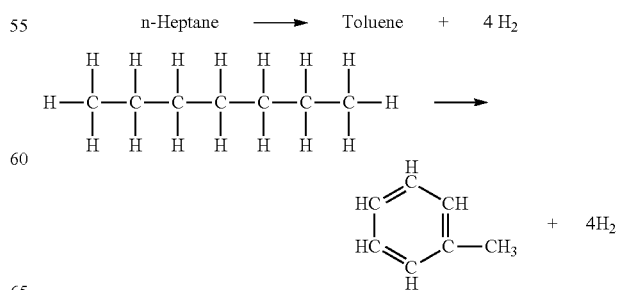

4: The hydrocracking of paraffins into smaller molecules as exemplified by the cracking of normal heptane into isopentane and ethane as shown below:

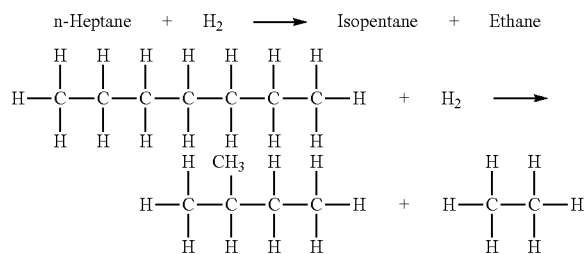

The hydrocracking of paraffins is the only one of the above four major reforming reactions that consumes hydrogen. The isomerization of normal paraffins does not consume or produce hydrogen. However, both the dehydrogenation of naphthenes and the dehydrocyclization of paraffins produce hydrogen. The overall net production of hydrogen in the catalytic reforming of petroleum naphthas ranges from about 50 to 200 cubic meters of hydrogen gas (at 0° C. and 1 atm) per cubic meter of liquid naphtha feedstock. In the United States customary units, that is equivalent to 300 to 1200 cubic feet of hydrogen gas (at 60° F. and 1 atm) per barrel of liquid naphtha feedstock (for example, as described in U.S. Pat. No. 5,011,805). In many petroleum refineries, the net hydrogen produced in catalytic reforming supplies a significant part of the hydrogen used elsewhere in the refinery (for example, hydrodesulfurization processes). The hydrogen is also necessary in order to hydrogenolyze any polymers that form on the catalyst.

The most commonly used type of catalytic reforming unit has three reactors, each with a fixed bed of catalyst, and all of the catalyst is regenerated in situ during routine catalyst regeneration shutdowns which occur approximately once each 6 to 24 months. Such a unit is referred to as a semi-regenerative catalytic reformer (SRR).

Some catalytic reforming units have an extra spare or swing reactor and each reactor can be individually isolated so that any one reactor can be undergoing in situ regeneration while the other reactors are in operation. When that reactor is regenerated, it replaces another reactor which, in turn, is isolated so that it can then be regenerated. Such units are referred to as cyclic catalytic reformers. Cyclic catalytic reformers serve to extend the period between required shutdowns.

One type of catalytic reformers are called continuous catalyst regeneration reformers (CCR). Such units are characterized by continuous in-situ regeneration of part of the catalyst in a special regenerator, and by continuous addition of the regenerated catalyst to the operating reactors. Two exemplary versions of CCR are UOP's CCR Platformer process (UOP LLC, Des Plaines Ill., USA) and Axen's Octanizing process (Axens IFP Group Technologies, Ruell-Malmaison, France). Many of the earlier catalytic reforming units are non-regenerative in that they did not perform in situ catalyst regeneration. Instead, when needed, the aged catalyst was replaced by fresh catalyst and the aged catalyst was shipped to catalyst manufacturer's to be either regenerated or to recover the platinum content of the aged catalyst.

The liquid feed (at the bottom left in the diagram) is pumped up to the reaction pressure (5 to 45 atm) and is joined by a stream of hydrogen-rich recycle gas. The resulting liquid-gas mixture is preheated by flowing through a heat exchanger. The preheated feed mixture is then totally vaporized and heated to the reaction temperature (495 to 520° C.) before the vaporized reactants enter the first reactor. As the vaporized reactants flow through the fixed bed of catalyst in the reactor, the major reaction is the dehydrogenation of naphthenes to aromatics (as described earlier herein) which is highly endothermic and results in a large temperature decrease between the inlet and outlet of the reactor. To maintain the required reaction temperature and the rate of reaction, the vaporized stream is reheated in the second fired heater before it flows through the second reactor. The temperature again decreases across the second reactor and the vaporized stream must again be reheated in the third fired heater before it flows through the third reactor. As the vaporized stream proceeds through the three reactors, the reaction rates decrease and the reactors therefore become larger. At the same time, the amount of reheat required between the reactors becomes smaller. Usually, three reactors are all that is required to provide the desired performance of the catalytic reforming unit.

Some installations use three separate fired heaters as shown in the schematic diagram and some installations use a single fired heater with three separate heating coils. The hot reaction products from the third reactor are partially cooled by flowing through the heat exchanger where the feed to the first reactor is preheated and then flow through a water-cooled heat exchanger before flowing through the pressure controller (PC) into the gas separator.

Most of the hydrogen-rich gas from the gas separator vessel returns to the suction of the recycle hydrogen gas compressor and the net production of hydrogen-rich gas from the reforming reactions is exported for use in the other refinery processes that consume hydrogen (such as hydrodesulfurization units and/or a hydrocracker unit).

The liquid from the gas separator vessel is routed into a fractionating column commonly called a stabilizer. The overhead offgas product from the stabilizer contains the byproduct methane, ethane, propane and butane gases produced by the hydrocracking reactions as explained in the above discussion of the reaction chemistry of a catalytic reformer, and it may also contain some small amount of hydrogen. That offgas is routed to the refinery's central gas processing plant for removal and recovery of propane and butane. The residual gas after such processing becomes part of the refinery's fuel gas system.

The bottoms product from the stabilizer is the high-octane liquid reformate that will become a component of the refinery's product gasoline.

Many catalytic reforming catalysts contain platinum or rhenium on a silica or silica-alumina support base, and some contain both platinum and rhenium. Fresh catalyst can be chlorided (chlorinated) prior to use.

The noble metals (platinum and rhenium) are considered to be catalytic sites for the dehydrogenation reactions and the chlorinated alumina provides the acid sites needed for isomerization, cyclization and hydrocracking reactions (for example, as described in Gary, J. H. and Handwerk, G. E. (1984) Petroleum Refining Technology and Economics (2nd Edition ed.). Marcel Dekker. Inc, ISBN 0-8247-7150-8).

The activity (i.e., effectiveness) of the catalyst in a semi-regenerative catalytic reformer is reduced over time during operation by carbonaceous coke deposition and chloride loss. The activity of the catalyst can be periodically regenerated or restored by in situ high temperature oxidation of the coke followed by chlorination. As stated earlier herein, semi-regenerative catalytic reformers are regenerated about once per 6 to 24 months.

Normally, the catalyst can be regenerated perhaps 3 or 4 times before it must be returned to the manufacturer for reclamation of the valuable platinum and/or rhenium content (for example, as described in Gary, J. H. and Handwerk, G. E. (1984) Petroleum Refining Technology and Economics (2nd Edition ed.). Marcel Dekker. Inc. ISBN 0-8247-7150-8).

Systems

Figure 3:
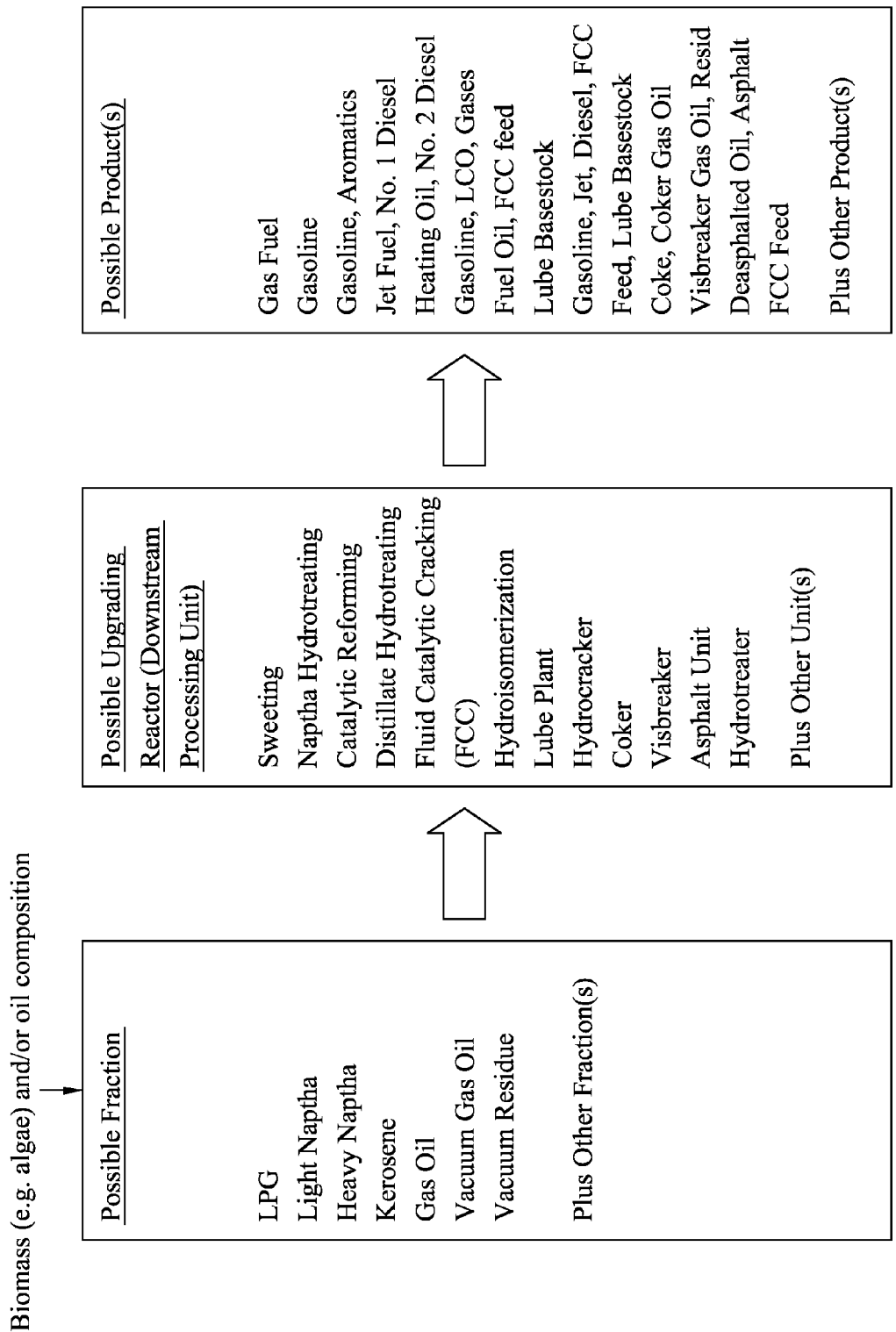
FIG. 3 shows an overview of the processes that can be involved in the production of a product obtained from a biomass and/or oil composition, specifically possible fractions, possible upgrading techniques, and possible products.
Figure 4:
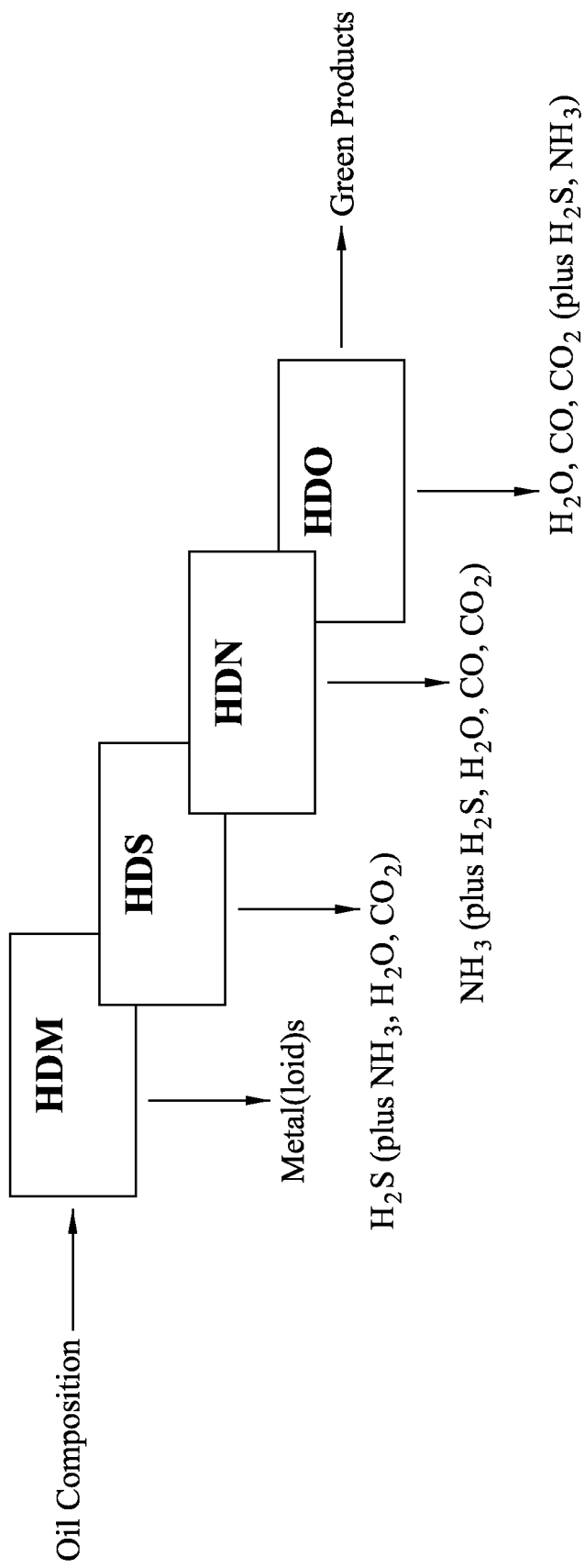
FIG. 4 shows exemplary methods and systems as described herein comprising hydrodemetallization (HDM), hydrodesulfurization (HDS), hydrodenitrogenation (HDN), and hydrodeoxygenation (HDO).

FIGS. 2 and 3 show exemplary that a biomass or oil composition can undergo to obtain a product. FIG. 4 shows exemplary configurations of various reactions that can occur in the methods and/or systems described herein. The oil composition can undergo any one or any combination of a HDM reaction, a HDS reaction, a HDN reaction, or a HDO reaction. The reactions can overlap, and/or can occur sequentially, and/or can occur simultaneously. For example, the HDM reaction can occur prior to the HDS, HDN, and HDO reactions. Another example is the HDM reaction occurring first, then the HDS and HDN reactions occurring simultaneously, then the HDO reaction. Additionally, all four reactions can occur simultaneously. The rates of the reactions can be controlled, for example, by pressure and temperature. One of skill in the art would be able to adjust these parameters to obtain the desired reactions and products. The Green Products can be, for example, light hydrocarbons, naphtha (gasoline), distillates (jet, diesel), gas oils, residuum, green distillates, green fuel products, and/or any of the products described herein.

Each reactor comprises at least one catalyst. A reactor can comprise two or more catalysts.

In some embodiments, a system as described herein can contain a catalyst placed in, for example, a fixed bed reactor and/or a fluidized bed reactor. An oil composition to be treated can be introduced into the reactor and treated at a high temperature and pressure under the desired hydrogen partial pressure to carry out removal of metal, oxygen, and/or nitrogen. The catalyst may be put into a single reactor or plural reactors successively connected. In some embodiments, one or more other hydrogenation/hydrogenolysis catalysts may be packed into a single reactor. In addition, organometallic compounds and other metal components contained in an oil composition often deposit on a catalyst in the form of, for example, metal sulfides. In some embodiments, the metal or metalloid is removed using a method described herein before the removal of nitrogen or oxygen.

In an embodiment, a system is described for preparing an oil composition for refining that comprises: a metal-removing reactor comprising a metal-removing catalyst configured to remove metal or metalloid atoms from an oil composition; and a nonmetal-removing reactor comprising a nonmetal-removing catalyst configured to remove at least one of nitrogen or oxygen from the oil composition, wherein the nonmetal-removing reactor is in fluidic communication with the metal-removing reactor. A metal-removing catalyst can be, for example, a catalyst onto which a metal or metalloid can be absorbed. A nonmetal-removing catalyst can be, for example, a catalyst that breaks the bonds of a molecule containing a heteroatom, such as a nitrogen, oxygen, or sulfur atom.

In an exemplary system, a system can comprise two parallel catalyst beds (for example, one active online and the second packed with fresh catalyst) that can be switched or alternated according to the activity of the catalyst. In another exemplary system, a system can comprise three beds in which one is inline with the refining system and active, a second which is being filled with fresh catalyst, and a third which is being emptied and refilled. The systems or methods herein can be modified as would be apparent to one skilled in the art for different metal and metalloid levels in an oil composition and/or oil composition flow rates through the system.

A system can further comprise a first metal-removing reactor in parallel with a second metal-removing reactor, wherein the first metal-removing reactor is interchangeable with the second metal-removing reactor. For example, a system can comprise a plurality of reactors in series each comprising a metal-removing reactor. With a system comprising two or more metal-removing reactors the catalyst in one of the two reactors can be serviced while the other reactor remains online. For example, a catalyst can be removed and replaced without slowing the operation of the system as a whole. Two or more metal-removing reactors can improve the cost-effectiveness of the system.

In some embodiments, a system further comprises: a third metal-removing reactor in parallel and interchangeable with the second metal-removing reactor and the first metal-removing reactor, wherein when one of the metal-removing reactors is in operation, another metal-removing reactor is on stand-by and comprises unused metal-removing catalyst, and the final metal-removing reactor is being emptied and/or refilled with unused metal-removing catalyst.

In some embodiments, the metal-removing catalyst has an open pore structure to ensure maximum access of the oil composition and the highest metal and metalloid storage capacity. A metal-removing catalyst comprises, for example, a support of alumina, aluminosilicate, and/or aluminosilic, and Co/Mo, Ni/Mo, and/or W/Mo. Exemplary supports of a metal-removing (for example, hydrodemetallizing) catalyst for a oil composition described herein include, but are not limited to, alumina, silica, silica-alumina, titania, magnesia and silica-magnesia. Hydrodemetallization can be carried out in a fixed bed system. A reactor of a system here can be either a single-stage or a multistage reactor.

In the process of removing heteroatoms from oil compositions, generally, the type (for example, active metal species and amount of carried metals) of catalyst to be packed in the reactor and the amount of packed catalyst can be determined based on a condition that the catalyst would effectively function throughout the packed bed during the period of one cycle of continuous operation.

In some embodiments, a system further comprises a second nonmetal-removing reactor configured to remove at least one of nitrogen or oxygen from the oil composition, wherein the second nonmetal-removing reactor is in fluidic communication with the first nonmetal-removing reactor.

A nonmetal-removing catalyst can comprise, for example, a support of alumina, aluminosilicate, and/or aluminosilic, and Co/Mo, Ni/Mo, and/or W/Mo.

A catalyst composition can be, for example, a hydrogenation catalyst comprising an active component for hydrogenation supported on a carrier. A catalyst composition can also be, for example, a hydrogenation catalyst composed of metals of Group VIb and/or Group VIII of the Periodic Table supported on a porous refractory oxide carrier. Examples of porous refractory oxides include alumina, silica, magnesia, silica-magnesia, zirconia, silica-zirconia, titania and silica-titania. In some embodiments, alumina or silica-alumina is used.

Any conventional catalytically active ingredient(s) for hydrogenation can be used as the active metal of a hydrogenation catalyst to be supported on the porous refractory oxide. For example, there can be used at least one member selected from the group consisting of metals (for example, chromium, molybdenum, and tungsten) of Group VIb of the Periodic Table or the compounds of these metals, and/or the metals (for example, iron, cobalt, nickel, platinum) of Group VIII of the Periodic Table or the compounds of these metals.

Catalysts described herein can be prepared by conventional methods. The alumina carrier can be prepared by neutralizing an acidic aluminum salt such as aluminum sulfate or aluminum nitrate with a base such as ammonia, or neutralizing an aluminate such as sodium aluminate with an acidic aluminum salt or an acid, washing the resulting gel and carrying out conventional treatments such as heating, aging, molding, drying and calcining.

Although the catalyst may be randomly packed in the hydrogenation apparatus, a large columnar catalyst can, for example, be aligned with its end faces confronting the direction of flow of the reaction fluid.

In some embodiments, a system is in fluidic communication with an oil pipeline. In some embodiments, a system can further comprise a distilling device in fluidic communication with the oil pipeline wherein the distilling device is configured to remove hydrocarbons that are C4 hydrocarbons or smaller from the oil composition.

In some examples, the light hydrocarbons (for example, propane originating from triglycerides (glycol) in a refined composition that are removed can be a separate product. In some embodiments, the light hydrocarbons can be used as a fuel to heat or process a system or method as described herein. Exemplary light hydrocarbons include, but are not limited to, methane, ethane, propane, and butane.

Oil Refining

In some embodiments, a refined or "upgraded" composition can be similar (for example, have a low sulfur content and the same hydrocarbon constituents) to a sweet crude stream of a petroleum based fuel. When produced at commercial scale, it may be economically desirable to transport the refined composition by pipeline rather than truck, rail or ship. The refined composition can, for example, be shipped by pipeline and further processed using current standard refining technologies or future refining technologies, to create fuels and chemicals.

Crude petroleum oil is transported by pipeline and by traditional transportation, such as trucks. As described herein, some biofuels can contain too high a concentration of heteroatoms to transport in a traditional crude petroleum oil pipeline. A method or system as described herein can be used to upgrade, for example, remove heteroatoms from an oil composition derived/extracted from a biomass, allowing the fuel to be transported in a pipeline. A pipeline can be a pipeline designed for biofuel or a traditional petroleum crude oil pipeline.

In some embodiments, a method as described herein can further comprise refining the refined or "upgraded" composition, for example, catalytically cracking the refined composition.

The method(s) used to refine an oil composition or an upgraded oil composition can be chosen to optimize the types, shapes, and sizes of the hydrocarbon mixture desired in the resulting fuel product. Typical refining processes in the fuel industry include, but are not limited to, distillation, fractionation, extraction, solvent extraction, hydrotreatment, isomerization, dimerization, alkylation, and cracking. A cracking process typically refers to a process that breaks down hydrocarbons into smaller hydrocarbons, for example, by scission of a carbon-carbon bond. Complex organic molecules such as isoprenoids or heavy hydrocarbons can be cracked into simpler molecules (for example, light hydrocarbons) by the breaking of a portion of the carbon-carbon bonds in the complex organic molecules. Cracking is commonly performed using high temperatures, catalysts, or a combination thereof. Examples of cracking methods include, but are not limited to, thermal cracking, fluid catalytic cracking, thermoform catalytic cracking, catalytic cracking, steam cracking, and hydrocracking.

In some embodiments, a system of removing heteroatoms from an oil composition can be part of a filet refining system. In other embodiments, the system of removing heteroatoms is not part of a fuel refining system. In another embodiment, a system of removing heteroatoms from an oil composition is in communication with or delivers the oil composition to a refinery or other fuel refining system.

Catalytic cracking processes can involve scission of an organic molecule in the presence of a catalyst, for example, an acid catalyst such as a silica-alumina catalyst or a zeolite. Catalysts promote a heterolytic (asymmetric) breakage of bonds yielding pairs of ions of opposite charges, for example, a carbocation and a very unstable hydride anion. Carbon-localized free radicals and cations are both highly unstable and can undergo a process of chain rearrangement, for example a C-C scission in the beta position, and/or an intra- or intermolecular hydrogen transfer or hydride transfer, in these processes, the corresponding reactive intermediates (for example, radicals and ions) are permanently regenerated, and thus the reaction can proceed by a self-propagating chain mechanism. The chain of reactions can then be eventually terminated by a radical or an ion recombination.

In some embodiments, a method as disclosed herein can further comprise a catalytic cracking process. For example, an oil composition derived from a biomass can have metal, phosphorous, sulfur, nitrogen, and/or oxygen atoms completely or partially removed, and then be catalytically cracked.

Figure 5:
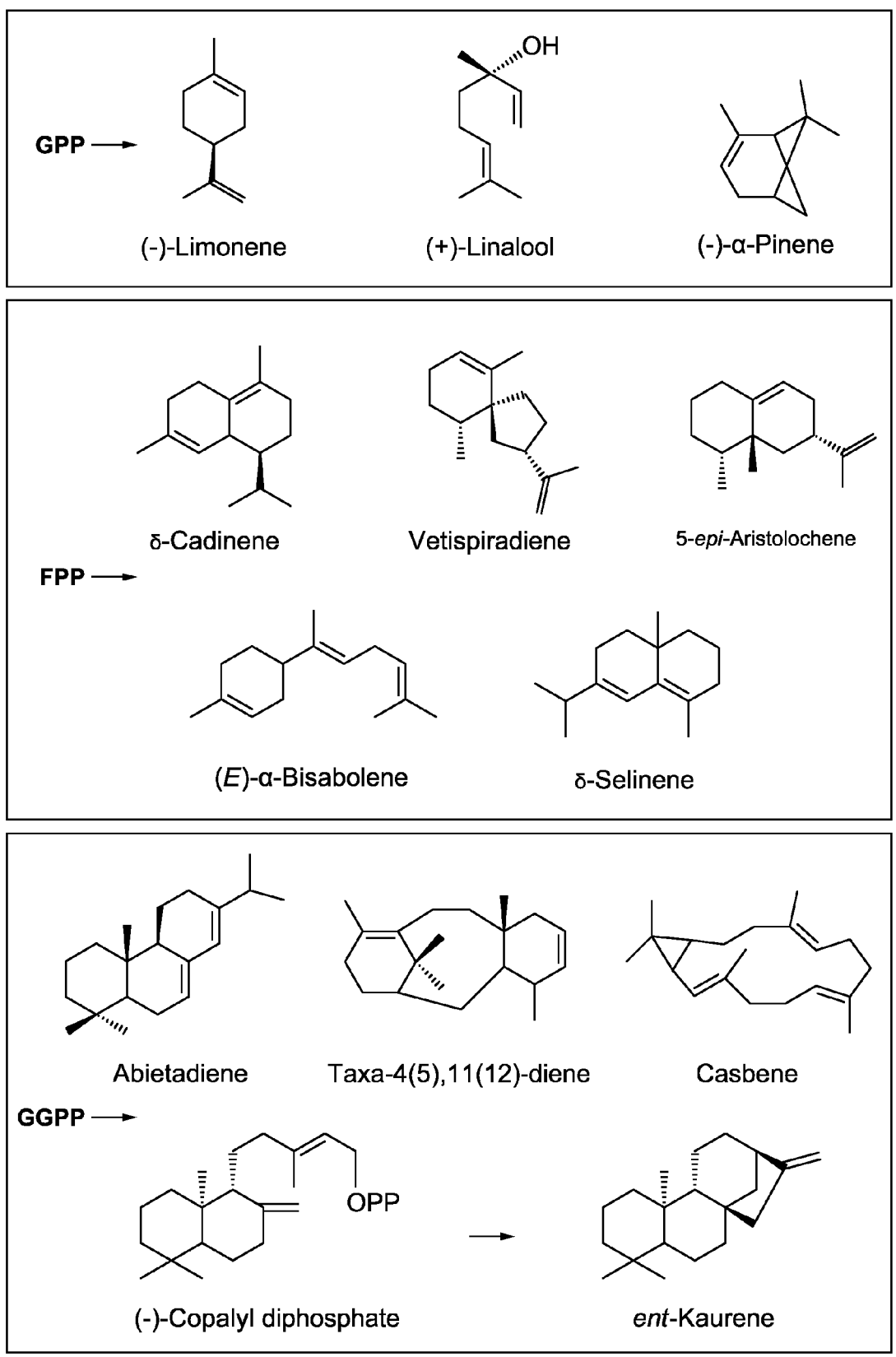
FIG. 5 shows examples of terpenes that can be obtained from a biomass.

In some embodiments, the oil composition comprises terpenes that can be cracked into fuel components. Terpenes area large and varied class of hydrocarbons, produced by a wide variety of organisms, for example, photosynthetic organisms. The term terpene can be used to describe both terpenoids or isoprenoids. Terpenes are the primary constituents of the essential oils of many types of plants and flowers. Essential oils are used widely as natural flavor additives for food, as fragrances in perfumery, and in traditional and alternative medicines such as aromatherapy. Synthetic variations and derivatives of natural terpenes also greatly expand the variety of aromas used in perfumery and flavors used in food additives. Table 1 and FIG. 5 show exemplary terpenes that can be found in an oil composition. Isomers of the compounds shown in Table 1 and FIG. 5 can also be found in an oil composition.

TABLE 1

| Name | Structure | Size | CAS | MW |
|---|---|---|---|---|
| Isoprene | 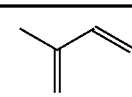 | 5 | | 68.1 |

TABLE 1-continued

| Name | Structure | Size | CAS | MW |
|---|---|---|---|---|
| Myrcene | 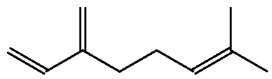 | 10 | | 136.2 |
| Ocimene | 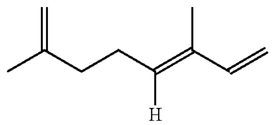 | 10 | 13877-91-3 | 136.2 |
| Limonene | 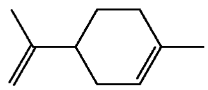 | 10 | | 136.2 |
| Terpinolene | 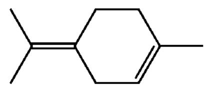 | 10 | 586-62-9 | 136.2 |
| Phellandrene | 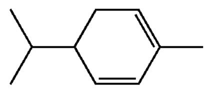 | 10 | 99-83-2 | 136.2 |
| Farnesene | 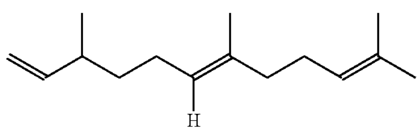 | 15 | | 204.3 |
| Cuparene | 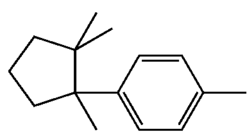 | 15 | | 202.3 |
| Cuprenene | 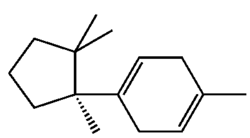 | 15 | 5046-93-5 | 204.4 |
| Isobazzanene | 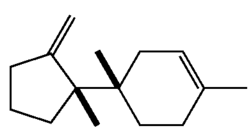 | 15 | 88661-59-0 | |
| Sesquiphellandrene | 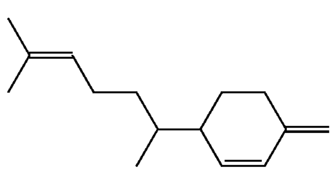 | 15 | 20307-83-9 | 204.4 |
| Bisabolene | 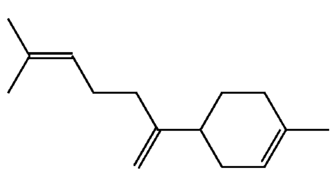 | 15 | 495-61-4 | 204.3 |
| Curcumene | 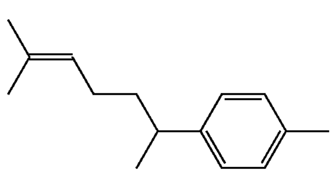 | 15 | 28976-68-3 | 202.3 |

TABLE 1-continued

| Name | Structure | Size | CAS | MW |
|---|---|---|---|---|
| Zingiberene | 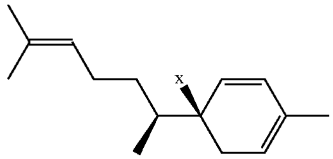 | 15 | 495-60-3 | 204.3 |
| Barbatene | 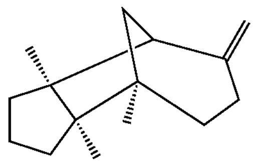 | 15 | 53060-59-6 | 204.3 |
| Fusicocca-2,10(14)-diene | 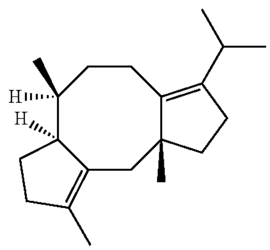 [SMILES: CC1=C2C[C@@]3(C)CCC(C(C)C)=C3CC[C@H](C)[C@@H]2CC1] | 20 | | 272.47 |

Hydrocarbon Production

Any of the products described herein can be obtained by transforming an organism with a polynucleotide resulting in the production of the desired product. Some of the products are naturally produced by an organism and their production can be manipulated by transforming an organism with a polynucleotide resulting in the increased or altered production of the product.

Host Cells or Host Organisms

Biomass useful in the methods and systems described herein can be obtained from host cells or host organisms.

A host cell can contain a polynucleotide encoding a polypeptide of the present disclosure. In some embodiments, a host cell is part of a multicellular organism. In other embodiments, a host cell is cultured as a unicellular organism.

Host organisms can include any suitable host, for example, a microorganism. Microorganisms which are useful for the methods described herein include, for example, photosynthetic bacteria (e.g., cyanobacteria), non-photosynthetic bacteria (e.g., *E. coli*), yeast (e.g., *Saccharomyces cerevisiae*), and algae (e.g., microalgae such as *Chlamydomonas reinhardtii*).

Examples of host organisms that can be transformed with a polynucleotide of interest include vascular and non-vascular organisms. The organism can be prokaroytic or eukaryotic. The organism can be unicellular or multicellular. A host organism is an organism comprising a host cell. In other embodiments, the host organism is photosynthetic. A photosynthetic organism is one that naturally photosynthesizes (e.g., an alga) or that is genetically engineered or otherwise modified to be photosynthetic. In some instances, a photosynthetic organism may be transformed with a construct or vector of the disclosure which renders all or part of the photosynthetic apparatus inoperable.

By way of example, a non-vascular photosynthetic microalga species (for example, *C. reinhardtii*, *Nannochloropsis oceania*, *N. salina*, *D. salina*, *H. pluvalis*, *S. dimorphus*, *D. viridis*, and *D. tertiolecta*) can be genetically engineered to produce a terpene or terpenoid. Production of a terpene or terpenoid in these microalgae can be achieved by engineering the microalgae to express a protein or enzyme in the algal chloroplast or nucleus.

The host cell can be prokaryotic. Examples of some prokaryotic organisms of the present disclosure include, but are not limited to, cyanobacteria (e.g., *Synechococcus*, *Synechocystis*, *Athrospira*). Suitable prokaryotic cells include, but are not limited to, any of a variety of laboratory strains of *Escherichia coli.*, *Lactobacillus* sp., *Salmonella* sp., and *Shigella* sp. (for example, as described in Carrier et al. (1992) J. Immunol. 148:1176-1181; U.S. Pat. No. 6,447,784; and Sizemore et al. (1995) Science 270:299-302). Examples of *Salmonella* strains which can be employed in the present disclosure include, but are not limited to, *Salmonella typhi* and *S. typhimurium*. Suitable *Shigella* strains include, but are not limited to, *Shigella flexneri*, sonnei, and *Shigella disenteriae*. Typically, the laboratory strain is one that is non-pathogenic. Non-limiting examples of other suitable bacteria include, but are not limited to, *Pseudomonas pudita*, *Pseudomonas aeruginosa*, *Pseudomonas mevaionii*, *Rhodobacter sphaeroides*, *Rhodobacter capsulatus*, *Rhodospirillum rubrum*, and *Rhodococcus* sp.

In some embodiments, the host organism is eukaryotic (e.g. green algae, red algae, brown algae). Suitable eukaryotic host cells include, but are not limited to, yeast cells, insect cells, plant cells, fungal cells, and algal cells. Suitable eukaryotic host cells include, but are not limited to, *Pichia pastoris*, *Pichia fintandica*, *Pichia trehalophila*, *Pichia kociarnae*, *Pichia membranaefaciens*, *Pichia opuntiae*, *Pichia thermototerans*, *Pichia salictaria*, *Pichia guercuum*, *Pichia pijperi*, *Pichia stiptis*, *Pichia methanolica*, *Pichia* sp., *Saccharomyces cerevisiae*, *Saccharomyces* sp., *Hansenula polymorpha*, *Kluyveromyces* sp., *Kluyveromyces lactis*, *Candida albicans*, *Aspergillus nidulans*, *Aspergillus niger*, *Aspergillus oryzae*, *Trichoderma reesei*, *Chrysosporium lucknowense*, *Fusarium* sp., *Fusarium gramineum*, *Fusarium venenatum*, *Neurospora crassa*, and *Chlamydomonas reinhardtii*. In other embodiments, the host cell is a microalga (e.g., *Chlamydomonas reinhardtii, Dunaliella salina, Haematococcus pluvialis, Nannochloropsis oceania, N. salina, Scenedesmus dimorphus, Chlorella* spp., *D. viridis*, or *D. tertiolecta*).

In some instances a host organism is vascular and photosynthetic. Examples of vascular plants include, but are not limited to, angiosperms, gymnosperms, rhyniophytes, or other tracheophytes. A further example of a vascular plant is from the genus team (e.g. duckweed).

In some instances a host organism is non-vascular and photosynthetic. As used herein, the term "non-vascular photosynthetic organism," refers to any macroscopic or microscopic organism, including, but not limited to, algae, cyanobacteria and photosynthetic bacteria, which does not have a vascular system such as that found in vascular plants. Examples of non-vascular photosynthetic organisms include bryophtyes, such as marchantiophytes or anthocerotophytes. In some instances the organism is a cyanobacteria. In some instances, the organism is algae (e.g., macroalgae or microalgae). The algae can be unicellular or multicellular algae. For example, the microalgae *Chlamydomonas reinhardtii* may be transformed with a vector, or a linearized portion thereof, encoding one or more proteins of interest (e.g., an isoprenoid synthase).

Methods for algal transformation are described in U.S. Provisional Patent Application No. 60/142,091. The methods of the present disclosure can be carried out using algae, for example, the microalga, *C. reinhardtii*. The use of microalgae to express a polypeptide or protein complex according to a method of the disclosure provides the advantage that large populations of the microalgae can be grown, including commercially (Cyanotech Corp.; Kailua-Kona HI), thus allowing for production and, if desired, isolation of large amounts of a desired product.

The vectors of the present disclosure may be capable of stable or transient transformation of multiple photosynthetic organisms, including, but not limited to, photosynthetic bacteria (including cyanobacteria), cyanophyta, prochlorophyta, rhodophyta, chlorophyta, heterokontophyta, tribophyta, glaucophyta, chlorarachniophytes, euglenophyta, euglenoids, haptophyta, chrysophyta, cryptophyta, cryptomonads, dinophyta, dinalagellata, pyrmnesiophyta, bacillariophyta, xanthophyta, eustigmatophyta, raphidophyta, phaeophyta, and phytoplankton. Other vectors of the present disclosure are capable of stable or transient transformation of, for example, *C. reinhardtii, N. oceania, N. salina, D. salina, H. pluvalis, S. dimorphus, D. viridis*, or *D. tertiolecta*.

Examples of appropriate hosts, include but are not limited to: bacterial cells, such as *E. colli, Streptomyces, Salmonella typhimurium*; fungal cells, such as yeast; insect cells, such as *Drosophila* S2 and *Spodoptera* Sf9; animal cells, such as CHO, COS or Bowes melanoma; adenoviruses; and plant cells. The selection of an appropriate host is deemed to be within the scope of those skilled in the art.

Polynucleotides selected and isolated as described herein are introduced into a suitable host cell. A suitable host cell is any cell which is capable of promoting recombination and/or reductive reassortment. The selected polynucleotides can be, for example, in a vector which includes appropriate control sequences. The host cell can be, for example, a higher eukaryotic cell, such as a mammalian cell, or a lower eukaryotic cell, such as a yeast cell, or the host cell can be a prokaryotic cell, such as a bacterial cell. Introduction of a construct (vector) into the host cell can be effected by, for example, calcium phosphate transfection, DEAE-Dextran mediated transfection, or electroporation.

Recombinant polypeptides, including protein complexes, can be expressed in plants, allowing for the production of crops of such plants and, therefore, the ability to conveniently produce large amounts of a desired product. Accordingly, the methods of the disclosure can be practiced using any plant, including, for example, microalga and macroalgae, (such as marine algae and seaweeds), as well as plants that grow in soil.

The term "plant" is used broadly herein to refer to a eukaryotic organism containing plastids, such as chloroplasts, and includes any such organism at any stage of development, or to part of a plant, including a plant cutting, a plant cell, a plant cell culture, a plant organ, a plant seed, and a plantlet. A plant cell is the structural and physiological unit of the plant, comprising a protoplast and a cell wall. A plant cell can be in the form of an isolated single cell or a cultured cell, or can be part of higher organized unit, for example, a plant tissue, plant organ, or plant. Thus, a plant cell can be a protoplast, gamete producing cell, or a cell or collection of cells that can regenerate into a whole plant. As such, a seed, which comprises multiple plant cells and is capable of regenerating into a whole plant, is considered plant cell for purposes of this disclosure. A plant tissue or plant organ can be a seed, protoplast, callus, or any other groups of plant cells that is organized into a structural or functional unit. Particularly useful parts of a plant include harvestable parts and parts useful for propagation of progeny plants. A harvestable part of a plant can be any useful part of a plant, for example, flowers, pollen, seedlings, tubers, leaves, stems, fruit, seeds, and roots. A part of a plant useful for propagation includes, for example, seeds, fruits, cuttings, seedlings, tubers, and rootstocks.

A method of the disclosure can generate a plant containing genomic DNA (for example, a nuclear and/or plastid genomic DNA) that is genetically modified to contain a stably integrated polynucleotide (for example, as described in Hager and Bock. Appl. Microbiet. Biotechnol. 54:302-310, 2000). Accordingly, the present disclosure further provides a transgenic plant, e.g. *C. reinhardtii*, which comprises one or more chloroplasts containing a polynucleotide encoding one or more exogenous or endogenous polypeptides, including polypeptides that can allow for secretion of fuel products and/or fuel product precursors (e.g., isoprenoids, fatty acids, lipids, triglycerides). A photosynthetic organism of the present disclosure comprises at least one host cell that is modified to generate, for example, a fuel product or a fuel product precursor.

Some of the host organisms useful in the disclosed embodiments are, for example, are extremophiles, such as hyperthermophiles, psychrophiles, psychrotrophs, halophiles, barophiles and acidophiles. Some of the host organisms which may be used to practice the present disclosure are halophilic (e.g., *Dunaliella salina, D. viridis*, or *D. tertiolecta*). For example, *D. salina* can grow in ocean water and salt lakes (for example, salinity from 30-300 parts per thousand) and high salinity media (e.g., artificial seawater medium, seawater nutrient agar, brackish water medium, and seawater medium). In some embodiments of the disclosure, a host cell comprising a vector of the present disclosure can be grown in a liquid environment which is, for example, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3 molar or higher concentrations of sodium chloride. One of skill in the art will recognize that other salts (sodium salts, calcium salts, potassium salts, or other salts) may also be present in the liquid environments.

Where a halophilic organism is utilized for the present disclosure, it may be transformed with any of the vectors described herein. For example, *D. salina* may be transformed with a vector which is capable of insertion into the chloroplast or nuclear genome and which contains nucleic acids which encode an isoprenoid producing enzyme (e.g., synthase, zingibererte synthase, squalene synthase). Transformed halophilic organisms may then be grown in high-saline environments (e.g., salt lakes, salt ponds, and high-saline media) to produce the products (e.g., isoprenoids) of interest. Isolation of the products may involve removing a transformed organism from a high-saline environment prior to extracting the product from the organism. In instances where the product is secreted into the surrounding environment, it may be necessary to desalinate the liquid environment prior to any further processing of the product.

A host organism may be grown under, conditions which permit photosyn hesis, however, his is not a requirement (e.g., a host organism may be grown in the absence of light). In some instances, the host organism may be genetically modified in such a way that photosynthetic capability is diminished and/or destroyed (see examples below). In growth conditions where a host organism is not capable of photosynthesis (e.g., because of the absence of light and/or genetic modification), typically, the organism will be provided with the necessary nutrients to support growth in the absence of photosynthesis. For example, a culture medium in (or on which an organism is grown, may be supplemented with any required nutrient, including an organic carbon source, nitrogen source, phosphorous source, vitamins, metals, lipids, nucleic acids, micronutrients, and/or an organism-specific requirement. Organic carbon sources include any source of carbon which the host organism is able to metabolize including, but not limited to, acetate, simple carbohydrates (e.g., glucose, sucrose, lactose), complex carbohydrates (e.g., starch, glycogen), proteins, and lipids. One of skill in the art will recognize that not all organisms will be able to sufficiently metabolize a particular nutrient and that nutrient mixtures my need to be modified from one organism to another in order to provide the appropriate nutrient mix.

A host organism may also be grown on land, e.g. In some cases, host organism(s) are grown near ethanol production plants or other facilities or regions (e.g., cities and highways) generating CO2. As such, the methods herein contemplate business methods for selling carbon credits to ethanol plants or other facilities or regions generating CO2 while making fuels or fuel products by growing one or more of the modified organisms described herein near the ethanol production plant.

Further, the organisms may be grown in outdoor open water, such as ponds, the ocean, sea, rivers, waterbeds, marsh water, shallow pools, lakes, and reservoirs. When grown in water, the organisms can be contained in a halo like object comprising of lego-like particles. The halo object encircles the algae and allows it to retain nutrients from the water beneath while keeping it in open sunlight.

In some instances, organisms can be grown in containers wherein each container comprises 1 or 2 or a plurality of organisms. The containers can be configured to float on water. For example, a container can be filled by a combination of air and water to make the container and the host organism(s) in it buoyant. A host organism that is adapted to grow in fresh water can thus be grown in salt water (i.e., the ocean) and vice versa. This mechanism allows for automatic death of the organism if there is any damage to the container.

In some instances a plurality of containers can be contained within a halo-like structure as described above. For example, up to 100, 1,000, 10,000, 100,000, or 1,000,000 containers can be arranged in a meter-square of a halo-like structure. In some embodiments, the product (e.g. fuel molecule) is collected by harvesting the liquid medium. As some fuel molecules monoterpenes) are immiscible in water, they would float to the surface of the liquid medium and could be extracted easily. In other instances, the fuel molecules can be extracted from the liquid medium. In still other instances, the fuel molecules are volatile. In such instances, impermeable barriers can cover or otherwise surround the growth environment and can be extracted from the air within the barrier. For some fuel molecules, the product may be extracted from both the environment (e.g., liquid environment and/or air) and from the intact host cells. Typically, the organism would be harvested at an appropriate point and the product may then be extracted from the organism. In some instances, the product may be produced without killing the organisms. Producing and/or expressing the product may not render the organism unviable.

The present disclosure further provides genetically modified host cells, and will in some embodiments comprise one or more further components, which components are selected based in part on the intended use of the genetically modified host cell. Suitable components include, but are not limited to, salts; buffers; stabilizers; protease-inhibiting agents; cell membrane- and/or cell wall-preserving compounds, e.g., glycerol and dimethylsulfoxide; and nutritional media appropriate to the cell.

For the production of an isoprenoid or isoprenoid precursor compound, a host cell can be, for example, one that produces, or has been genetically modified to produce, one or more enzymes in a prenyl transferase pathway and/or a mevalonate pathway and/or an isoprenoid biosynthetic pathway. In some embodiments, the host cell is one that produces a substrate of a prenyl transferase, isoprenoid synthase mevalonate pathway enzyme.

In some embodiments, a genetically modified host cell is a host cell that comprises an endogenous mevalonate pathway and/or isoprenoid biosynthetic pathway and/or prenyl transferase pathway. In other embodiments, a genetically modified host cell is a host cell that does not normally produce mevalonate or IPP via a mevalonate pathway, or FPP, GPP or GGPP via a prenyl transferase pathway, but has been genetically modified with one or more polynucleotides comprising nucleotide sequences encoding one or more mevalonate pathway, isoprenoid synthase pathway or prenyl transferase pathway enzymes (for example, as described in U.S. Patent Publication No. 2004/005678; U.S. Patent Publication No. 2003/0148479; and Martin et al. (2003) Nat. Biotech. 21(7):796-802).

A polynucleotides as described herein is introduced into a suitable host cell. The selected polynucleotide can be, for example, inserted into a vector which includes appropriate control sequences.

Introduction of Nucleic Acids into a Host Organism or Cell

To generate a genetically modified host cell, a polynucleotide, or a polynucleotide cloned into a vector, is introduced stably or transiently into a host cell, using established techniques, including, but not limited to, electroporation, calcium phosphate precipitation, DEAE-dextran mediated transfection, and liposome-mediated transfection. For transformation, a polynucleotide of the present disclosure will generally further include a selectable marker, e.g., any of several well-known selectable markers such as neomycin resistance, ampicillin resistance, tetracycline resistance, chloramphenicol resistance, and kanamycin resistance.

A polynucleotide or recombinant nucleic acid molecule described herein, can be introduced into a plant cell (e.g., alga cell) using any method known in the art. A polynucleotide can be introduced into a cell by a variety of methods, which are well known in the art and selected, in part, based on the particular host cell. For example, the polynucleotide can be introduced into a plant cell using a direct gene transfer method such as electroporation or microprojectile mediated (biolistic) transformation using a particle gun, or the "glass bead method," or by pollen-mediated transformation, liposome-mediated transformation, transformation using wounded or enzyme-degraded immature embryos, or wounded or enzyme-degraded embryogenic callus (for example, as described in Potrykus. Ann Rev. Plant. Physiol. Plant Mol. Biol. 42:205-225, 1991).

Microprojectile mediated transformation also can be used to introduce a polynucleotide into a plant cell (for example, as described in Klein et al., Nature 327:70-73, 1987). This method utilizes microprojectiles such as gold or tungsten, which are coated with the desired polynucleotide by precipitation with calcium chloride, spermidine or polyethylene glycol. The microprojectile particles are accelerated at high speed into a plant tissue using a device such as the BIOLISTIC PD-1000 particle gun (BioRad; Hercules Calif.). Methods for the transformation using biolistic methods are well known in the art (for example, as described in Christou, Trends in Plant Science 1:423-431, 1996). Microprojectile mediated transformation has been used, for example, to generate a variety of transgenic plant species, including cotton, tobacco, corn, hybrid poplar and papaya. Important cereal crops such as wheat, oat, barley, sorghum and rice also have been transformed using microprojectile mediated delivery (for example, as described in Duan et al., Nature Biotech. 14:494-498, 1996; and Shimamoto, Curr. Opin. Biotech. 5:158-162, 1994). The transformation of most dicotyledonous plants is possible with the methods described above. Transformation of monocotyledonous plants also can be transformed using, for example, biolistic methods as described above, protoplast transformation, electroporation of partially permeabilized cells, introduction of DNA using glass fibers, and the glass bead agitation method.

In some embodiments, an alga is transformed with a nucleic acid which encodes a protein of interest, for example, a prenyl transferase, an isoprenoid synthase, or an enzyme capable of converting a precursor into a fuel product or a precursor of a fuel product (e.g., isoprenoid or fatty acid). In one embodiment, a transformation may introduce a nucleic acid into a plastid of the host alga (e.g., chloroplast). In another embodiments a transformation may introduce a nucleic acid into the nuclear genome of the host alga. In still another embodiment, a transformation may introduce nucleic acids into both the nuclear genome and into a plastid. Transformed cells can be plated on selective media following introduction of exogenous nucleic acids. This method may also comprise several steps for screening. A screen of primary transformants can be conducted to determine which clones have proper insertion of the exogenous nucleic acids. Clones which show the proper integration may be propagated and re-screened to ensure genetic stability. Such methodology ensures that the transformants contain the genes of interest. In many instances, such screening is performed by polymerase chain reaction (PCR); however, any other appropriate technique known in the art may be utilized. Many different methods of PGR are known in the art (e.g., nested PCR, real time PCR). For any given screen, one of skill in the art will recognize that PCR components may be varied to achieve optimal screening results. For example, magnesium concentration may need to be adjusted upwards when PCR is performed on disrupted alga cells to which EDTA (which chelates magnesium) is added to chelate toxic metals. Following the screening for clones with the proper integration of exogenous nucleic acids, clones can be screened for the presence of the encoded protein(s) and/or products. Protein expression screening can be performed by Western blot analysis and/or enzyme activity assays. Transporter and/or product screening may be performed by any method known in the art, for example ATP turnover assay, substrate transport assay, HPLC or gas chromatography.

The expression of the protein or enzyme can be accomplished by inserting a polynucleotide sequence (gene) encoding the protein or enzyme into the chloroplast or nuclear genome of a microalgae. The modified strain of microalgae can be made homoplasmic to ensure that the polynucleotide will be stably maintained in the chloroplast genome of all descendents. A microalga is homoplasmic for a gene when the inserted gene is present in all copies of the chloroplast genome, for example. It is apparent to one of skill in the art that a chloroplast may contain multiple copies of its genome, and therefore, the term "homoplasmic" or "homoplasmy" refers to the state where all copies of a particular locus of interest are substantially identical. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% or more of the total soluble plant protein. The process of determining the plasmic state of an organism of the present disclosure involves screening transformants for the presence of exogenous nucleic acids and the absence of wild-type nucleic acids at a given locus of interest.

Vectors

Construct, vector and plasmid are used interchangeably throughout the disclosure. In some embodiments, a polynucleotide of the present disclosure is cloned or inserted into an expression vector using cloning techniques know to one of skill in the art. Suitable expression vectors include, but are not limited to, baculovirus vectors, bacteriophage vectors, plasmids, phagemids, cosmids, fosmids, bacterial artificial chromosomes, viral vectors (e.g. viral vectors based on vaccinia virus, poliovirus, adenovirus, adeno-associated virus, SV40, and herpes simplex virus), PI-based artificial chromosomes, yeast plasmids, yeast artificial chromosomes, and any other vectors specific for specific hosts of interest (such as E. coli and yeast). Thus, for example, a polynucleotide encoding a prenyl transferase isoprenoid synthase can be inserted into any one of a variety of expression vectors for expressing the prenyl transferase or isoprenoid synthase. Such vectors can include, for example, chromosomal, nonchromosomal and synthetic DNA sequences.

Numerous suitable expression vectors are known to those of skill in the art. The following vectors are provided by way of example; for bacterial host cells: pQE vectors (Qiagen), pBluescript plasmids, pNH vectors, lambda-ZAP vectors (Stratagene), pTrc99a, pKK223-3, pDR540, and pRIT2T (Pharmacia); for eukaryotic host cells: pXT1, pSG5 (Stratagene), pSVK3, pBPV, pMSG, PET21a-d(+) vectors (Novagen), and pSVLSV40 (Pharmacia). However, any other plasmid or other vector may be used so long as it is compatible with the host cell.

The expression vector, or a linearized portion thereof, can encode one or more exogenous or endogenous nucleotide sequences. Examples of exogenous nucleotide sequences that can be transformed into a host, for example, an algal host, include genes from bacteria, fungi, plants, photosynthetic bacteria or other algae. Examples of other types of nucleotide sequences that can be transformed into a host, for example, an algal host include, but are not limited to, transporter genes, isoprenoid producing genes, including genes which encode for proteins which produce isoprenoids with two phosphates (e.g., GPP synthase and/or FPP synthase), genes which encode for proteins which produce fatty acids, lipids or triglycerides, endogenous promoters and 5' UTRs from the psbA, atpA, or rbcL genes. In some instances, an exogenous sequence is flanked by two homologous sequences.

Homologous sequences are, for example, those that have at least 50%, at least 60%, at least 70%, at least 80%, at least 90%, at least 95%, at least 98%, or at least at least 99% sequence identity to a reference amino acid sequence, for example, the amino acid sequence found naturally in the host cell. The first and second homologous sequences enable recombination of the exogenous or endogenous sequence into the genome of the host organism. The first and second homologous sequences can be at least 100, at least 200, at least 300, at least 400, at least 500, or at least 1500 nucleotides in length.

The polynucleotide sequence may comprise nucleotide sequences that are codon biased for expression in the organism being transformed. The skilled artisan is well aware of the "codon-bias" exhibited by a specific host cell in usage of nucleotide codons to specify a given amino acid. Without being bound by theory, by using a host cell's preferred codons, the rate of translation may be greater. Therefore, when synthesizing a gene for improved expression in a host cell, it may be desirable to design the gene such that its frequency of codon usage approaches the frequency of preferred codon usage of the host cell. In some organisms, codon bias differs between the nuclear genome and organelle genomes, thus, codon optimization or biasing may be performed for the target genome (e.g., nuclear codon biased or chloroplast codon biased). In some embodiments, codon biasing occurs before mutagenesis to generate a polypeptide. In other embodiments, codon biasing occurs after mutagenesis to generate a polypeptide. In yet other embodiments, codon biasing occurs before mutagenesis well as after mutagenesis. Codon bias is described in detail above.

In some embodiments, a vector comprises a polynucleotide operably linked to one or more control elements, such as a promoter and/or a transcription terminator. A vector in some embodiments provides for amplification of the copy number of a polynucleotide. A vector can be, for example, an expression vector that provides for expression of a prenyl transferase, an isoprenoid synthase, or a mevalonate synthesis enzyme in a host cell, e.g., a prokaryotic host cell or a eukaryotic host cell.

A polynucleotide or polynucleotides can be contained in a vector or vectors. For example, where a second (or more) nucleic acid molecule is desired, the second nucleic acid molecule can be contained in a vector, which can, but need not be, the same vector as that containing the first nucleic acid molecule. The vector can be any vector useful for introducing a polynucleotide into a genome and can include a nucleotide sequence of genomic DNA (e.g., nuclear or plastid) that is sufficient to undergo homologous recombination with genomic DNA, for example, a nucleotide sequence comprising about 400 to about 1500 or more substantially contiguous nucleotides of genomic DNA.

In some instances, such vectors include promoters. Promoters useful for the present disclosure may come from any source (e.g., viral, bacterial, fungal, protist, and animal). The promoters contemplated herein can be specific to photosynthetic organisms, non-vascular photosynthetic organisms, and vascular photosynthetic organisms (e.g., algae, flowering plants). In some instances, the nucleic acids above are inserted into a vector that comprises a promoter of a photosynthetic organism, e.g., algae. The promoter can be a constitutive promoter or an inducible promoter. A promoter typically includes necessary nucleic acid sequences near the start site of transcription, (e.g., a TATA element).

A "constitutive" promoter is a promoter that is active under most environmental and developmental conditions. An "inducible" promoter is a promoter that is active tinder controllable environmental or developmental conditions. Examples of inducible promoters/regulatory elements include, for example, a nitrate-inducible promoter (for example, as described in Bock et al, Plant Mol. Biol. 17:9 (1991)), or a light-inducible promoter, (for example, as described in Feinbaum et al, Mol Gen. Genet. 226:449 (1991); and Lam and Chua, Science 248:471 (1990)), or a heat responsive promoter (for example, as described in Muller et al., Gene 111: 165-73 (1992)).

In many embodiments, a polynucleotide of the present disclosure includes a nucleotide sequence encoding a protein or enzyme of the present disclosure, where the nucleotide sequence encoding the polypeptide is operably linked to an inducible promoter. Inducible promoters are well known in the art. Suitable inducible promoters include, but are not limited to, the pL of bacteriophage λ; Placo; Ptrp; Ptac (Ptrp-lac hybrid promoter); an isopropyl-beta-D-thiogatactopyranoside (IPTG)-inducible promoter, e.g., a lacZ promoter; a tetracycline-inducible promoter; an arabinose inducible promoter, e.g., PBAD (for example, as described in Guzman et al. (1995) J. Bacteriol. 177:4121-4130); a xylose-inducible promoter, e.g., Pxyl (for example, as described in Kim et al. (1996) Gene 181:71-76); a GAL1 promoter; tryptophan promoter; a lac promoter; an alcohol-inducible promoter, e.g., a methanol-inducible promoter, an ethanol-inducible promoter; a raffinose-inducible promoter; and a heat-inducible promoter, e.g., heat inducible lambda PL promoter and a promoter controlled by a heat-sensitive repressor (e.g., C1857-repressed lambda-based expression vectors; for example, as described in Hoffmann et al. (1999) FEMS Microbiot Lett. 177(2):327-34).

In many embodiments, a polynucleotide of the present disclosure includes a nucleotide sequence encoding a protein or enzyme of the present disclosure, where the nucleotide sequence encoding the polypeptide is operably linked to a constitutive promoter. Suitable constitutive promoters for use in prokaryotic cells are known in the an and include, but are not limited to, a sigma70 promoter, and a consensus sigma70 promoter.

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter; an araBAD promoter; in vivo regulated promoters, such as an ssaG promoter or a related promoter (for example, as described in U.S. Patent Publication No. 20040131637), a pagC promoter (for example, as described in Pulkkinen and Miller, J. Bacteria, 1991: 173(1): 86-93; and Alpuche-Aranda et al., PNAS, 1992; 89(21): 10079-83), a nirB promoter (for example, as described in Harborne et al. (1992) Mol. Micro. 6:2805-2813; Dunstan et al. (1999) Infect. Immun. 67:5133-5141; McKelvie et al, (2004) Vaccine 22:3243-3255; and Chatfield et at (1992) Biotechnol. 10:888-892); a sigma70 promoter, e.g., a consensus sigma70 promoter (for example, GenBank Accession Nos. AX798980, AX798961, and AX798183); a stationary phase promoter, e.g. a dps promoter, an spv promoter; a promoter derived from the pathogenicity island SP1-2 (for example, as described in WO96/17951); an actA promoter (for example, as described in Shetron-Rama et al. (2002) Infect. Immun, 70:1087-1096); an rpsM promoter (for example, as described in Valdivia and Falkow (1996). Mol. Microbiol. 22:367-378); a tet promoter (for example, as described in Hillen, W. and Wissmann. A. (1989) In Saenger, W. and Heinemann, U. (eds), Topics in Molecular and Structural Biology, Protein-Nucleic Acid Interaction. Macmillan, London, UK, Vol. 10, pp. 143-162); and an SP6 promoter (for example, as described in Melton et al, (1984) Nucl. Acids Res. 12:7035-7056).

In yeast, a number of vectors containing constitutive or inducible promoters may be used. For a review of such vectors see, Current Protocols in Molecular Biology, Vol. 2, 1988, Ed. Ausubel, et al., Greene Publish. Assoc. & Wiley Interscience, Ch. 13; Grant, et al., 1987, Expression and Secretion Vectors for Yeast, in Methods in Enzymology, Eds. Wu & Grossman, 31987. Acad. Press, N.Y., Vol. 153, pp. 516-544; Glover, 1986, DNA Cloning, Vol. II, IRL, Press, Wash., D.C., Ch. 3; Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast *Saccharomyces*, 1982, Eds. Strathern et al., Cold Spring Harbor Press, Vols. I and II. A constitutive yeast promoter such as ADH or LEU2 or an inducible promoter such as GAL may be used (for example, as described in Cloning in Yeast, Ch. 3, R. Rothstein In: DNA Cloning Vol. 11. A Practical Approach, Ed. DM Glover, 1986, IRL Press, Wash., D.C.). Alternatively, vectors may be used which promote integration of foreign DNA sequences into the yeast chromosome.

Non-limiting examples of suitable eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression.

A vector utilized in the practice of the disclosure also can contain one or more additional nucleotide sequences that confer desirable characteristics on the vector, including, for example, sequences such as cloning sites that facilitate manipulation of the vector, regulatory elements that direct replication of the vector or transcription of nucleotide sequences contain therein, and sequences that encode a selectable marker. As such, the vector can contain, for example, one or more cloning sites such as a multiple cloning site, which can, but need not be, positioned such that a exogenous or endogenous polynucleotide can be inserted into the vector and operatively linked to a desired element. The vector also can contain a prokaryote origin of replication (ori), for example, an *E. coli* on or a cosmid ori, thus allowing passage of the vector into a prokaryote host cell, as well as into a plant chloroplast.

A regulatory element, as the term is used herein, broadly refers to a nucleotide sequence that regulates the transcription or translation of a polynucleotide or the localization of a polypeptide to which it is operatively linked. Examples include, but are not limited to, an RBS, a promoter, enhancer, transcription terminator, an initiation (start) codon, a splicing signal for intron excision and maintenance of a correct reading frame, a STOP codon, an amber or ochre codon, an IRES. Additionally, a cell compartmentalization signal (i.e., a sequence that targets a polypeptide to the cytosol, nucleus, chloroplast membrane or cell membrane). In some aspects of the present disclosure, a cell compartmentalization signal e.g., a cell membrane targeting sequence) may be ligated to a gene and/or transcript, such that translation of the gene occurs in the chloroplast. In other aspects, a cell compartmentalization signal may be ligated to a gene such that, following translation of the gene, the protein is transported to the cell membrane.

A vector, or a linearized portion thereof, may include a nucleotide sequence encoding a reporter polypeptide or other selectable marker. The term "reporter" or "selectable marker" refers to a polynucleotide (or encoded polypeptide) that confers a detectable phenotype. A reporter generally encodes a detectable polypeptide, for example, a green fluorescent protein or an enzyme such as luciferase, which, when contacted with an appropriate agent (a particular wavelength of tight or luciferin, respectively) generates a signal that can be detected by eye or using appropriate instrumentation (for example, as described in Giacomin, Plant Sci. 116:59-72, 1996; Scikantha, J. Bacteria 178:121, 1996; Gerdes, FEBS Lett. 389:44-47, 1996; and Jefferson, EMBO J. 6:3901-3907, 1997, fl-glucuronidase). A selectable marker generally is a molecule that, when present or expressed in a cell, provides a selective advantage (or disadvantage) to the cell containing the marker, for example, the ability to grow in the presence of an agent that otherwise would kill the cell.

A selectable marker can provide a means to obtain, for example, prokaryotic cells or plant cells or both that express the marker and, therefore, can be useful as a component of a vector of the disclosure. One class of selectable markers are native or modified genes which restore a biological or physiological function to a host cell (e.g., restores photosynthetic capability or restores a metabolic pathway). Other examples of selectable markers include, but are not limited to, those that confer antimetabolite resistance, for example, dihydrofolate reductase, which confers resistance to methotrexate (for example, as described in Reiss, Plant (Life Sci. Adv.) 13:143-149, 1994); neomycin phosphotransferase, which confers resistance to the aminoglycosides neomycin, kanamycin and paromycin (for example, as described in Herrera-Estrella, EMBO J. 2:987-995, 1983), hygro, which confers resistance to hygromycin (for example, as described in Marsh, Gene 32:481-485, 1984), trpB, which allows cells to utilize indole in place of tryptophan; hisD, which allows cells to utilize histinol in place of histidine (for example, as described in Hartman, Proc. Natl. Acad. Sci., USA 85:8047, 1988); mannose-6-phosphate isomerase which allows cells to utilize mannose (for example, as described in PCT Publication Application No. WO 94/20627); ornithine decarboxylase, which confers resistance to the ornithine decarboxylase inhibitor, 2-(difluoromethyl)-DL-ornithine (DFMO; for example, as described in McConlogue, 1987. In: Current Communications in Molecular Biology, Cold Spring Harbor Laboratory ed.); and deaminase from *Aspergillus terreus*, which confers resistance to Blasticidin S (for example, as described in Tamura, Biosci, Biotechnol. Biochem. 59:2336-2338, 1995). Additional selectable markers include those that confer herbicide resistance, for example, phosphinothricin acetyltransferase gene, which confers resistance to phosphinothricin (for example, as described in White et al., Nucl. Acids Res. 18:1062, 1990; and Spencer et al., Theor. Appl. Genet. 79:625-631, 1990), a mutant EPSPV-synthase, which confers glyphosate resistance (for example, as described in Hinchee et al., BioTechnology 91:915-922, 1998), a mutant acetolactate synthase, which confers imidazolione or sulfonylurea resistance (for example, as described in Lee et al., EMBO J. 7:1241-1248, 1988), a mutant psbA, which confers resistance to atrazine (for example, as described in Smeda et al., Plant Physiol. 103:911-917, 1993), or a mutant protoporphyrinogen oxidase (for example, as described in U.S. Pat. No. 5,767,373), or other markers conferring resistance to an herbicide such as glufosinate. Selectable markers include polynucleotides that confer dihydrofolate reductase (DHFR) or neomycin resistance for eukaryotic ampicillin resistance for prokaryotes such as *E. coli*; and bleomycin, gentamycin, glyphosate, hygromycin, kanamycin, methotrexate, phleomycin, phosphinotricin, spectinomycin, streptomycin, sulfonamide and sulfonylurea resistance in plants (for example, as described in Maliga et at, Methods in Plant Molecular Biology, Cold Spring Harbor Laboratory Press, 1995, page 39).

Reporter genes have been successfully used in chloroplasts of higher plants, and high levels of recombinant protein expression have been reported. In addition, reporter genes have been used in the chloroplast of *C. reinhardtii*. Reporter genes greatly enhance the ability to monitor gene expression in a number of biological organisms. In chloroplasts of higher plants, β-glucuronidase (uidA, for example, as described in Staub and Maliga, EMBO J. 12:601-606, 1993), neomycin phosphotransferase (nptII, for example, as described in Carrer et al., Mol. Gen. Genet. 241:49-56, 1993), adenosyl-3-adenyltransferase (aadA, for example, as described in Svab and Maliga, Proc. Natl. Acad. Sci., USA 90:913-917, 993), and the Aequorea victoria GFP (for example, as described in Sidorov et al., Plant J. 19:209-216, 1999) have been used as reporter genes (for example, as described in Heifetz, Biochemie 82:655-666, 2000). Each of these genes has attributes that make them useful reporters of chloroplast gene expression, such as ease of analysis, sensitivity, or the ability to examine expression in situ. Based upon these studies, other exogenous proteins have been expressed in the chloroplasts of higher plants such as *Bacillus thuringiensis* Cry toxins, conferring resistance to insect herbivores (for example, as described in Kota et al., Proc, Natl. Acad, Sci., USA 96:1840-1845, 1999), or human somatotropin (for example, as described in Staub et al., Nat. Biotechnol. 18:333-338, 2000), a potential biopharmaceutical. Several reporter genes have been expressed in the chloroplast of the eukaryotic green alga, *C. reinhardtii*, including aadA (for example, as described in Goldschmidt-Clermont, Nucl. Acids Res. 19:4083-4089 1991; and Zerges and Rochaix, Mol. Cell Biol. 14:5268-5277, 1994), uidA (for example, as described in Sakamoto et al., Proc. Natl. Acad. Sci., USA 90:477-501, 1993; and Ishikura et al., J. Biosci. Bioeng. 87:307-314 1999), *Renilla luciferase* (for example, as described in Minko et al., Mol. Gen. Genet. 262:421-425, 1999) and the amino glycoside phosphotransferase from *Acinetobacter baumanii*, aphA6 (for example, as described in Bateman and Purton, Mol. Gen. Genet. 263:404-410, 2000).

In some instances, the vectors of the present disclosure will contain elements such as an *E. coli* or *S. cerevisiae* origin of replication. Such features, combined with appropriate selectable markers, allows for the vector to be "shuttled" between the target host cell and a bacterial and/or yeast cell. The ability to passage a shuttle vector of the disclosure in a secondary host may allow for more convenient manipulation of the features of the vector. For example, a reaction mixture containing the vector and putative inserted polynucleotides of interest can be transformed into prokaryote host cells such as *E. coli*, amplified and collected using routine methods, and examined to identify vectors containing an insert or construct of interest. If desired, the vector can be further manipulated, for example, by performing site directed mutagenesis of the inserted polynucleotide, then again amplifying and selecting vectors having a mutated polynucleotide of interest. A shuttle vector then can be introduced into plant chloroplasts, wherein a polypeptide of interest can be expressed and, if desired, isolated according to a method of the disclosure.

Knowledge of the chloroplast or nuclear genome of the host organism, for example, *C. reinhardtii*, is useful in the construction of vectors for use in the disclosed embodiments. Chloroplast vectors and methods for selecting regions of a chloroplast genome for use as a vector are well known (see, for example, Bock, J. Mol. Biol. 312:425 438, 2001; Staub and Maliga, Plant Cell 4:39 45, 1992; and Kavanagh et al., Genetics 152:1111 1122, 1999, each of which is incorporated herein by reference). The entire chloroplast genome *C. reinhardtii* is available to the public on the world wide web, at the "biology.duke.edu/chlamy_genome/chloro.html" (see "view complete genome as text file" link and "maps of the chloroplast genome" link; J. Maul, J. W. Lilly, and D. B. Stern, unpublished results; revised Jan. 28, 2002; to be published as GenBank Acc. No. AF396929; and Maul, J. E., et al. (2002) The Plant Cell, Vol. 14 (2659-2679)). Generally, the nucleotide sequence of the chloroplast genomic DNA that is selected for use is not a portion of a gene, including a regulatory sequence or coding sequence. For example, the selected sequence is not a gene that if disrupted, due to the homologous recombination event, would produce a deleterious effect with respect to the chloroplast. For example, a deleterious effect on the replication of the chloroplast genome or to a plant cell containing the chloroplast. In this respect, the website containing the *C. reinhardtii* chloroplast genome sequence also provides maps showing coding and non coding regions of the chloroplast genome, thus facilitating selection of a sequence useful for constructing a vector (also described in Maul, J. E., et al. (2002) The Plant Cell, Vol. 14 (2659-2679)). For example, the chloroplast vector, p322, is a clone extending from the Eco (Eco RI) site at about position 143.1 kb to the Xho (XIto 1) site at about position 148.5 kb (see, world wide web, at the URL "biology.duke.edu/chlamy_genome/chloro.html", and clicking on "maps of the chloroplast genome" link, and "140 150 kb" link; also accessible directly on world wide web at URL "biology.duke.edu/chlamylchloro/chloro140.html").

In addition, the entire nuclear genome of *C. reinhardtii* is described in Merchant, S. S., et at, Science (2007), 318(5848):245-250, thus facilitating one of skill in the art to select a sequence or sequences useful for constructing a vector.

For expression of the polypeptide in a host, an expression cassette or vector may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to the gene, or may be derived from an exogenous source. Expression vectors generally have convenient restriction sites located near the promoter sequence to provide for the insertion of nucleic acid sequences encoding exogenous or endogenous proteins. A selectable marker operative in the expression host may be present.

The description herein provides that host cells may be transformed with vectors, One of skill in the art will recognize that such transformation includes transformation with circular or linearized vectors, or linearized portions of a vector. Thus, a host cell comprising a vector may contain the entire vector in the cell (in either circular or linear form), or may contain a linearized portion of a vector of the present disclosure. In some instances 0.5 to 1.5 kb flanking nucleotide sequences of chloroplast genomic DNA may be used. In some instances 0.5 to 1.5 kb flanking nucleotide sequences of nuclear genomic DNA may be used, or 2.0 to 5.0 kb may be used.

Codon Optimization

One or more codons of an encoding polynucleotide can be "biased" or "optimized" to reflect the codon usage of the host organism. For example, one or more codons of an encoding polynucleotide can be "biased" or "optimized" to reflect chloroplast codon usage or nuclear codon usage. Most amino acids are encoded by two or more different (degenerate) codons, and it is well recognized that various organisms utilize certain codons in preference to others.

Such preferential codon usage, which is utilized chloroplasts, is referred to herein as "chloroplast codon usage." Table 2 (below) shows the chloroptast codon usage for *C. reinhardtii* (see U.S. Patent Application Publication No.: 2004/0014174, published Jan. 22, 2004).

fied chloroplast genome can be provided and utilized for efficient translation of a polypeptide according to any method of the disclosure. Correlations between tRNA abundance and codon usage in highly expressed genes is well known (for example, as described in Franklin et al., Plant J. 30:733 744, 2002; Dong et at, J. Mol. Biol. 260:649 663, 1996; Duret, Trends Genet, 16:287 289, 2000; Goldman et. al., J. Mol. Biol. 245:467 473, 1995; and Komar et. al, Biol. Chem. 379:1295 1300, 1998). In *E. coli*, for example, re engineering of strains to express underutilized tRNAs resulted in enhanced expression of genes which utilize these codons (see Novy et al., in Novations 12:1 3, 2001). Utilizing endogenous tRNA genes, site directed mutagenesis can be used to make a synthetic tRNA gene, which can be introduced into chloroplasts to complement rare or unused tRNA genes in a chloroplast genome, such as a *C. reinhardtii* chloroplast genome.

TABLE 2

Chloroplast Codon Usage in *Chlamydomonas reinhardtii*

| UUU 34.1* (348**) | UCU 19.4 (198) | UAU 23.7 (242) | UGU 8.5 (87) |
|---|---|---|---|
| UUC 14.2 (145) | UCC 4.9 (50) | UAC 10.4 (106) | UGC 2.6 (27) |
| UUA 72.8 (742) | UCA 20.4 (208) | UAA 2.7 (28) | UGA 0.1 (1) |
| UUG 5.6 (57) | UCG 5.2 (53) | UAG 0.7 (7) | UGG 13.7 (140) |
| CUU 14.8 (151) | CCU 14.9 (152) | CAU 11.1 (113) | CGU 25.5 (260) |
| CUC 1.0 (10) | CCC 5.4 (55) | CAC 8.4 (86) | CGC 5.1 (52) |
| CUA 6.8 (69) | CCA 19.3 (197) | CAA 34.8 (355) | CGA 3.8 (39) |
| CUG 7.2 (73) | CCG 3.0 (31) | CAG 5.4 (55) | CGG 0.5 (5) |
| AUU 44.6 (455) | ACU 23.3 (237) | AAU 44.0 (449) | AGU 16.9 (172) |
| AUC 9.7 (99) | ACC 7.8 (80) | AAC 19.7 (201) | AGC 6.7 (68) |
| AUA 8.2 (84) | ACA 29.3 (299) | AAA 61.5 (627) | AGA 5.0 (51) |
| AUG 23.3 (238) | ACG 4.2 (43) | AAG 11.0 (112) | AGG 1.5 (15) |
| GUU 27.5 (280) | GCU 30.6 (312) | GAU 23.8 (243) | GGU 40.0 (408) |
| GUC 4.6 (47) | GCC 11.1 (113) | GAC 11.6 (118) | GGC 8.7 (89) |
| GUA 26.4 (269) | GCA 19.9 (203) | GAA 40.3 (411) | GGA 9.6 (98) |
| GUG 7.1 (72) | GCG 4.3 (44) | GAG 6.9 (70) | GGG 4.3 (44) |

*Frequency of codon usage per 1,000 codons.
**Number of times observed in 36 chloroplast coding sequences (10,193 codons).

The term "biased" or "optimized", when used in reference to a codon, means that the sequence of a codon in a polynucleotide has been changed such that the codon is one that is used preferentially in, for example, the chloroplasts of the organism (see Table 2), or the nuclear genome of the organism (see Table 3). "Biased" or codon "optimized" can be used interchangeably throughout the specification.

The chloroplast codon bias can, but need not, be selected based on a particular organism in which a synthetic polynucleotide is to be expressed. The manipulation can be a change to a codon, for example, by a method such as site directed mutagenesis, by a method such as PCR using a primer that is mismatched for the nucleotide(s) to be changed such that the amplification product is biased to reflect chloroplast codon usage, or can be the de novo synthesis of polynucleotide sequence such that the change (bias) is introduced as a consequence of the synthesis procedure.

In addition to utilizing chloroplast codon bias as a means to provide efficient translation of a polypeptide, it will be recognized that an alternative means for obtaining efficient translation of a polypeptide in a chloroplast is to re engineer the chloroplast genome (e.g., a *C. reinhardtii* chloroplast genome) for the expression of tRNAs not otherwise expressed in the chloroplast genome. Such an engineered algae expressing one or more exogenous tRNA molecules provides the advantage that it would obviate a requirement to modify every polynucleotide of interest that is to be introduced into and expressed from a chloroplast genome; instead, algae such as *C. reinhardtii* that comprise a genetically modi- Generally, the chloroplast codon bias selected for purposes of the present disclosure, including, for example, in preparing a synthetic polynucleotide as disclosed herein reflects chloroplast codon usage of a plant chloroplast, and includes a codon bias that, with respect to the third position of a codon, is skewed towards A/T, for example, where the third position has greater than about 66% AT bias, or greater than about 70% AT bias. In one embodiment, the chloroplast codon usage is biased to reflect alga chloroplast codon usage, for example, *C. reinhardtii*, which has about 74.6% AT bias in the third codon position.

Table 3 exemplifies codons that are preferentially used in algal nuclear genes. The nuclear codon bias can, but need not, be selected based on a particular organism in which a synthetic polynucleotide is to be expressed. The manipulation can be a change to a codon, for example, by a method such as site directed mutagenesis, by a method such as PCR using a primer that is mismatched for the nucleotide(s) to be changed such that the amplification product is biased to reflect nuclear codon usage, or can be the de novo synthesis of polynucleotide sequence such that the change (bias) is introduced as a consequence of the synthesis procedure.

In addition to utilizing nuclear codon bias as a means to provide efficient translation of a polypeptide, it will be recognized that an alternative means for obtaining efficient translation of a polypeptide in a nucleus is to re engineer the nuclear genome (e.g., a *C. reinhardtii* nuclear genome) for the expression of tRNAs not otherwise expressed in the nuclear genome. Such an engineered algae expressing one or more exogenous tRNA molecules provides the advantage that it would obviate a requirement to modify every polynucleotide of interest that is to be introduced into and expressed from a nuclear genome; instead, algae such as *C. reinhardtii* that comprise a genetically modified nuclear genome can be provided and utilized for efficient translation of a polypeptide according to any method of the disclosure. Correlations between tRNA abundance and codon usage in highly expressed genes is well known (for example, as described in Franklin et al., Plant J. 30:733 744, 2002; Dong et al., J. Mol. Biol, 260:649 663, 1996; Duret, Trends Genet. 16:287 289, 2000; Goldman et. Al., J. Mol. Biol. 245:467 473, 1995; and Komar et. Al., Biol. Chem. 379:1295 1300, 1998). In E. coli, for example, re engineering of strains to express underutilized tRNAs resulted in enhanced expression of genes which utilize these codons (see Novy et al., in Novations 12:1 3, 2001). Utilizing endogenous tRNA genes, site directed mutagenesis can be used to make a synthetic tRNA gene, which can be introduced into the nucleus to complement rare or unused tRNA genes in a nuclear genome, such as a *C. reinhardtii* nuclear genome.

Generally, the nuclear codon bias selected for purposes of the present disclosure, including, for example, in preparing a synthetic polynucleotide as disclosed herein, can reflect nuclear codon usage of an algal nucleus and includes a codon bias that results in the coding sequence containing greater than 60% G/C content.

TABLE 3

Nuclear Codon Usage in *Chlamydomonas reinhardtii*

| | | | |
|---|---|---|---|
| UUU 5.0 (2110) | UCU 4.7 (1992) | UAU 2.6 (1085) | UGU 1.4 (601) |
| UUC 27.1 (11411) | UCC 16.1 (6782) | UAC 22.8 (9579) | UGC 13.1 (5498) |
| UUA 0.6 (247) | UCA 3.2 (1348) | UAA 1.0 (441) | UGA 0.5 (227) |
| UUG 4.0 (1673) | UCG 16.1 (6763) | UAG 0.4 (183) | UGG 13.2 (5559) |
| CUU 4.4 (1869) | CCU 8.1 (3416) | CAU 2.2 (919) | CGU 4.9 (2071) |
| CUC 13.0 (5480) | CCC 29.5 (12409) | CAC 17.2 (7252) | CGC 34.9 (14676) |
| CUA 2.6 (1086) | CCA 5.1 (2124) | CAA 4.2 (1780) | CGA 2.0 (841) |
| CUG 65.2 (27420) | CCG 20.7 (8684) | CAG 36.3 (15283) | CGG 11.2 (4711) |
| AUU 8.0 (3360) | ACU 5.2 (2171) | AAU 2.8 (1157) | AGU 2.6 (1089) |
| AUC 26.6 (11200) | ACC 27.7 (11663) | AAC 28.5 (11977) | AGC 22.8 (9590) |
| AUA 1.1 (443) | ACA 4.1 (1713) | AAA 2.4 (1028) | AGA 0.7 (287) |
| AUG 25.7 (10796) | ACG 15.9 (6684) | AAG 43.3 (18212) | AGG 2.7 (1150) |
| GUU 5.1 (2158) | GCU 16.7 (7030) | GAU 6.7 (2805) | GGU 9.5 (3984) |
| GUC 15.4 (6496) | GCC 54.6 (22960) | GAC 41.7 (17519) | GGC 62.0 (26064) |
| GUA 2.0 (857) | GCA 10.6 (4467) | GAA 2.8 (1172) | GGA 5.0 (2084) |
| GUG 46.5 (19558) | GCG 44.4 (18688) | GAG 53.5 (22486) | GGG 9.7 (4087) | fields: [triplet] [frequency: per thousand] ([number])
Coding GC 66.30% $1^{st}$ letter GC 64.80% $2^{nd}$ letter GC 47.90% $3^{rd}$ letter GC 86.21%

Percent Sequence Identity

One example of an algorithm that is suitable for determining percent sequence identity or sequence similarity between nucleic acid or polypeptide sequences is the BLAST algorithm, which is described, e.g., Altschul et al. J. Mol, Biol., 215:403-410 (1990). Software for performing BLAST analysis is publicly available through the National Center for Biotechnology Information. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix (as described, for example, in Henikoff & Henikoff (1989) Proc. Natl. Acad. Sci, USA, 89:10915). In addition to calculating percent sequence identity, the BLAST algorithm also can perform a statistical analysis of the similarity between two sequences (for example, as described in Karlin & Altschul, Proc. Nat'l. Acad. Sci. USA, 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, less than about 0.01, or less than about 0.001.

Pathways to be Modified

Figure 6:
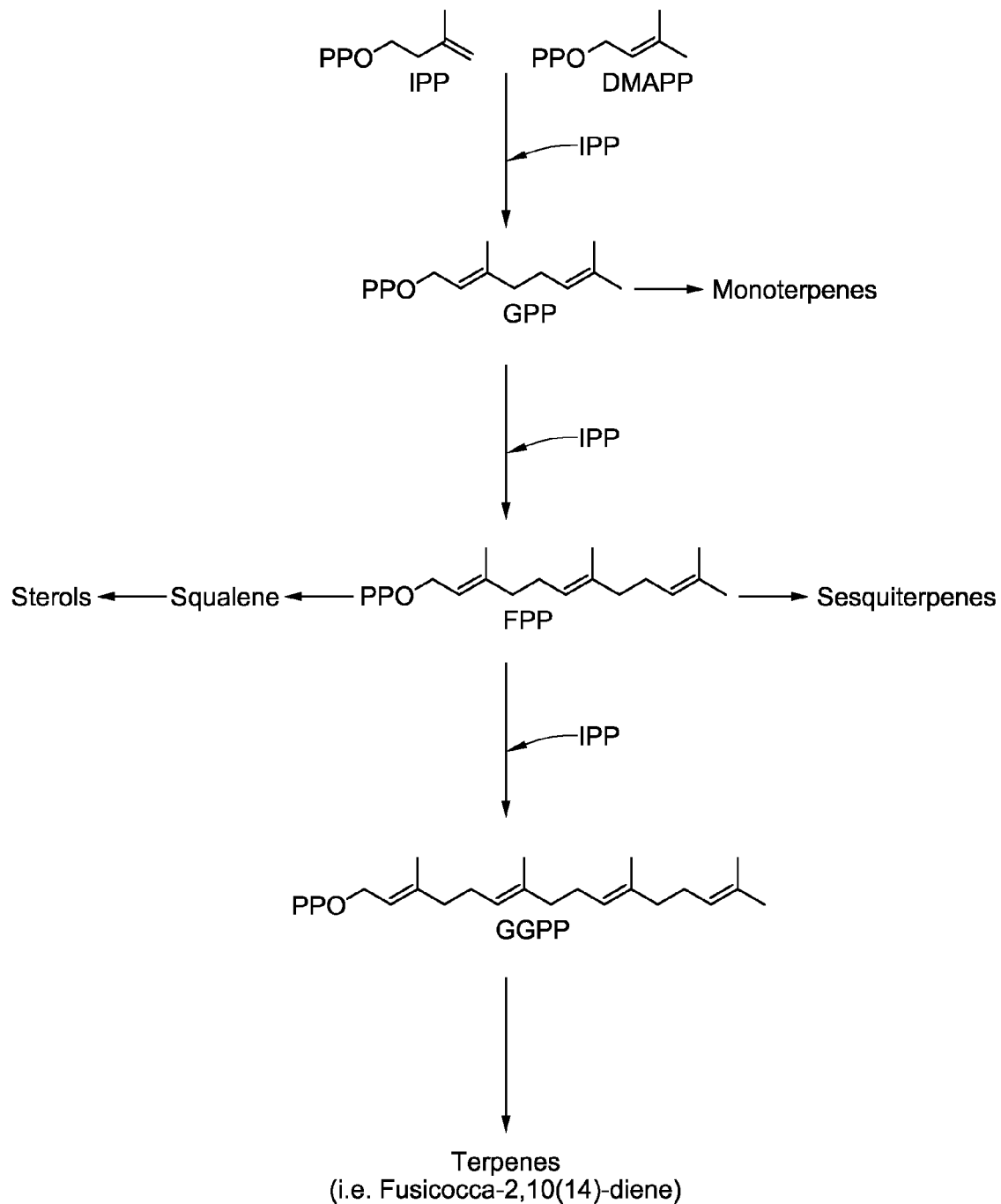
FIG. 6 shows the isoprenoid pathway, and exemplary products of the pathway, for example, fusiccoca-2,10(14)-diene.

The expression vectors described herein can encode a polypeptide whose expression results in the production of intermediates, precursors, and/or derivatives of proteins involved in the isoprenoid pathway (for example, as described in FIG. 6). The expression vectors described herein can also encode a polypeptide whose expression results in the production of a product or a derivative of a product of the isoprenoid pathway.

Figure 7:
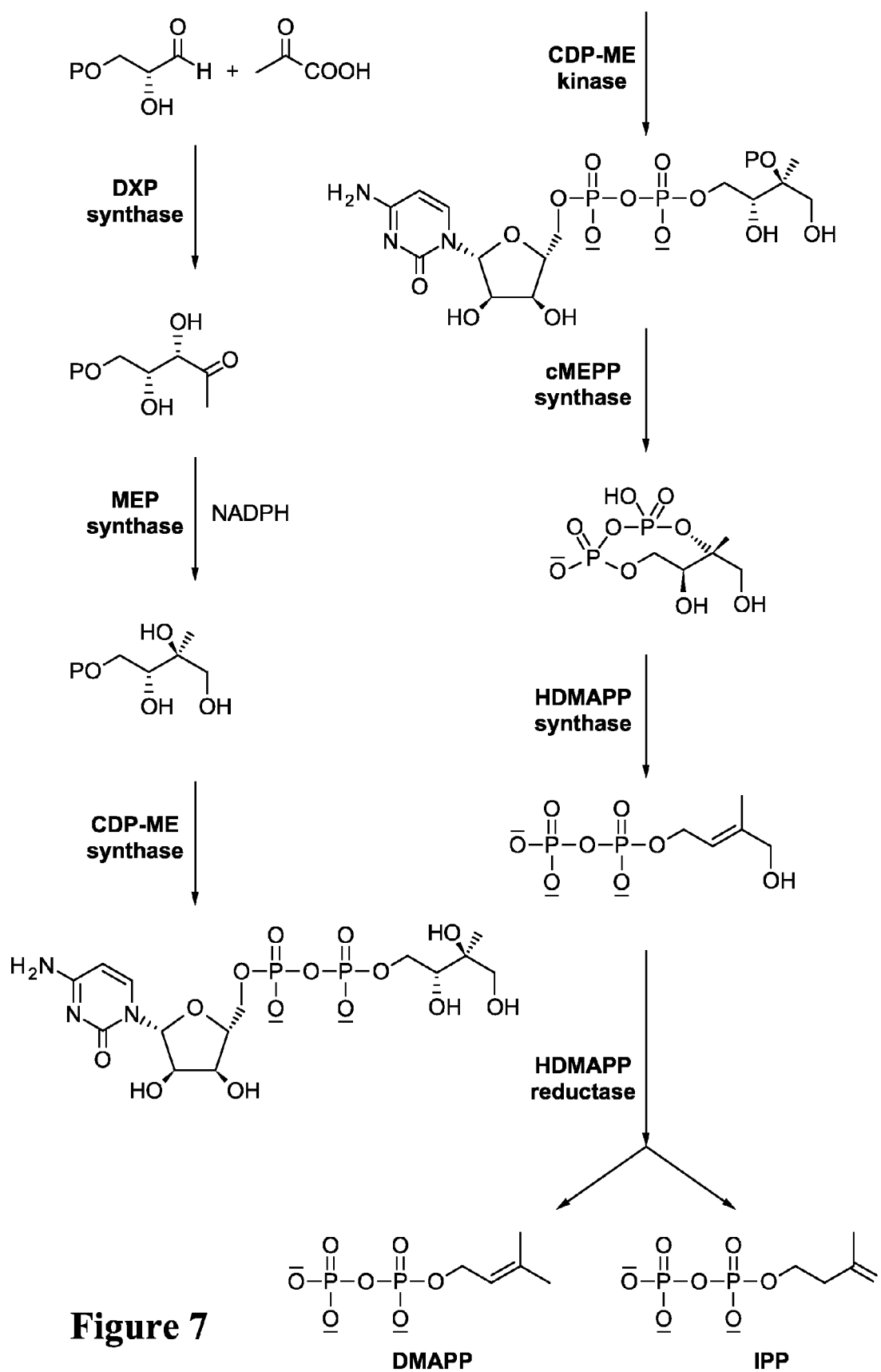
FIG. 7 shows the MEP pathway for the production of IPP and DMAPP.
Figure 8:
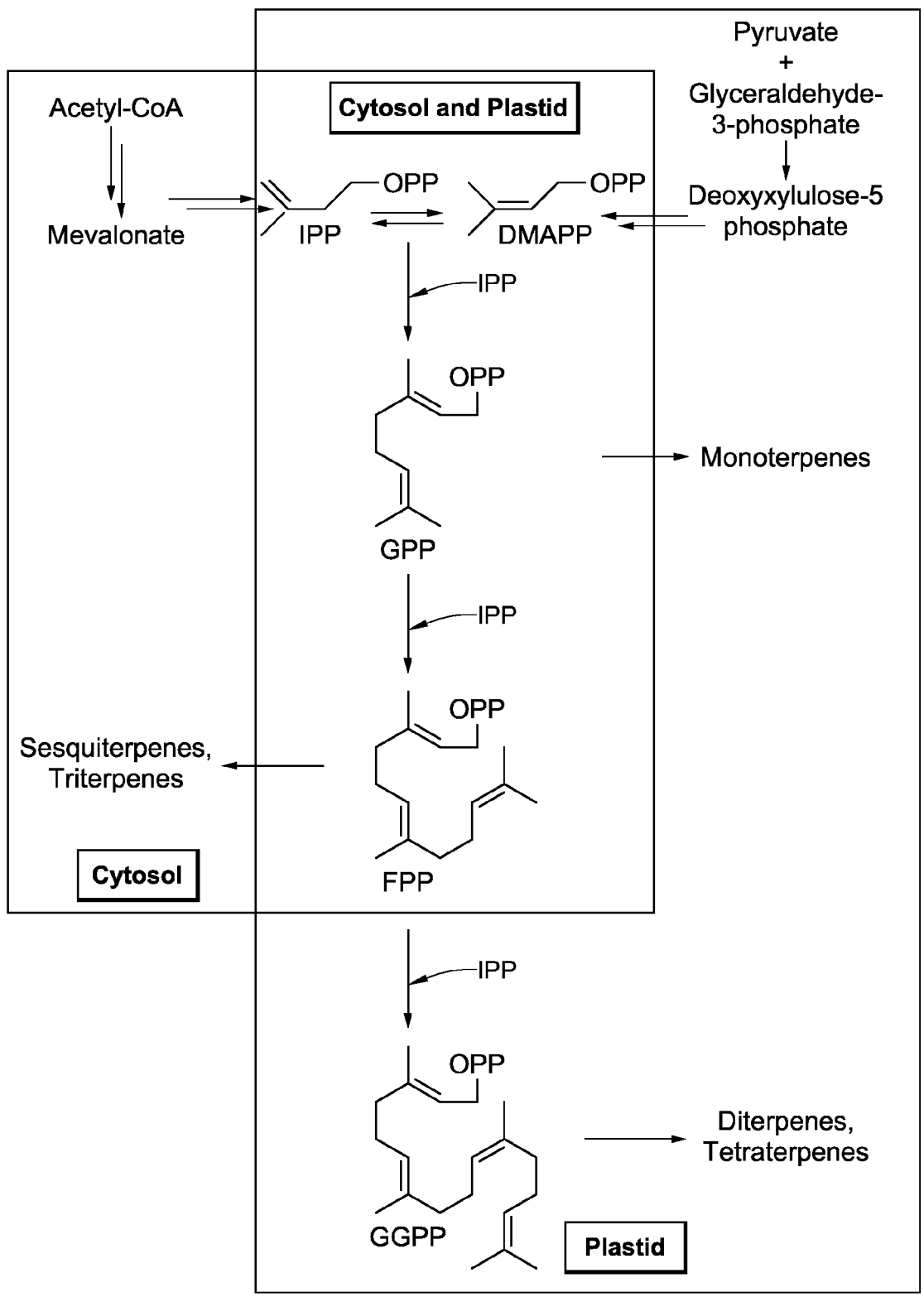
FIG. 8 shows an overview of terpene biosynthesis in photosynthetic eukaryotes.

Isoprenoid precursors are generated by one of two pathways; the mevalonate pathway or the methylerythritol phosphate (MEP) pathway (for example, as described in FIGS. 7 and 8). Both pathways generate dimethylallyl pyrophosphate (DMAPP) and isopentyl pyrophosphate (IPP), the common C5 precursor for isoprenoids. The DMAPP and IPP are condensed to form geranyl-diphosphate (GPP), or other precursors, such as farnesyl-diphosphate (FPP) or geranylgeranyl-diphosphate (GGPP), from which higher isoprenoids are formed.

An expression vector herein may encode polypeptide(s) involved in the mevalonate pathway, such as, for example, thiolase, HMG-CoA synthase, HMG-CoA reductase, mevalonate kinase, phosphemevalonate kinase, and mevalonate-5-pyrophosphate decarboxylase. In other embodiments, the polypeptide(s) is an enzyme(s) involved in the non-mevalonate pathway, such as DOXP synthase, DOXP reductase, 4-diphosphocytidyl-2-C-methyl-D-erythritol synthase, 4-diphosphocytidyl-2-C-methyl-D-erythritol kinase, 2-C-methyl-D-erythritol 2,4,-cyclodiphosphate synthase, HMB-PP synthase, HMB-PP reductase, DOXP reductoisomerase.

In other embodiments, an expression vector may comprise a nucleotide sequence encoding a polypeptide involved in the isoprenoid pathway, such as, for example, a synthase-encoding sequence. The synthase may be a C10, C15, C20, C30, or C40 synthase.

Examples of enzymes involved in the isoprenoid pathway and their sequences are described in Table 4. A nucleotide sequence encoding any one or more of the below listed proteins, or any other protein disclosed herein, can be used to transform a host cell or organism.

TABLE 4

Examples of Enzymes Involved in the Isoprenoid Pathway

| Enzyme | Source | NCBI protein ID |
|---|---|---|
| Limonene | M. spicata | 2ONH_A |
| Cineole | S. officinalis | AAC26016 |
| Pinene | A. grandis | AAK83564 |
| Camphene | A. grandis | AAB70707 |
| Sabinene | S. officinalis | AAC26018 |
| Myrcene | A. grandis | AAB71084 |
| Abietadiene | A. grandis | Q38710 |
| Taxadiene | T. brevifolia | AAK83566 |
| FPP | G. gallus | P08836 |
| Amorphadiene | A. annua | AAF61439 |
| Bisabolene | A. grandis | O81086 |
| Diapophytoene | S. aureus | |
| Diapophytoene desaturase | S. aureus | |
| GPPS-LSU | M. spicata | AAF08793 |
| GPPS-SSU | M. spicata | AAF08792 |
| GPPS | A. thaliana | CAC16849 |
| GPPS | C. reinhardtii | EDP05515 |
| FPP | E. coli | NP_414955 |
| FPP | A. thaliana | NP_199588 |
| FPP | A. thaliana | NP_193452 |
| FPP | C. reinhardtii | EDP03194 |
| Limonene | L. angustifolia | ABB73044 |
| Monoterpene | S. lycopersicum | AAX69064 |
| Terpinolene | O. basilicum | AAV63792 |
| Myrcene | O. basilicum | AAV63791 |
| Zingiberene | O. basilicum | AAV63788 |
| Myrcene | Q. ilex | CAC41012 |
| Myrcene | P. abies | AAS47696 |
| Myrcene, ocimene | A. thaliana | NP_179998 |
| Myrcene, ocimene | A. thaliana | NP_567511 |
| Sesquiterpene | Z. mays; B73 | AAS88571 |
| Sesquiterpene | A. thaliana | NP_199276 |
| Sesquiterpene | A. thaliana | NP_193064 |
| Sesquiterpene | A. thaliana | NP_193066 |
| Curcumene | P. cablin | AAS86319 |
| Farnesene | M. domestica | AAX19772 |
| Farnesene | C. sativus | AAU05951 |
| Farnesene | C. junos | AAK54279 |
| Farnesene | P. abies | AAS47697 |
| Bisabolene | P. abies | AAS47689 |
| Sesquiterpene | A. thaliana | NP_197784 |
| Sesquiterpene | A. thaliana | NP_175313 |
| GPP Chimera | | |
| GPPS-LSU + SSU fusion | | |
| Geranylgeranyl reductase | A. thaliana | NP_177587 |
| Geranylgeranyl reductase | C. reinhardtii | EDP09986 |
| FPP A118W | G. gallus | |

In addition to the enzymes in Table 4, additional exemplary terpene synthases include bisabolene synthase, (−)-limonene synthase, abeitadiene synthase, and taxadiene synthase.

The synthase may also be β-caryophyllene synthase, germacrene A synthase, 8-epicedrol synthase, valencene synthase, (+)-δ-cadinene synthase, germacrene C synthase, (E)-β-farnesene synthase, casbene synthase, vetispiradiene synthase, 5-epi-aristolachene synthase, aristoichene synthase, α-humulene, (E,E)-α-farnesene synthase, (−)-β-pinene synthase, limonene cyclase, linalool synthase, (+)-bornyl diphosphate synthase, levopimaradiene synthase, isopimaradiene synthase, (E)-γ-bisabolene synthase, copalyl pyrophosphate synthase, kaurene synthase, longifolene synthase, γ-humulene synthase, δ-selinene synthase, β-phellandrene synthase, terpinolene synthase, (+)-3-carene synthase, syn-copalyl diphosphate synthase, α-terpineot synthase, syn-pimara-7,15-diene synthase, ent-sartdaaracopimaradiene synthase, sterner-13-ene synthase, E-β-ocimene, S-linalool synthase, geraniol synthase, γ-terpinene synthase, synthase, E-β-ocimene synthase, epi-cedrol synthase, α-zingiberene synthase, guaiadiene synthase, cascarilladiene synthase, cis-muuroladiene synthase, aphidicolan-16b-ol synthase, elizabethatriene synthase, sandalol synthase, patchoulal synthase, zinzanol synthase, cedrol synthase, scareol synthase, copalol synthase, or manool synthase.

Pathways utilized for methods described herein may involve enzymes present in the cytosol, in a plastid (for example, chloroplast), both. Exogenous nucleic acids encoding an enzyme of interest may be introduced into a host cell, such that the enzyme encoded is active in the cytosol or in a plastid, or both. In some embodiments, a naturally occurring enzyme which is present in one intracellular compartment (for example, in the cytosol) may be expressed in a different intracellular locale (for example, in the chloroplast), or in both the naturally occurring and non-naturally occurring locales following transformation of the host cell.

To illustrate this concept, and by way of example, a non-vascular photosynthetic microalga (*Chlamydomonas rheinhardii*) species can be genetically engineered to produce an isoprenoid, such as limonene. Limonene is a monoterpene that is a pure hydrocarbon, only composed of hydrogen and carbon atoms, Limonene is not naturally produced in the species, *Chlamydomonas rheinhardii*. Production of limonene in these microalgae can be achieved by engineering the microalgae to express the exogenous enzyme limonene synthase in the chloroplast. Limonene synthase can convert the terpene precursor geranyl pyrophosphate into limonene. Unlike limonene, geranyl pyrophosphate is naturally present in the chloroplast of microalgae. The expression of the limonene synthase can be accomplished by inserting the exogenous gene encoding limonene synthase into the chloroplast genome of the microalgae. The modified strain of microalgae is then made homoplasmic to ensure that the limonene gene will be stably maintained in the chloroplast genome all descendents. A microalgae is homoplasmic for a gene when the inserted gene is present in all copies of the chloroplast genome. It is apparent to one of skill in the art that a chloroplast may contain multiple copies of its genome, and therefore, the term "homoplasmic" or "homoplasmy" refers to the state where all copies of a particular locus of interest are substantially identical. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein.

Products or Compounds

Provided herein are systems and methods for making a product using an oil composition derived from a biomass. Examples of products include petrochemical products, precursors of petrochemical products, fuel products, petroleum products, precursors of petroleum products, and all other substances that may be useful in the petrochemical industry. The product may be used for generating substances, or materials, useful in the petrochemical industry.

The products or fuel products may be used in a combustor such as a boiler, kiln, dryer or furnace. Other examples of combustors are internal combustion engines such as vehicle engines or generators, including gasoline engines, diesel engines, jet engines, and other types of engines. In one embodiment, a method herein comprises combusting a refined or "upgraded" composition. For example, combusting a refined composition can comprise inserting the refined composition into a combustion engine, such as an automobile engine or a jet engine. Products described herein may also be used to produce plastics, resins, fibers, elastomers, pharmaceuticals, nutraceuticals, lubricants, and gels, for example.

Fuel products, comprising hydrocarbons, may be, for example, precursors or products conventionally derived from crude oil, or petroleum, such as, but not limited to, liquid petroleum gas, naphtha (ligroin), gasoline, kerosene, diesel, lubricating oil, heavy gas, coke, asphalt, tar, and waxes.

In some embodiments, a product (such as a fuel product) contemplated herein comprises one or more carbons derived from an inorganic carbon source. In some embodiments, at least 10%, at least 20%, at least 30%, at least 40%, at least 50%, at least 60%, at least 70%, at least 80%, at least 90%, at least 95%, or at least 99% of the carbons of a product as described herein are derived from an inorganic carbon source. Examples of inorganic carbon sources include, but are not limited to, carbon dioxide, carbonate, bicarbonate, and carbonic acid. The product can be, for example, an organic molecule with carbons from an inorganic carbon source that were fixed during photosynthesis.

Examples of products contemplated herein include hydrocarbon products and hydrocarbon derivative products. A hydrocarbon product is one that consists of only hydrogen molecules and carbon molecules. A hydrocarbon derivative product is a hydrocarbon product with one or more heteroatoms, wherein the heteroatom is any atom that is not hydrogen or carbon. Examples of heteroatoms include, but are not limited to, nitrogen, oxygen, sulfur, and phosphorus. Some products can be hydrocarbon-rich, wherein, for example, at least 50%, at least 60%, at least 70%, at least 80%, at least 90%, or at least 95% of the product by weight is made up of carbon and hydrogen.

One exemplary group of hydrocarbon products are isoprenoids. Isoprenoids (including terpenoids) are derived from isoprene subunits, but are modified, for example, by the addition of heteroatoms such as oxygen, by carbon skeleton rearrangement, and by alkylation. Isoprenoids generally have a number of carbon atoms which is evenly divisible by five, but this is not a requirement as "irregular" terpenoids are known to one of skill in the art. Carotenoids, such as carotenes and xanthophylls, are examples of isoprenoids that are useful products. A steroid is an example of a terpenoid. Examples of isoprenoids include, but are not limited to, hemiterpenes (C5), monoterpenes (C10), sesquiterpenes (C15), diterpenes (C20), triterpenes (C30), tetraterpenes (C40), polyterpenes (Cn, wherein "n" is equal to or greater than 45), and their derivatives. Other examples of isoprenoids include, but are not limited to, limonene, 1,8-cineole, α-pinene, camphene, (+)-sabinene, myrcene, abietadiene, taxadiene, farnesyl pyrophosphate, fusicoccadiene, amorphadiene, (E)-α-bisabolene, zingiberene, or diaphytoene, and their derivatives.

In some embodiments, the compound, for example, an isoprenoid or isoprenoid compound is produced in a genetically modified host cell at a level that is at least about 2-fold, at least about 5-fold, at least about 10-fold, at least about 25-fold, at least about 50-fold, at least about 100-fold, at least about 500-fold, at least about 1000-fold, at least about 2000-fold, at least about 3000-fold, at least about 4000-fold, at least about 5000-fold, or at least about 10.000-fold, or more, higher than the level of the isoprenoid or isoprenoid precursor compound produced in an unmodified host cell that produces the isoprenoid or isoprenoid precursor compound via the same biosynthetic pathway.

In some embodiments, the compound, for example, an isoprenoid compound is pure, e.g., at least about 40% pure, at least about 50% pure, at least about 60% pure, at least about 70% pure, at least about 80% pure, at least about 90% pure, at least about 95% pure, at least about 98%, or more than 98% pure. "Pure" in the context of an isoprenoid compound refers to an isoprenoid compound that is free from other isoprenoid compounds, portions of compounds, contaminants, and unwanted byproducts, for example.

Useful products can also include isoprenoid precursors. Isoprenoid precursors are generated by one of two pathways; the mevalonate pathway or the methylerythritol phosphate (MEP) pathway. Both pathways generate dimethylallyl pyrophosphate (DMAPP) and isopentyl pyrophosphate (IPP), the common C5 precursor for isoprenoids. The DMAPP and IPP are condensed to form geranyl-diphosphate (GPP), or other precursors, such as farnesyl-diphosphate (FPP) or geranylgeranyl-diphosphate (GGPP), from which higher isoprenoids are formed.

In some embodiments, the compound or product, for example, an isoprenoid compound will be separated from other products which may be present in the organic layer. Separation of the compound from other products that may be present in the organic layer is readily achieved using, e.g., standard chromatographic techniques.

Useful products include, hut are not limited to, terpenes and terpenoids. An exemplary group of terpenes are diterpenes (C20). Diterpenes are hydrocarbons that can be modified (e.g. oxidized, methyl groups removed, or cyclized); the carbon skeleton of a diterpene can be rearranged, to form, for example, terpenoids, such as fusicoccadiene. Fusicoccadiene may also be formed, for example, directly from the isoprene precursors, without being bound by the availability of diterpene or GGDP. Genetic modification of organisms, such as algae, by the methods described herein, can lead to the production of fusicoccadiene, for example, and other types of terpenes, such as limonene, for example. Genetic modification can also lead to the production of modified terpenes, such as methyl squalene or hydroxylated and/or conjugated terpenes such as paclitaxel.

Other useful products can be, for example, a product comprising a hydrocarbon obtained from an organism expressing a diterpene synthase. Such exemplary products include ent-kaurene, casbene, and fusicocaccadiene, and may also include fuel additives.

Useful products can also include small alkanes (for example, 1 to approximately 4 carbons) such as methane, ethane, propane, or butane, which may be used for heating (such as in cooking) or making plastics. Products may also include molecules with a carbon backbone of approximately 5 to approximately 9 carbon atoms, such as naphtha or ligroin, or their precursors. Other products may be about 5 to about 12 carbon atoms, or cycloalkanes used as gasoline or motor fuel. Molecules and aromatics of approximately 10 to approximately 18 carbons, such as kerosene, or its precursors, may also be useful as products. Other products include lubricating oil, heavy gas oil, or fuel oil, or their precursors, and can contain alkanes, cycloalkanes, or aromatics of approximately 12 to approximately 70 carbons. Products also include other residuals that can be derived from or found in crude oil, such as coke, asphalt, tar, and waxes, generally containing multiple rings with about 70 or more carbons, and their precursors.

The modified host organism described herein is useful in the production of a desired compound or product. The present disclosure provides methods of producing, for example, an isoprenoid or isoprenoid precursor compound in a host cell. One such method involves, culturing a modified host cell in a suitable culture medium under conditions that promote the synthesis of a product, for example, an isoprenoid compound or isoprenoid precursor compound, where the isoprenoid compound is generated by the expression of an enzyme of the present disclosure, wherein the enzyme uses a substrate present in the host cell. In some embodiments, a method further comprises isolating the isoprenoid compound from the cell and/or from the culture medium.

The products produced may be naturally or non-naturally (as a result of the transformation) produced by a transformed host cell or organism(s), from which a biomass is obtained. The product may also be a molecule not present in nature. For example, products naturally produced in algae may be terpenes such as carotenoids (for example, beta-carotene). An example of a product not naturally produced by algae is a non-native terpene such as limonene.

Modified organisms can be grown, in some embodiments in the presence of $CO_2$, to produce the polypeptide. Some embodiments, the products produced by the modified organism are isolated or collected. Collected products, such as terpenes and terpenoids, may then be further modified, for example, by refining and/or cracking to produce fuel molecules or components.

In some embodiments, a genetically modified host cell is cultured in a suitable medium (e.g., Luria-Bertoni broth, optionally supplemented with one or more additional agents, such as an inducer (e.g., where the isoprenoid synthase is under the control of an inducible promoter); and the culture medium is overlaid with an organic solvent, e.g. dodecane, forming an organic layer. The compound produced by the genetically modified host partitions into the organic layer, from which it can then be purified. In some embodiments, where a prenyl transferase, isoprenoid synthase mevalonate synthesis-encoding nucleotide sequence is operably linked to an inducible promoter, an inducer is added to the culture medium; and, after a suitable time, the isoprenoid compound is isolated from the organic layer overlaid on the culture medium.

The various products may be further refined to a final product for an end user by a number of processes. Refining can, for example, occur by fractional distillation. For example, a mixture of products, such as a mix of different hydrocarbons with various chain lengths may be separated into various components by fractional distillation.

Refining may also include any one or more of the following steps, cracking, unifying, or altering the product. Large products, such as large hydrocarbons (e.g. ≥C10), may be broken down into smaller fragments by cracking. Cracking may be performed by heat or high pressure, such as by steam, visbreaking, or coking Products may also be refined by visbreaking, for example by thermally cracking large hydrocarbon molecules in the product by heating the product in a furnace. Refining may also include coking, wherein a heavy, almost pure carbon residue is produced. Cracking may also be performed by catalytic means to enhance the rate of the cracking reaction by using catalysts such as, but not limited to, zeolite, aluminum hydrosilicate, bauxite, or silica-alumina. Catalysis may be by fluid catalytic cracking, whereby a hot catalyst, such as zeolite, is used to catalyze cracking reactions. Catalysis may also be performed by hydrocracking, where lower temperatures are generally used in comparison to fluid catalytic cracking. Hydrocracking can occur in the presence of elevated partial pressure of hydrogen gas. Products may be refined by catalytic cracking to generate diesel, gasoline, and/or kerosene.

The products may also be refined by combining them in a unification step, for example by using catalysts, such as platinum or a platinum-rhenium mix. The unification process can produce hydrogen gas, a by-product, which may be used in cracking.

The products may also be refined by altering, rearranging, or restructuring hydrocarbons into smaller molecules. There are a number of chemical reactions that occur in catalytic reforming processes which are known to one of ordinary skill in the arts. Catalytic reforming can be performed in the presence of a catalyst and a high partial pressure of hydrogen. One common process is alkylation. For example, propylene and butylene are mixed with a catalyst such as hydrofluoric acid or sulfuric acid, and the resulting products are high octane hydrocarbons, which can be used to reduce knocking in gasoline blends.

The products may also be blended or combined into mixtures to obtain an end product. For example, the products may be blended to form gasoline of various grades, gasoline with or without additives, lubricating oils of various weights and grades, kerosene of various grades, jet fuel, diesel fuel, heating oil, and chemicals for making plastics and other polymers. Compositions of the products described herein may be combined or blended with fuel products produced by other means known to one skilled in the art.

Some products produced from the host cells of the disclosure, especially after refining, will be identical to existing petrochemicals, i.e. contain the same chemical structure. For instance, crude oil contains the isoprenoid pristane, which is thought to be a breakdown product of phytol; which is a component of chlorophyll. Some of the products may not be the same as existing petrochemicals. However, although a molecule may not exist in conventional petrochemicals or refining, it may still be useful in these industries. For example, a hydrocarbon could be produced that is in the boiling point range of gasoline, and that could be used as gasoline or an additive, even though the hydrocarbon does not normally occur in gasoline.

A product herein can be described by its Carbon Isotope Distribution (CID). At the molecular level, a CID is the statistical likelihood of a single carbon atom within a molecule to be one of the naturally occurring carbon isotopes (for example, $^{12}C$, $^{13}C$, or $^{14}C$). At the bulk level of a product, a CID may be the relative abundance of naturally occurring carbon isotopes for example $^{12}C$, $^{13}C$, or $^{14}C$) in a compound containing at least one carbon atom. It is noted that the CID of a fossil fuel may differ based on its source. For example; with CID(fos), the CID of carbon in a fossil fuel, such as petroleum, natural gas, and coal is distinguishable from the CID (atm), the CID of carbon in current atmospheric carbon dioxide. Additionally, the CID(photo-atm) refers to the CID of a carbon-based compound made by photosynthesis in recent history where the source of inorganic carbon was carbon dioxide in the atmosphere. Also, CID(photo-fos) refers to the CID of a carbon based compound made by photosynthesis in recent history where the source of substantially all of the inorganic carbon was carbon dioxide produced by the burning of fossil fuels (for example, coal, natural gas, and/or petroleum).

The exact distribution is also a characteristic of 1) the type of photosynthetic organism that produced the molecule, and 2) the source of inorganic carbon. These isotope distributions can be used to define the composition of photosynthetically-derived fuel products.

Carbon isotopes are unevenly distributed among and within different compounds and the isotopic distribution can reveal information about the physical, chemical, and metabolic processes involved in carbon transformation. The overall abundance of $^{13}C$ relative to $^{12}C$ in a photosynthetic organism is often less than the overall abundance of $^{13}C$ relative to $^{12}C$ in atmospheric carbon dioxide, indicating that carbon isotope discrimination occurs in the incorporation of carbon dioxide into photosynthetic biomass.

A fuel product can be produced from a biomass, either before or after refining, and the product can be identical to an existing petrochemical, Some of the fuel products may not be the same as existing petrochemicals. In one embodiment, a fuel product is similar to an existing petrochemical, except for the carbon isotope distribution. For example, it is believed that no fossil fuel petrochemicals have a $\delta^{13}C$ distribution of less than −32%, whereas fuel products as described herein can have a $\delta^{13}C$ distribution of less than −32%, less than −35%, less than −40%, less than −45%, less than −50%, less than −55%, or less than −60%. In another embodiment, a fuel product or composition is similar but not the same as an existing fossil fuel petrochemical and has a $\delta^{13}C$ distribution of less than −32%, less than −35%, less than −40%, less than −45%, less than −50%, less than −55%, or less than −60%.

A fuel product can be a composition comprising, for example, hydrogen and carbon molecules, wherein the hydrogen and carbon molecules are at least about 80% of the atomic weight of the composition, and wherein the $\delta^{13}C$ distribution of the composition is less than about −32%. For some fuel products described herein, the hydrogen and carbon molecules are at least 90% of the atomic weight of the composition. For example, a biodiesel or fatty acid methyl ester (which has less than 90% hydrogen and carbon molecules by weight) may not be part of the composition. In still other compositions, the hydrogen and carbon molecules are at least 95 or at least 99% of the atomic weight of the composition. In yet other compositions, the hydrogen and carbon molecules are 100% of the atomic weight of the composition. In some embodiments, the composition is a liquid. In other embodiments, the composition is a fuel additive or a fuel product.

Also described herein is a fuel product comprising a composition comprising: hydrogen and carbon molecules, wherein the hydrogen and carbon molecules are at least 80% of the atomic weight of the composition; and wherein the $\delta^{13}C$ distribution of the composition is less than −32%; and a fuel component. In some embodiments, the $\delta^{13}C$ distribution of the composition is less than about −35%, less than about −40%, less than about −45%, less than about −50%, less than about −55%, or less than about −60%. In some embodiments, the fuel component of the composition is a blending fuel, for example, a fossil fuel, gasoline, diesel, ethanol, jet fuel, or any combination thereof. In still other embodiments, the blending fuel has a $\delta^{13}C$ distribution of greater than −32%. For some fuel products described herein, the fuel component is a fuel additive which may be MTBE, an anti-oxidant, an antistatic agent, a corrosion inhibitor, or any combination thereof. A fuel product as described herein may be a product generated by blending a fuel product as described and a fuel component. In some embodiments, the fuel product has a $\delta^{-3}C$ distribution of greater than −32%. In other embodiments, the fuel product has a $^{13}C$ distribution of less than −32%. For example, an oil composition extracted from an organism can be blended with a fuel component prior to refining (for example, cracking) in order to generate a fuel product as described herein. A fuel component, can be a fossil fuel, or a mixing blend for generating a fuel product. For example, a mixture for fuel blending may be a hydrocarbon mixture that is suitable for blending with another hydrocarbon mixture to generate a fuel product. For example, a mixture of light alkalies may not have a certain octane number to be suitable for a type of fuel, however, it can be blended with a high octane mixture to generate a fuel product. In another example, a composition with a $\delta^{13}C$ distribution of less than −32% is blended with a hydrocarbon mixture for fuel blending to create a fuel product. In some embodiments, the composition or fuel component alone are not suitable as a fuel product, however, when combined, they are useful as a fuel product. In other embodiments, either the composition or the fuel component or both individually are suitable as a filet product. In yet another embodiment, the fuel component is an existing petroleum product, such as gasoline or jet fuel. In other embodiments, the fuel component is derived from a renewable resource, such as bioethanol, biodiesel, and biogasoline.

Oil compositions derived from biomass can be used for producing high-octane hydrocarbon products. Thus, one embodiment describes a method of forming a fuel product, comprising: obtaining an upgraded oil composition, cracking the oil composition, and blending the resulting one or more light hydrocarbons, having 4 to 12 carbons and an Octane number of 80 or higher, with a hydrocarbon having an Octane number of 80 or less. The hydrocarbons having an Octane number of 80 or less are, for example, fossil fuels derived from refining crude oil.

The biomass feedstock can be modified or tagged such that the light hydrocarbon products can be identified or traced back to their original feedstock. For example, carbon isotopes can be introduced into a biomass hydrocarbon in the course of its biosynthesis. The tagged hydrocarbon feedstock can be subjected to the refining processes described herein to produce a light hydrocarbon product tagged with a carbon isotope. The isotopes allow for the identification of the tagged products, either alone or in combination with other untagged products, such that the tagged products can be traced back to their original biomass feedstocks.

The following examples are intended to provide illustrations of the application of the present disclosure. The following examples are not intended to completely define or otherwise limit the scope of the disclosure.

EXAMPLES

Example 1

Petroleum derived oils are processed in the refining industry into, for example, fuels, chemicals, and industrial products. These processes are well established and include, for example, distillation and catalytic upgrading in hydrotreating units as well as upgrading in thermal processing units such as cokers. The refining process is shown schematically in FIG. 2 where incoming feed is first separated by distillation and/or solvent treatment and those fractions are subject to further upgrading, including compositional changes effected in reactors used to catalytically hydrotreat (as described in further details in Examples 2, 3 and 4) the fractions to make products suitable for blending into fuels or for the manufacture of chemicals or industrial products.

These known petroleum refining processes are further detailed in FIG. 3. The refinery feedstocks are first distilled by boiling point into various feedstocks (as shown in the first block) which then go on to processing in units shown in the middle block. Products from these units are then blended into a range of finished products as shown in the third block.

Algae derived oils have been found to be suitable feedstocks to the refining processes. This is also described further in the following examples. Moreover, the algae derived feedstocks produce materials that can be used, for example, for blending into fuels and in the manufacture of chemicals and industrial products.

Exemplary processes that can be involved in the production of a product obtained from a biomass and/or oil composition, specifically possible fractions, possible upgrading techniques, and possible products, are described, for example, in Robinson, P. R. (2006). Petroleum Processing Overview. In Hsu, C. S, and Robinson, P. R. (Eds.), Practical Advances in Petroleum Processing (Vol. 1) (p. 18). New York: Springer Science+Business Media.

Example 2

FIG. 4 illustrates an exemplary, method and system as described herein. A crude algal oil (oil composition), for example, an oil extracted from an algal biomass, is inserted into the system. The algal oil is obtained by crushing the biomass comprising whole cells and acquiring the oil from the algal cells. The algal cells may, for example, contain 50% or greater by weight of lipids or oils. The algal oil then enters the upgrading process which may begin, for example, with an HDM reactor, wherein a catalyst bed within the HDM reactor reacts and/or absorbs any metal containing molecules and/or metal ions onto the surface of the catalyst. The catalyst bed also reacts and/or absorbs metalloids, for example, phosphorous. The oil composition then exits the HDM reactor with a reduced content of metal or metalloid atoms in the composition, for example, less than 1% w/w of the composition. The metal/metalloid atoms are discarded as waste or recycled as nutrients for growing more algal biomass.

The products of the demetallization reactor are then fed to a catalytic desulfurization unit. The HDS reactor is maintained at a temperature ranging from about 315 to about 480 C and a hydrogen partial pressure ranging from about 100 to about 3000 psi. The range of operating pressures and temperatures are exemplary of those employed in the petroleum refining industry and are known to one skilled in the art. The catalyst in the reactor facilitates the removal of sulfur from the chemical compounds in the algae oil by hydrogenation. The sulfur is removed as $H_2S$ which may further be recovered as elemental sulfur using technology well known by those in the petroleum refining industry. The product from the HDS has a reduced sulfur content, for example, less than 1% w/w of the composition.

Continuing with the example in FIG. 4, the algal oil composition then enters a HDN reactor. The HDN reactor comprises a catalyst bed that when in contact with the oil composition removes nitrogen atoms or nitrogen-containing molecules from the composition. The HDN reactor is maintained at a temperature ranging from about 315 to about 480 C and a hydrogen partial pressure ranging from about 100 to about 3000 psi. The range of operating pressures and temperatures are exemplary of those employed in the petroleum refining industry and are known to one skilled in the art. The catalyst in the reactor facilitates the removal of nitrogen from the chemical compounds in the algae oil by hydrogenation. The resulting refined composition from the HDN reactor is now an algal oil composition comprising less than 1% w/w metal/metalloids atoms and less than 1% w/w sulfur and nitrogen atoms. The nitrogen is removed as ammonia. The ammonia can be discarded or reused, for example, as a nutrient for growing algae. Often, as demonstrated in FIG. 4, in parallel with the nitrogen removal, other heteroatoms, for example, sulfur, nitrogen, and phosphorus, that may not have been removed in the earlier HDM reactor in the oil composition, are also removed by hydrogenation, thereby generating additional products, such as hydrogen sulfide, water, carbon monoxide, carbon dioxide, and lighter hydrocarbons (e.g. methane, ethane and butanes).

Finally, the refined oil composition from the crude algal oil enters the HDO reactor. The HDO reactor is similar to the HDN reactor and comprises a catalytic composition that removes the oxygen from the oil composition. As described herein, oxygen can create problems when transporting or combusting a refined oil composition. The catalyst in the HDO reactor and subsequent hydrogenation of oxygen containing molecules and compounds generates side products such as water, carbon monoxide, and carbon dioxide, as demonstrated in FIG. 4, in addition, as before with the HDN reactor, sulfur atoms in the oil composition not previously removed can also be removed by hydrogenation, thereby generating hydrogen sulfide as a side product along with the other side products mentioned above.

After exiting the HDO reactor, a refined composition comprises, for example, light hydrocarbons such as pentane and longer chain hydrocarbons that can be used for generating fuels such as distillates (for example, jet fuel and diesel) or gasoline. These two types of hydrocarbons are separated by distillation. Lube basestocks can also be generated. The refined composition is demonstrated as Green Products in FIG. 4. As an option that is sometimes practiced in the refining industry to increase the yields of gasoline at a refinery, the Green Products can then be sent to catalytic cracking units for further conversion using a LZY-72 catalyst, for example, a Union Carbide Y-type zeolite which is often used as a cracking catalyst. Y-type zeolites have a 3-dimensional pore network with pore mouths of about 8.6 Å that open into larger, nearly spherical cages of a free diameter of about 13 Å. The products of the catalytic cracking reactions can then be further refined into finished gasolines and distillates. An alternative to further catalytically cracking the product is using the green distillates and naphtha directly in distillate and gasoline blending pools.

The upgrading methods can comprise the four steps described in FIG. 4. In addition, two or more of the steps can be combine into a single step. For example, step two (HDS) and step three (HDN) can be combined into a single step. Various combinations of the four steps are well within the knowledge of one of skill in the art.

Example 3

HDM is the process wherein metals (e.g. Mg) and metalloids (e.g. P) are removed from the oil composition and are reacted/absorbed onto the catalyst itself. The HDM catalyst can have a relatively short lifetime. The lifetime and cost-effectiveness of this catalyst can be optimized, for example, by selecting a catalyst/support with a very high surface area and pore volume and by selecting an open pore structure to ensure maximum access of the oil composition and the highest metal and metalloid storage capability. Two parallel catalyst beds (one active on-line, the second packed with fresh catalyst) can be used. One of the two catalysts can be switched out when the other catalyst is spent. In addition, three catalyst beds can be used in a "merry-go-round" configuration, in which one is in-line, the second is filled with fresh catalyst, and the third is being emptied and refilled. The choice of catalysts and configurations will be based on, for example, the metal and metalloid levels in the oil composition, and/or the flow rate. These parameters are within the knowledge of one of skill in the art.

After HDM is largely complete then various combinations of HDS, HDN and HDO can proceed as shown in FIG. 4 either, for example, in sequential reactors or simultaneously within the same reactor.

The final upgraded oil composition of a pure hydrocarbon distillate stream is suitable, for example, for use or blending in distillate blending operations within a refinery, due to its reduced heteroatoms content. The upgraded oil composition is similar or better than that of a premium light, sweet "crude" stream which can be shipped by pipeline and/or further processed using existing technologies.

All four steps can have elevated temperatures (e.g. about 300 to about 500 degrees C.) and high pressures of hydrogen (e.g. more than about 200 psi to more than about 1000 psi).

The catalyst for HDM should have high porosity and/or be able to sequester high levels of metals and/or metalloids. All three catalysts can, for example, comprise a support such as alumina. (or aluminosilicates or silica) and can also comprise two or more metal compounds such as Co/Mo, Ni/Mo and Co/W. Such catalysts are commonly used in petroleum refining and are readily available from catalyst suppliers.

Example 4

Oil from algae was obtained with the composition shown in Table 5 by an extraction process. Also shown in Table 5 is the API Gravity and the H/C ratio (ratio of hydrogen atoms to carbon atoms calculated from the ratio of H % and carbon % given in Table 5 adjusting for the atomic weight of each to get to an atomic ratio). These terms are common descriptors of feedstocks and products in the refining industry.

Notable is the high concentration of oxygen (greater than 10%) and the high concentrations of phosphorus, sodium, and metals (Na, K, Ca). Also notable is the low API of 19.5.

The algae derived oil was then subjected to an RBD treating processes similar to that used in the food industry. The product of this process has the composition in the column labeled RBD treated oil. Notable is that there is improvement in N, P and Na.

The treated oil was then subjected to hydrotreating as described in Examples 2 and 3. Processes that involve HDM, HDN, and HDO were conducted.

The product had the composition that is given in the column labeled Diesel. The boiling point range of this material was within the range of diesel obtained from conventional petroleum and associated refining processes. Notable is the reduction of O levels (from 12.66% to less than 0.5%), P (1.59 ppm to less than 1 ppm) and metal levels (Na from 11.3 ppm to less than 3 ppm, K from 9.85 ppm to less than 4 ppm, and Cu from 4.53 ppm to less than 4 ppm) relative to the algae derived oil and the treated oil. Also notable is the increase in API (reduction in specific gravity) and increase in H/C ratio. This indicates the algal derived oil was catalytically upgraded by the HDM, HDN and HDO steps that occur in conventional hydrotreating operations employed in petroleum refining and described in Examples 2 and 3. In the refining industry, these processes are known to add hydrogen to the product in the course of catalytic and/or thermally removing metals, sulfur, nitrogen and oxygen, as described in Examples 2 and 3.

The diesel product from the catalytic hydrotreating steps is suitable, for example, for use directly in diesel or as a diesel blendstock as is practiced in the refining industry.

TABLE 5

| | Algae derived oil | RBD Treated oil | Diesel |
|---|---|---|---|
| Specific gravity @ 60° F. - ASTMD891-95 | 0.937 | 0.9454 | 0.7837 |
| C | 77.98% | 76.89% | 84.46% |
| H | 11.73% | 10.82% | 14.83% |
| N | 0.89% | <0.5% | <0.5% |
| O | 12.29% | 12.66% | <0.5% |

TABLE 5-continued

| | Algae derived oil | RBD Treated oil | Diesel |
|---|---|---|---|
| S | <0.05% | <0.05% | 0.1061% |
| P | 30.6 ppm | 1.59 ppm | <1 ppm |
| Na | 11.3 ppm | 3.37 ppm | <3 ppm |
| K | 9.85 ppm | <3 ppm | <4 ppm |
| Mg | <2 ppm | <2 ppm | <2 ppm |
| Ca | 4.53 ppm | <4 ppm | <4 ppm |
| API | 19.5 | 18.2 | 49.1 |
| H/C ratio | 1.8 | 1.7 | 2.1 |

Example 5

The entire pond-to-pump value chain at pilot scale has been shown by producing jet fuel with a refining partner. Algal biomass was grown and harvested and the algal oil was extracted via a solvent counter current process. The composition of this algae derived oil is shown in Table 6. Notable is the high concentration of sulfur, nitrogen, oxygen and metals (including phosphorus) and low H/C ratio and API. These properties make the algae derived oil unsuitable for direct use as a fuel.

TABLE 6

| | Algae Oil |
|---|---|
| Specific gravity @ 60° F. - ASTMD891-95 | 0.9756 |
| C | 74.35% |
| H | 10.83% |
| N | 1.34% |
| O | 12.33% |
| S | 0.1853% |
| P | 0.1900% |
| Na | 0.0811% |
| K | 0.1740% |
| Mg | 0.1070% |
| Ca | 0.1890% |
| API | 13.5 |
| H/C ratio | 1.7 |

This oil was refined using the Dynamic Fuels Bio-Synfining™ process to produce on-specification diesel and jet fuel (Hydrotreated Renewable Jet, HRJ). The processes used to upgrade the algae oil are those as described in Examples 2 and 3. In addition, a hydroisomerization process was used after the HDM, HDN, HDS and HDO steps to increase the yield and quality of material suitable for use in jet fuel. Hydroisomerization is a processing step known and commonly used in the refining industry to upgrade petroleum derived hydrocarbons.

The product of the Bio-Synfining™ process was fractionated into three cuts, as shown in Table 7: $C_7$-naphtha, $C_8$-$C_{15}$ Jet fuel (HRJ), and $C_{15+}$ diesel. The resulting crystal clear HRJ conforms to all of the key specifications for both commercial and military applications. The freezing point of the algal-derived HRJ, a particularly critical parameter, is −67° C. This very low freezing point far exceeds the specification's freezing point of −47° C., potentially allowing aircraft to fly at higher altitudes or allowing more $C_{15+}$ fraction to be included in the HRJ fraction resulting in higher yields of on-spec jet fuel. This low freezing point also emphasizes the high efficiency of the hydroisomerization process, and the high degree of isomerization achieved. Other useful products can have a freezing point of, for example, about −60° C. to about −70° C., or about −50° C. to about −75° C.

This pond-to-pump demonstration, conducted at both bench and pilot scale, confirms that algal oil extracted from algal biomass is well-suited for conversion into diesel and jet fuel meeting or surpassing all specifications.

TABLE 7

HRJ Properties from Algal Oil and Conformance to Commercial (Jet A-1) and Military (JP-8) Specifications are shown below.

| Property | Units | ASTM D 1655 Jet A-1 | MIL-83133E JP-8 | Bio-Synfined HRJ from Sapphire Energy Algal oil |
|---|---|---|---|---|
| Flash Point | ° C. | 38 min | 38 min | 39 |
| Distillation End Point | ° C. | 300 max | 300 max | 259 |
| Viscosity, −20° C. | cSt | 8.0 max | 8.0 max | 3.37 |
| Freezing Point | ° C. | −47 max | −47 max | −67 |
| Density* | g/mL | 0.775-0.840 | 0.775-0.840 | 0.76 |
| Smoke Point | ° C. | 25 min | 25 min | >30 |
| Sulfur | ppm | 3,000 max | 3,000 max | 1.6 |
| Color (Saybolt) | — | None | report | +30 |

*Note:
specification range for HRJ is 0.730-0.770 (AFRL)

Figure 9:
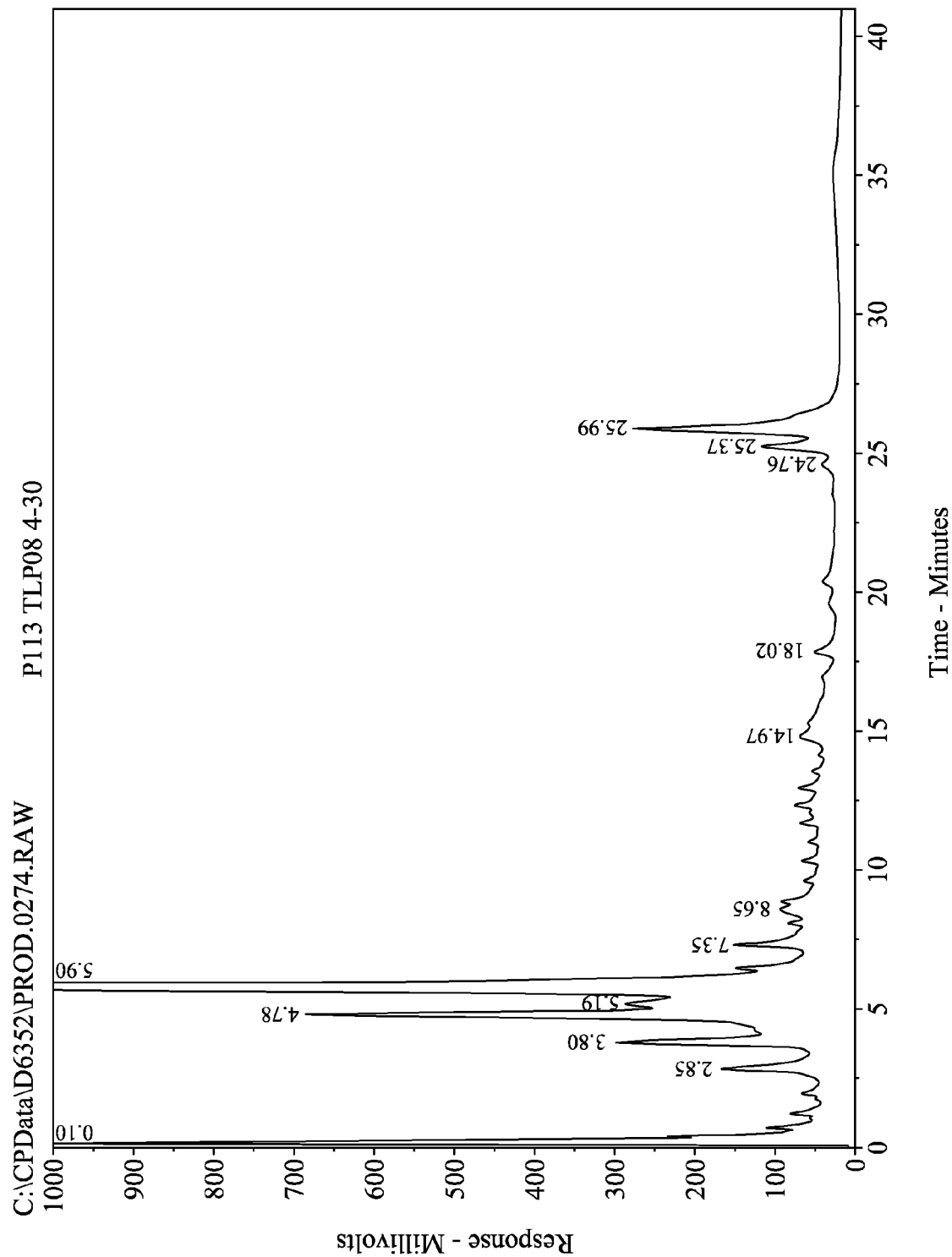
FIG. 9 shows a GC-FID chromatogram.
Figure 10:
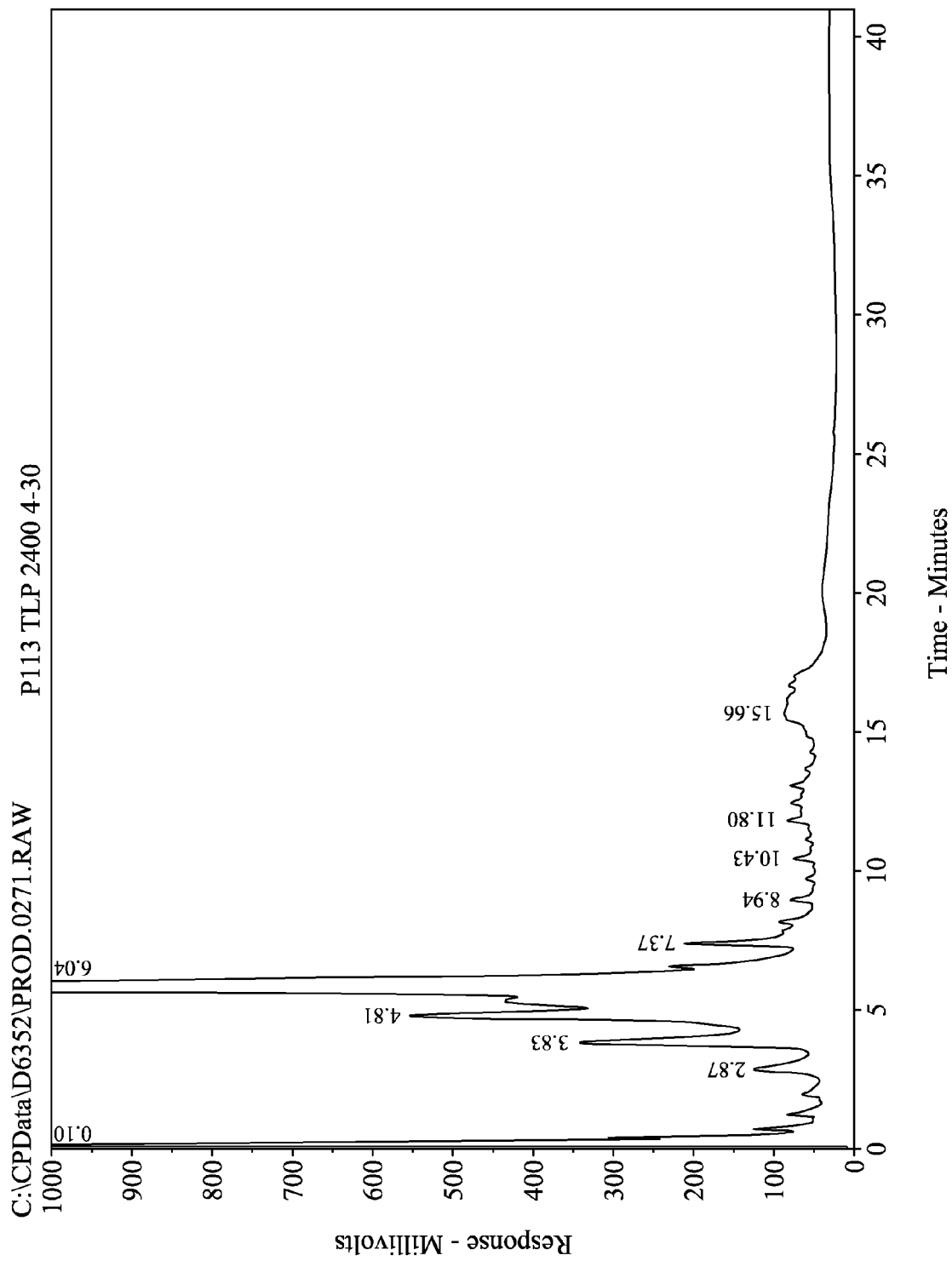
FIG. 10 shows a GC-FID chromatogram.
Figure 11:
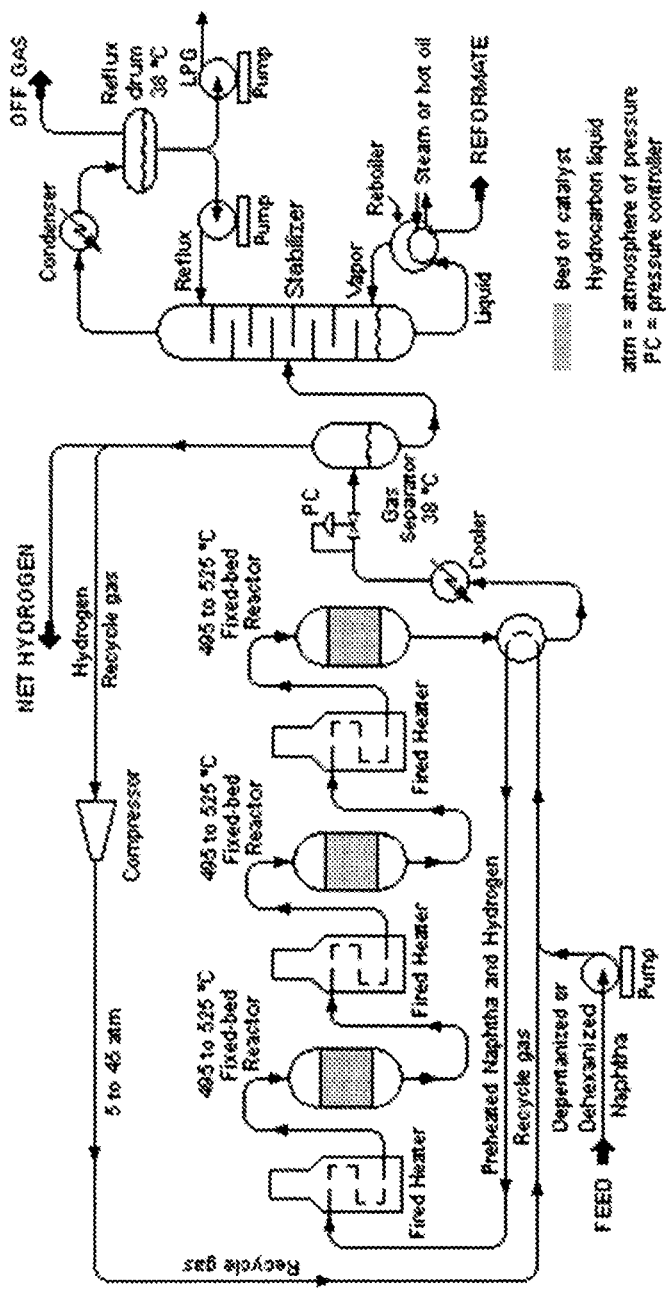
FIG. 11 shows a process flow diagram depicting a typical semi-regenerative catalytic reforming unit.

FIG. 9 shows the GC-FID trace of the partially hydrodeoxygenated algal oil. Peaks eluting after 24 minutes show the presence of residual, unconverted free fatty acids. After optimization of the HDO process, the residual unconverted free fatty acids are absent from the GC-FID chromatogram (FIG. 10). This material is a fully hydrodeoxygenated product that can be further distilled to produce diesel and hydrotreated renewable jet (HRJ) fuel products using standard refining techniques. The characteristics of the HRJ product produced by distillation of the HDO treated material are shown in the table above, along with specifications for ASTM Jet A-1 grade jet filet and Military JP-8 grade jet fuel. In all cases, the HRJ product meets or exceeds both A-1 and JP-8 fuel specifications.

Example 6

The catalytic hydrogenation processes described in Examples 2 and 3 are known to produce materials that can go into diesel and jet (distillate) fuels. These processes also naturally produce lighter (lower boiling point) materials that are suitable for gasoline blending. These materials are typically called naphthas in the petroleum refining industry. These are the same products that are referred to in FIG. 4 as Green Products. Algal derived oils fed to HDM, HDN, and HDO processes as described in Example 4 were found to produce a material lower in boiling point than diesel and jet and with a composition that is similar to that of petroleum derived naphtha.

Table 8 shows a PIONA (paraffin, isoparaffin, naphthene and aromatics) analysis of the naphtha-like product from catalytically hydrotreating algae oil as described in Example 4. Notable is that the composition of the material is made up of molecules containing from 3-12 carbon atoms including paraffins, isoparaffins, naphthenes and aromatics. Olefins are reduced in content which is consistent with the product having come from catalytic hydrotreating processes as described in Examples 2 to 5. The molecular composition of this material is similar to that of naphtha products found in petroleum refining. This material can then be used to feed processing units (naphtha reformers and isomerization units) and/or to produce blendstocks suitable for gasoline blending.

Table 9 shows a detailed breakdown of the molecular composition of the naphtha-like material produced from a catalytically hydrotreated algae oil (Example 4). The data in Table 9 is summarized in Table 8 and again shows the wide range of molecular species present.

TABLE 8

| Carbon number | Paraffin | Isoparaffin | Olefin | Naphthene | Aromatics | Sum |
|---|---|---|---|---|---|---|
| 3 | 0.172 | 0.000 | 0.000 | 0.000 | 0.000 | 0.172457 |
| 4 | 1.506 | 0.963 | 0.000 | 0.000 | 0.000 | 2.46849 |
| 5 | 4.584 | 4.956 | 0.000 | 0.000 | 0.000 | 9.540235 |
| 6 | 7.784 | 9.946 | 0.000 | 1.055 | 0.000 | 18.78386 |
| 7 | 7.964 | 12.870 | 0.000 | 1.389 | 0.108 | 22.33067 |
| 8 | 5.598 | 11.140 | 0.022 | 1.708 | 0.305 | 18.77338 |
| 9 | 3.249 | 10.745 | 0.255 | 1.708 | 0.331 | 16.28928 |
| 10 | 1.237 | 6.519 | 0.061 | 0.622 | 0.089 | 8.528329 |
| 11 | 0.251 | 2.172 | 0.000 | 0.046 | 0.000 | 2.469399 |
| 12 | 0.062 | 0.581 | 0.000 | 0.000 | 0.000 | 0.643905 |
| Sum | 32.40734 | 59.89282 | 0.338234 | 6.528193 | 0.833412 | 100 |

TABLE 9

| Component Name | Wt % GCxGC | Carbon No. | PIONA |
|---|---|---|---|
| toluene | 0.108 | 7 | a |
| Etbenzene | 0.047 | 8 | a |
| m-xylene | 0.113 | 8 | a |
| p-xylene | 0.078 | 8 | a |
| o-xylene | 0.057 | 8 | a |
| 1,4-diethyl-benzene | 0.010 | 8 | a |
| isopropylbenzene | 0.002 | 9 | a |
| propylbenzene | 0.023 | 9 | a |
| 1,3-methylethylbenzene | 0.097 | 9 | a |
| 1,4-methylethylbenzene | 0.030 | 9 | a |
| 1,3,5-trimethylbenzene | 0.037 | 9 | a |
| 1,2-methylethylbenzene | 0.025 | 9 | a |
| 1,2,4-trimethylbenzene | 0.113 | 9 | a |
| 1,2,3-trimethylbenzene | 0.004 | 9 | a |
| 1Et2,4dimethylbenzene | 0.011 | 10 | a |
| 1Me3isopropylbenzene | 0.006 | 10 | a |
| 1Me3propylbenzene | 0.008 | 10 | a |
| 1Me4propylbenzene | 0.023 | 10 | a |
| n-butyl-benzene | 0.026 | 10 | a |
| methylprop-benzene | 0.001 | 10 | a |
| dimethyl-ethylbenzene | 0.014 | 10 | a |
| isobutane | 0.963 | 4 | i |
| 2-methylbutane | 4.956 | 5 | i |
| 2,2-dimethyl-butane | 0.125 | 6 | i |
| 2,3-dimethyl-butane | 0.532 | 6 | i |
| 2-methylpentane | 5.746 | 6 | i |

TABLE 9-continued

| Component Name | Wt % GCxGC | Carbon No. | PIONA |
|---|---|---|---|
| 3-methylpentane | 3.542 | 6 | i |
| 2,2-dimethyl-pentane | 0.149 | 7 | i |
| 2,4-dimethyl-pentane | 0.438 | 7 | i |
| 3,3-dimethyl-pentane | 0.122 | 7 | i |
| 2-methylhexane | 5.362 | 7 | i |
| 2,3-dimethyl-pentane | 0.769 | 7 | i |
| 3-methylhexane | 5.315 | 7 | i |
| 3-ethylpentane | 0.714 | 7 | i |
| 2,2-dimethyl-hexane | 0.125 | 8 | i |
| 2,5-dimethyl-hexane | 0.263 | 8 | i |
| 2,4-dimethyl-hexane | 0.626 | 8 | i |
| 3,3-dimethyl-hexane | 0.017 | 8 | i |
| 2,3,4trimethylpentane | 0.004 | 8 | i |
| 2,3-dimethylpentane | 0.312 | 8 | i |
| 2methyl3ethylpentane | 0.025 | 8 | i |
| 2-methylheptane | 4.874 | 8 | i |
| 4-methylheptane | 0.339 | 8 | i |
| 3,4-dimethyl-hexane | 0.172 | 8 | i |
| 3-methylheptane | 4.382 | 8 | i |
| 2,2,3-trimethyl-hexane | 0.042 | 9 | i |
| 2,3,5trimethylhexane | 0.064 | 9 | i |
| 2,2,5trimethylhexane | 0.096 | 9 | i |
| 2,4-dimethyl-heptane | 0.388 | 9 | i |
| 2,6-dimethyl-heptane | 0.565 | 9 | i |
| 3,3-dimethylheptane | 1.163 | 9 | i |
| 2,5-dimethyl-heptane | 0.080 | 9 | i |
| dimethyl-heptane | 0.047 | 9 | i |
| 2,3-dimethylheptane | 0.363 | 9 | i |
| 3,4-dimethylheptane | 0.152 | 9 | i |
| 4methyloctane | 0.875 | 9 | i |
| 2-methyloctane | 3.892 | 9 | i |
| 3-ethylheptane | 2.923 | 9 | i |
| 3-methyloctane | 0.016 | 9 | i |
| 2,3,4-trimethyl-heptane | 0.079 | 9 | i |
| 2,4,6trimethylheptane | 0.054 | 10 | i |
| 3,3,5-trimethyl-heptane | 0.116 | 10 | i |
| 2,3,6-trimethylheptane | 0.352 | 10 | i |
| 4,4-dimethyl-octane | 0.148 | 10 | i |
| 2,5-dimethyl-octane | 0.461 | 10 | i |
| 2,7-dimethyl-octane | 0.288 | 10 | i |
| 2,5-dimethyl-octane | 0.207 | 10 | i |
| 2,6-dimethyl-octane | 0.427 | 10 | i |
| 3ethyl2methylheptane | 0.380 | 10 | i |
| 3ethyl2methylhept | 0.601 | 10 | i |
| 5methylnonane | 0.554 | 10 | i |
| 4methylnonane | 1.133 | 10 | i |
| 2methylnonane | 0.508 | 10 | i |
| 3ethylC8 | 0.203 | 10 | i |
| 3methylnonane | 1.088 | 10 | i |
| 4,6dimethyl-C9 | 0.240 | 11 | i |
| 2,5 dimethyl-nonane | 0.242 | 11 | i |
| 2,6dimethyl-nonane | 0.129 | 11 | i |
| 6ethyl2methyloctane | 0.210 | 11 | i |
| dimethyl-C9 | 0.215 | 11 | i |
| 3,7dimethyl-nonane | 0.146 | 11 | i |
| dimethyl-nonane | 0.174 | 11 | i |
| 5methyldecane | 0.214 | 11 | i |
| 4methyldecane | 0.155 | 11 | i |
| 2methyldecane | 0.206 | 11 | i |
| 3ethylnonane | 0.043 | 11 | i |
| 3methyidecane | 0.198 | 11 | i |
| 4,6-dimethyl-C10 | 0.059 | 12 | i |
| 2,5-dimethyl-C10 | 0.067 | 12 | i |
| dimethyl-C10 | 0.045 | 12 | i |
| EthylmethylC9 | 0.045 | 12 | i |
| dimethyl-C10 | 0.047 | 12 | i |
| dimethyl-C10 | 0.031 | 12 | i |
| dimethyl-C10 | 0.029 | 12 | i |
| dimethyl-C10 | 0.023 | 12 | i |
| 5methylC11 | 0.075 | 12 | i |
| 4methylC11 | 0.035 | 12 | i |
| 2methylC11 | 0.072 | 12 | i |
| 5methylC11 | 0.052 | 12 | i |
| methylcyclopentane | 0.791 | 6 | n |
| cyclohexane | 0.263 | 6 | n |
| 1,1dimethylcyclopentane | 0.109 | 7 | n |
| 1,c3-dimethylcyclopentane | 0.322 | 7 | n |
| 1,t2dimethylcyclopentane | 0.430 | 7 | n |
| methylcyclohexane | 0.236 | 7 | n |
| Etcyclopentane | 0.293 | 7 | n |
| 1,1,3trimethylcyclopentane | 0.232 | 8 | n |
| 1,2,4trimethylcyclopentane | 0.181 | 8 | n |
| 1,2,3trimethylcyclopentane | 0.075 | 8 | n |
| 1,c3-dimethylcyclohexane | 0.214 | 8 | n |
| t-1,4-dimethylcyclohexane | 0.106 | 8 | n |
| 1,1-dimethylcyclohexane | 0.071 | 8 | n |
| t-1,3-ethylmethycyclopentane | 0.107 | 8 | n |
| c-1,3-ethylmethycyclopentane | 0.076 | 8 | n |
| c-1,2-ethylmethycyclopentane | 0.267 | 8 | n |
| t-1,2-dimethylcyclohexane | 0.062 | 8 | n |
| c-1,4-dimethyl-cyclohexane | 0.155 | 8 | n |
| 1methylethylcyclopentane | 0.060 | 8 | n |
| c1Et3Mecyclopentane | 0.040 | 8 | n |
| propylcyclopentane | 0.061 | 8 | n |
| c-1,3,5-trimethyl-cyclohexane | 0.319 | 9 | n |
| 1,1,3trimethylcyclohexane | 0.060 | 9 | n |
| t-1,3-diethylcyclopentane | 0.104 | 9 | n |
| t-1,2-diethylcyclopentane | 0.109 | 9 | n |
| 1,2,4-trimethylcyclohexane | 0.126 | 9 | n |
| t-1,3,5-trimethyl-cyclohexane | 0.024 | 9 | n |
| 2Mepropylcyclopentane | 0.009 | 9 | n |
| 1,1,2-trimethylcyclohexane | 0.034 | 9 | n |
| 1methyl2prop-cyclopentane | 0.192 | 9 | n |
| c-1ethyl2methylcyclohexane | 0.211 | 9 | n |
| t-1ethyl4methylcyclohexane | 0.074 | 9 | n |
| butylcyclopentane | 0.072 | 9 | n |
| ethylmethylcyclohexane | 0.092 | 9 | n |
| ethylmethylcyclohexane | 0.030 | 9 | n |
| 1Me2propcyclopentane | 0.009 | 9 | n |
| isopropylcyclohexane | 0.022 | 9 | n |
| ethylmethycyclohexane | 0.005 | 9 | n |
| propylcyclohexane | 0.107 | 9 | n |
| n-butylcyclopentane | 0.078 | 9 | n |
| 2Meocthydrpentane | 0.001 | 9 | n |
| c-1Et2Mecyclobexane | 0.029 | 9 | n |
| 1Mebutylcyclopentane | 0.052 | 10 | n |
| 1Me3(2Mepr)cyp | 0.190 | 10 | n |
| 1ethyl2,3dimethylcyclohexane | 0.000 | 10 | n |
| 1123tetrMecyclohexane | 0.016 | 10 | n |
| 1Et2,4dimethylcyclohexane | 0.001 | 10 | n |
| 1123tetraMecyclohexane | 0.012 | 10 | n |
| 1isopro3Metcyclohexane | 0.038 | 10 | n |
| 1Me3propcyclohexane | 0.041 | 10 | n |
| 1,2-dimethylcyoctane | 0.051 | 10 | n |
| 1butyl3Mecypentane | 0.081 | 10 | n |
| 1but2Etcybutane | 0.042 | 10 | n |
| bicyclodecane | 0.037 | 10 | n |
| 1Meprop-cyclohexane | 0.004 | 10 | n |
| butylcyclohexane | 0.035 | 10 | n |
| pentylcyclopentane | 0.024 | 10 | n |
| 1Et3propcyclohexane | 0.027 | 11 | n |
| 11335pentMecyclohexane | 0.019 | 11 | n |
| 1,4-octadiene | 0.022 | 8 | o |
| 2-nonene | 0.104 | 9 | o |
| 6methyl1octene | 0.104 | 9 | o |
| 3methylcyoctene | 0.048 | 9 | o |
| 2,6dimethyl4octene | 0.061 | 10 | o |
| propane | 0.172 | 3 | p |
| butane | 1.506 | 4 | p |
| pentane | 4.584 | 5 | p |
| hexane | 7.784 | 6 | p |
| heptane | 7.964 | 7 | p |
| octane | 5.598 | 8 | p |
| nonane | 3.249 | 9 | p |
| decane | 1.237 | 10 | p |
| undecane | 0.251 | 11 | p |
| dodecane | 0.062 | 12 | p |

White certain embodiments have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method of producing diesel fuel or diesel blendstock from an algal-oil feedstock, comprising:
   a) providing an algal-oil feedstock comprising greater than about 0.0528% to about 4.8% w/w nitrogen, greater than about 6.81% to about 15.64% w/w oxygen, greater than about 0.0344% to about 0.9% w/w sulfur, greater than about 0.0006% to about 0.83% w/w phosphorus, and greater than about 0.6% to about 62% w/w chlorophyll or chlorophyllide; and
   b) refining the algal-oil feedstock to obtain the diesel fuel or diesel blendstock by a method comprising, hydrotreating the algal-oil feedstock at a temperature of from about 315 to about 480° C. (from about 600 to about 900° F.), a total pressure and/or hydrogen partial pressure of from about 100 to about 3000 psi, a hydrogen to oil ratio of from about 100 to about 2000 scf/Bbl, and a space velocity from about 1.5 vol of oil per vol of catalyst per hour to about 8 vol of oil per vol of catalyst per hour;
   wherein the diesel fuel or diesel blendstock comprises an oxygen level of less than or equal to about 0.5% w/w, a nitrogen level of less than or equal to about 0.5% w/w, and less than or equal to about 1 ppm phosphorus.

2. The method of claim 1, wherein the refining removes from the algal-oil feedstock at least one of the following: Boron (B), Calcium (Ca), Chromium Cr), Copper (Cu), Iron (Fe), Lead (Pb), Lithium (Li), Magnesium (Mg), Manganese (Mn), Nickel (Ni), Phosphorus (P), Potassium (K), Silicon (Si), Sodium (Na), Strontium (Sr), or Zinc (Zn).

3. The method of claim 1, wherein hydrotreating comprises the use of at least one catalyst comprising: a metal such as Ni/Mo, Co/Mo, Co/W, W/Mo, or Ni/W; a noble metal; a zeolite; Ni/Mo supported on alumina; Co/Mo supported on alumina; Ni/W supported on alumina; a metal of Group VIA, Group VIb, or Group VIII of Periodic Table of Elements; or a metal of Group VIb or Group VIII of Periodic Table of Elements supported on a porous refractory oxide carrier.

4. The method of claim 1, wherein refining of the algal-oil feedstock further comprises refining, bleaching, and deodorizing the algal-oil feedstock prior to hydrotreating.

5. The method of claim 1, wherein the algal-oil feedstock is derived from *Chlamydomonas reinhardtii, Dunaliella salina, Haematococcus pluvialis, Scenedesmus dimorphus, Dunaliella viridis, Dunaliella tertiolecta, Nannochloropsis oculata, Nannochloropsis oceania*, a *Chlorella* species, or *Nannochloropsis salina*.

6. A method of producing jet fuel from an algal-oil feedstock, comprising:
   a) providing an algal-oil feedstock comprising greater than about 0.0528% to about 4.8% w/w nitrogen, greater than about 6.81% to about 15.64% w/w oxygen, greater than about 0.0344% to about 0.9% w/w sulfur, greater than about 0.0006% to about 0.83% w/w phosphorus, and greater than about 0.6% to about 62% w/w chlorophyll or chlorophyllide; and
   b) refining the algal-oil feedstock to obtain the jet fuel by a method comprising, hydrotreating the algal-oil feedstock at a temperature of from about 315 to about 480° C. (from about 600 to about 900° F.), a total pressure and/or hydrogen partial pressure of from about 100 to about 3000 psi, a hydrogen to oil ratio of from about 100 to about 2000 scf/Bbl, and a space velocity from about 1.5 vol of oil per vol of catalyst per hour to about 8 vol of oil per vol of catalyst per hour;
   wherein the jet fuel comprises a freezing point of less than −47° C., a smoke point of greater than about 30° C., and about 1.6 ppm sulfur.

7. The method of claim 6, wherein the refining removes from the algal-oil feedstock at least one of the following: Boron (B), Calcium (Ca), Chromium Cr), Copper (Cu), Iron (Fe), Lead (Pb), Lithium (Li), Magnesium (Mg), Manganese (Mn), Nickel (Ni), Phosphorus (P), Potassium (K), Silicon (Si), Sodium (Na), Strontium (Sr), or Zinc (Zn).

8. The method of claim 6, wherein hydrotreating comprises the use of at least one catalyst comprising: a metal such as Ni/Mo, Co/Mo, Co/W, W/Mo, or Ni/W; a noble metal; a zeolite; Ni/Mo supported on alumina: Co/Mo supported on alumina; Ni/W supported on alumina; a metal of Group VIA, Group VIb, or Group VIII of Periodic Table of Elements; or a metal of Group VIb or Group VIII of Periodic Table of Elements supported on a porous refractory oxide carrier.

9. The method of claim 6, wherein the refining of the algal-oil feedstock further comprises cracking, isomerization and fractionation.

10. The method of claim 6, wherein the algal-oil feedstock is derived from *Chlamydomonas reinhardtii, Dunaliella salina, Haematococcus pluvialis, Scenedesmus dimorphus, Dunaliella viridis, Dunaliella tertiolecta, Nannochloropsis oculata, Nannochloropsis oceania*, a *Chlorella* species, or *Nannochloropsis salina*.

11. The method of claim 1, wherein said hydrotreating is a single stage hydrotreating at a pressure from about 1000 to about 3000 psi to remove said chlorophyll or chlorophyllide form said algal-oil feedstock.

12. The method of claim 6, wherein said hydrotreating is a single stage hydrotreating at a pressure from about 1000 to about 3000 psi to remove said chlorophyll or chlorophyllide form said algal-oil feedstock.

* * * * *